(12) United States Patent
Hittinger et al.

(10) Patent No.: US 12,049,660 B2
(45) Date of Patent: Jul. 30, 2024

(54) GENE DUPLICATIONS FOR CRABTREE-WARBURG-LIKE AEROBIC XYLOSE FERMENTATION

(71) Applicant: Wisconsin Alumni Research Foundation (WARF), Madison, WI (US)

(72) Inventors: Chris Todd Hittinger, Madison, WI (US); Trey Sato, Madison, WI (US); Sae-Byuk Lee, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 18/052,410

(22) Filed: Nov. 3, 2022

(65) Prior Publication Data

US 2023/0227861 A1    Jul. 20, 2023

Related U.S. Application Data

(60) Provisional application No. 63/275,308, filed on Nov. 3, 2021.

(51) Int. Cl.
| | |
|---|---|
| *C12P 7/10* | (2006.01) |
| *C10L 1/02* | (2006.01) |
| *C12N 9/02* | (2006.01) |
| *C12N 9/10* | (2006.01) |
| *C12N 9/12* | (2006.01) |
| *C12N 9/92* | (2006.01) |

(52) U.S. Cl.
CPC .................. *C12P 7/10* (2013.01); *C10L 1/02* (2013.01); *C12N 9/0093* (2013.01); *C12N 9/1022* (2013.01); *C12N 9/1205* (2013.01); *C12N 9/92* (2013.01); *C12Y 117/99* (2013.01); *C12Y 202/01002* (2013.01); *C12Y 207/01017* (2013.01); *C12Y 503/01005* (2013.01); *C10L 2200/0469* (2013.01)

(58) Field of Classification Search
None
See application file for complete search history.

(56) References Cited

U.S. PATENT DOCUMENTS

2023/0227861 A1*    7/2023   Hittinger ........ C12Y 202/01002
                                                        435/165

OTHER PUBLICATIONS

Jeong, Deokyeol, "Metabolic engineering considerations for the heterologous expression of xylose-catabolic pathways in *Saccharomyces cerevisiae*", Plos One, (Jul. 27, 2020), 18 pgs.
Xu, Haiqing, "PHO13 deletion-induced transcriptional activation prevents sedoheptulose accumulation during xylose metabolism in engineered *Saccharomyces cerevisiae*", ScienceDirect Metabolic Engineering 34, (2016), 9 pgs.
Bracher, J. M., et al., "Reassessment of requirements for anaerobic xylose fermentation by engineered, non-evolved *Saccharomyces cerevisiae* strains", FEMS Yeast Res. 19, (2019).
Demeke, M., et al., "Development of a D-xylose fermenting and inhibitor tolerant industrial *Saccharomyces cerevisiae* strain with high performance in lignocellulose hydrolysateusing metabolic and evolutionary engineering", Biotechnol Biofuels. 6: 89, (2013), 24 pgs.
Kuyper, M., et al., "Metabolic engineering of a xylose-isomerase-expressing *Saccharomyces cerevisiae* strain for rapid anaerobic xylose fermentation", FEMS Yeast Res. 5, (2005), 399-409.
Lee, Sae-Byuk, et al., "Crabtree/Warburg-like aerobic xylose fermentation by engineered *Saccharomyces cerevisiae*", Metabolic Engineering, vol. 68, (2021), 119-130.
Verhoeven, M. D., et al., "Mutations in PMR1 stimulate xylose isomerase activity and anaerobic growth on xylose of engineered *Saccharomyces cerevisiae* by influencing manganese homeostasis", Sci Rep. 7: 46155, (2017), 1-11.

* cited by examiner

*Primary Examiner* — Christian L Fronda
(74) *Attorney, Agent, or Firm* — Daniel A. Blasiole; DeWitt LLP

(57) ABSTRACT

An engineered yeast strain capable of efficient fermentation of xylose to ethanol, and methods of making and using the strain, are provided.

20 Claims, 18 Drawing Sheets

Specification includes a Sequence Listing.

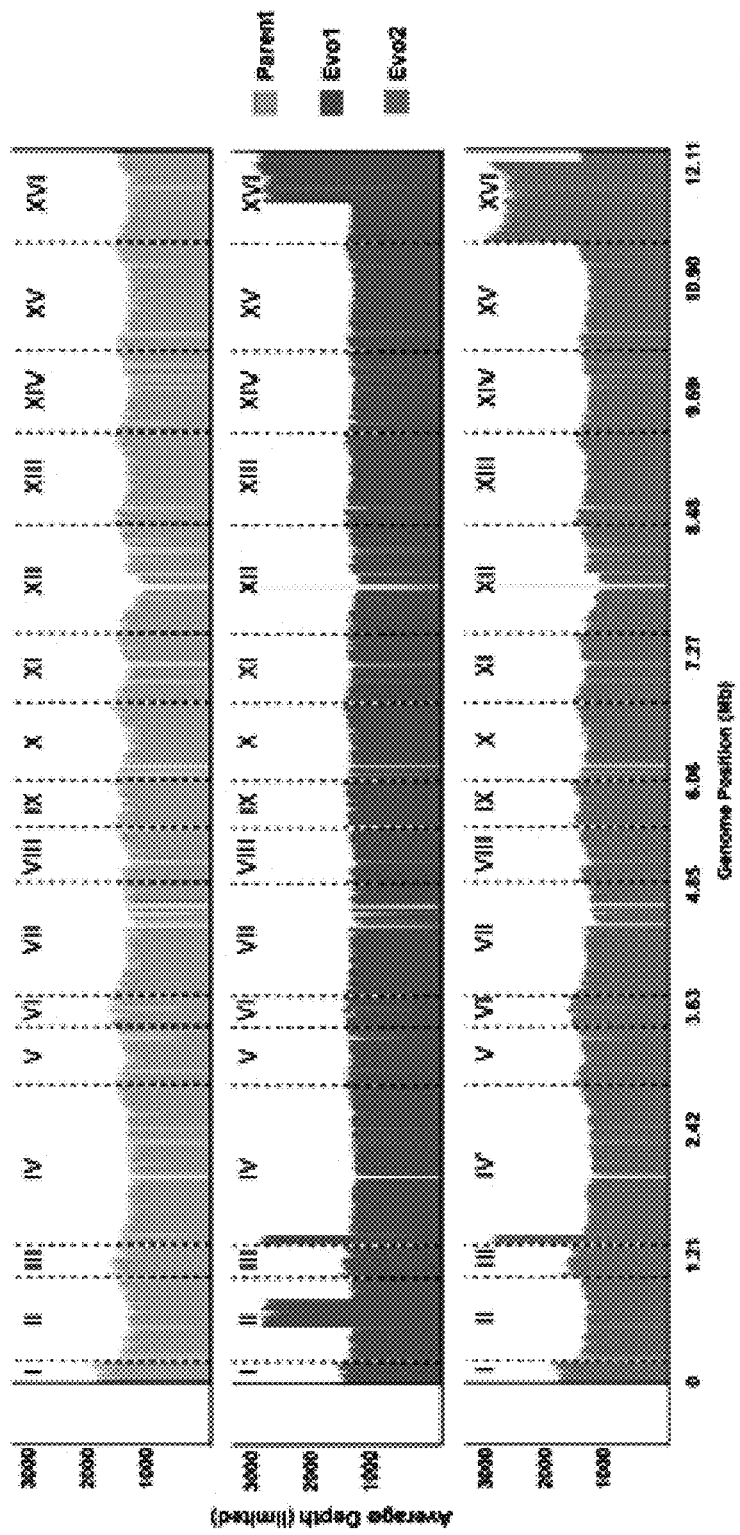
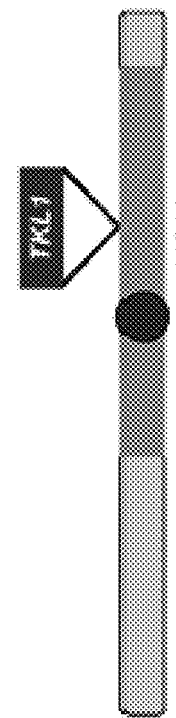
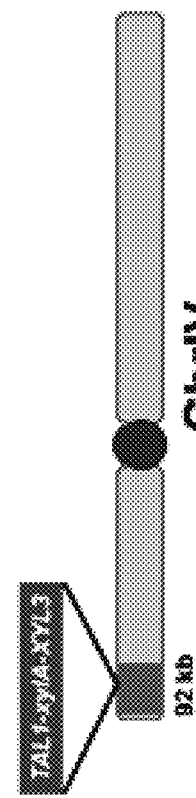
Fig. 3A
Fig. 3B
Fig. 3C

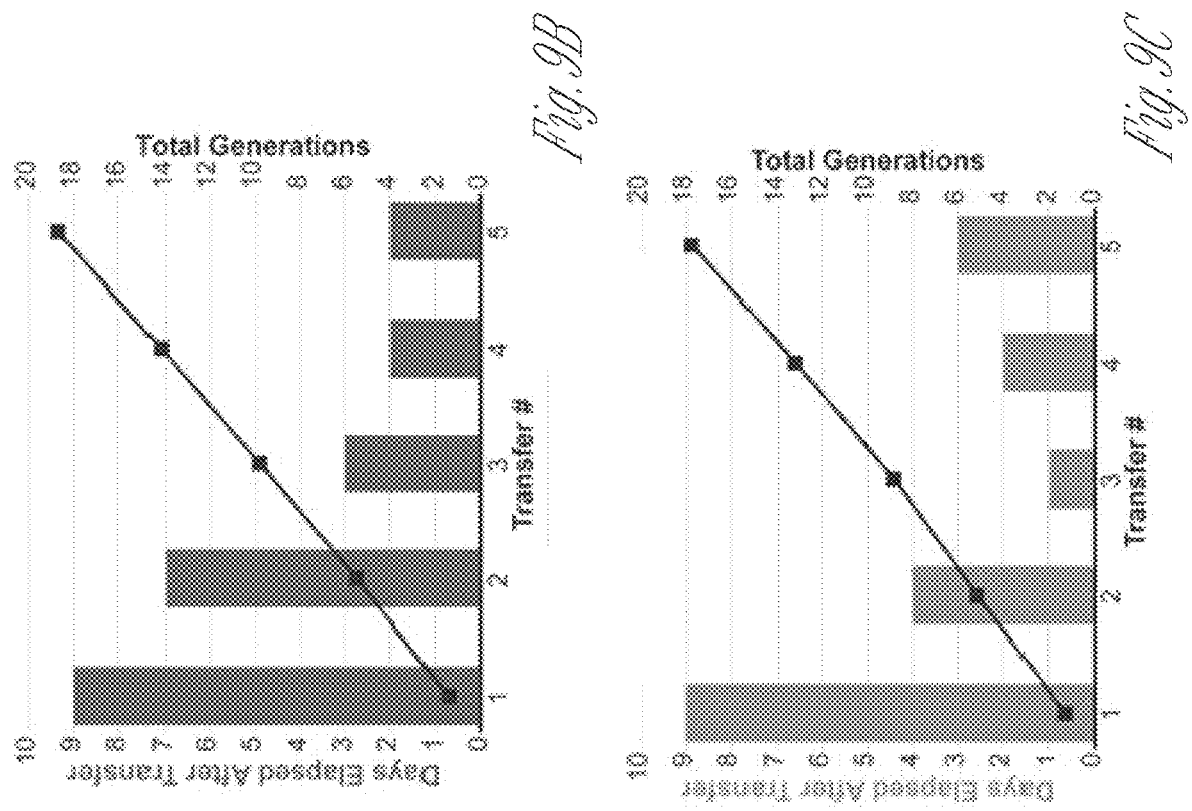
*Fig. 9B*
*Fig. 9C*
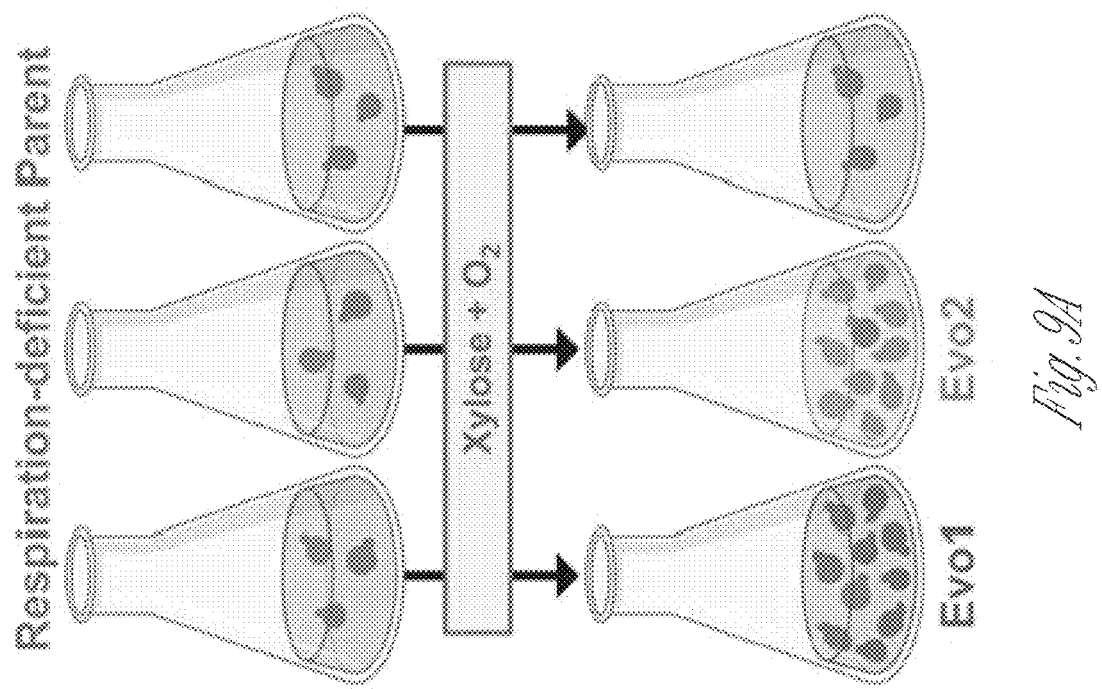
*Fig. 9A*

GENE DUPLICATIONS FOR CRABTREE-WARBURG-LIKE AEROBIC XYLOSE FERMENTATION

CROSS-REFERENCE TO RELATED APPLICATIONS

This application claims the benefit of the filing date of U.S. application No. 63/275,308, filed on Nov. 3, 2021, the disclosure of which is incorporated by reference herein.

STATEMENT OF GOVERNMENT SUPPORT

This invention was made with government support under DE-FC02-07ER64494 and DE-SC0018409 awarded by the US Department of Energy. The government has certain rights in the invention.

INCORPORATION BY REFERENCE OF SEQUENCE LISTING

A Sequence Listing is provided herewith as an xml file, "2312537.xml" created on Feb. 28, 2023, and having a size of 38,948 bytes. The content of the xml file is incorporated by reference herein in its entirety.

BACKGROUND

Over the past few decades, lignocellulosic biomass derived from non-edible plants, such as switchgrass, have been developed as potentially sustainable feedstocks for the production of renewable biofuels, which can replace petroleum-based fuels (Narayanaswamy et al., 2011; Sun and Jin, 2021; Williams et al., 2019). Most lignocellulosic feedstocks require thermo-chemical pretreatment and enzymatic hydrolysis to break down cellulose and hemicellulose in plant cell walls into glucose and xylose, which are the dominant hexoses and pentoses, respectively (Pauly and Keegstra, 2008). However, native *Saccharomyces cerevisiae*, the main fermentative microbe used by the bioethanol industry, does not consume or ferment xylose, resulting in inefficient cellulosic biofuel production whose cost is not competitive with fossil fuels (Cunha et al., 2019; Kim et al., 2013).

To overcome the economic issues impeding the commercialization of lignocellulosic-based biofuels, genetic engineering and adaptive laboratory evolution (ALE) of *S. cerevisiae* have been widely-used strategies for increasing the rate of xylose fermentation into ethanol, isobutanol, lactic acid and other useful biproducts. Enabling xylose utilization by *S. cerevisiae* has been achieved by the introduction of xylose metabolism enzymes from other fungi or bacteria. Xylose reductase and xylitol dehydrogenase (XR-XDH) (Jin et al., 2000; Johansson et al., 2001) or xylose isomerase (XI) (Brat et al., 2009; Kuyper et al., 2005) enzymes convert xylose into xylulose. Both pathways require xylulokinase (XK) to phosphorylate xylulose into xylulose-5-phosphate, which can then be converted into ethanol via the pentose phosphate pathway and glycolysis (Hahn-Hagerdal et al., 2007). Individual insertions of these pathways into *S. cerevisiae* have not been sufficient for xylose-to-ethanol conversion at industrially relevant rates and yields in lignocellulosic hydrolysates, prompting many to explore additional genetic improvements. See a comprehensive review on genetic discoveries that enhance xylose consumption by the XR-XDH pathway, e.g., Kwak and Jin, 2017).

For the XI pathway, several groups have employed combinations of rational engineering and ALE to uncover genetic modifications that increase xylose consumption and conversion into ethanol. Mutations in GRE3 (Lee et al., 2012; Lee et al., 2014; Sato et al., 2016; Traff et al., 2001), which encodes an aldose reductase capable of converting xylose into xylitol, an inhibitor of XI (Yamanaka, 1969); PHO13 (Bamba et al., 2016; Lee et al., 2014); and HXT7 (Reider Apel et al., 2016) were discovered by rational engineering and ALE to improve xylose consumption. Increased expression of XI by targeted or evolved integration of multiple XI copies into the genome has also been found to enhance xylose consumption (Dos Santos et al., 2016; Jeong et al., 2020). Finally, genome sequencing of strains from ALE identified synergistic interactions between loss of function mutations in HOG1, ISU1, and IRA2 genes that enhance xylose consumption by *S. cerevisiae* (Dos Santos et al., 2016; Sato et al., 2016). These genetic changes impacted various metabolic pathways, including xylose catabolism, the pentose phosphate pathway, glycolysis, and respiration, which together enhanced aerobic and anaerobic xylose consumption (Sato et al., 2016).

Despite the use of multiple genetic strategies, xylose fermentation by engineered *S. cerevisiae* strains has not attained nearly the same rate and yield as native glucose fermentation. Glucose uptake and catabolism occur with such high flux that *S. cerevisiae* ferments glucose at high concentrations even in the presence of oxygen (Crabtree, 1929; Warburg et al., 1927), despite the trade off in lower ATP yield compared to aerobic respiration. This phenomenon, known as the Crabtree-Warburg Effect, may have emerged in *S. cerevisiae* through the evolution of intricate regulatory mechanisms, such as down regulation of genes functioning in respiration through glucose repression, and whole genome duplication (Conant and Wolfe, 2006; Lin and Li, 2011; Pfeiffer and Morley, 2014; Thompson et al., 2013). The funneling of glucose towards fermentative metabolism aerobically is thought to occur by the overflow of pyruvate from respiration into ethanol-producing fermentation, consequentially providing *S. cerevisiae* with a competitive advantage against ethanol-sensitive microbes in the natural environments (Kotter and Ciriacy, 1993; Pronk et al., 1996).

In contrast to glucose, several studies have determined that strains of *S. cerevisiae* engineered for xylose metabolism primarily respire xylose in the presence of oxygen. For example, under aerobic conditions, an engineered, xylose-fermenting strain with a mutation in ISU1 upregulated proteins involved in mitochondrial respiration when grown on xylose (Sato et al., 2016). Furthermore, treatment of this strain with Antimycin A, an inhibitor of oxidative phosphorylation, blocks aerobic growth and consumption of xylose. Others have reported that xylose-metabolizing *S. cerevisiae* strains recognize xylose as a non-fermentable carbon source, resulting in the up-regulation of genes related to TCA cycle, glyoxylate pathway, respiratory metabolism, and gluconeogenesis when cultivated on xylose aerobically (Jin et al., 2004; Runquist et al., 2009; Salusjarvi et al., 2008; Scalcinati et al., 2012). These results indicate that xylose flux in engineered strains may not be high enough to cause the overflow of pyruvate into ethanol aerobically, which happens naturally for glucose in yeasts demonstrating the Crabtree/Warburg Effect.

SUMMARY

In one embodiment, an engineered *Saccharomyces cerevisiae* strain capable of efficient fermentation of xylose to ethanol is provided. In one embodiment, an engineered yeast may be obtained through directed evolution, where strains are identified as producing more ethanol than previously possible from a given feedstock through xylose fermentation. An engineered strain may also be prepared by introducing the genetic alterations found in the evolved strains into other strains. For instance, evolved strains are sequenced and that information is used to genetically engineer a strain that is very effective at fermenting xylose, e.g., conversion of xylose to ethanol at 55% of the theoretical maximum yield. In one embodiment, duplications of genes encoding engineered xylose metabolism enzymes, as well as TKL1, a gene encoding a transketolase in the pentose phosphate pathway, were genetic changes associated with the evolved phenotype. Reengineered duplications of genes of these enzymes, in combination with deletion mutations in HOG1, ISU1, GRE3, and IRA2, increased the rates of aerobic and anaerobic xylose fermentation. Xylose fermentation activity of an engineered strain was also demonstrated using an industrially relevant switchgrass hydrolysate (biomass processed to free sugars for fermentation). A xylose-fermenting yeast strain allows for large-scale utilization of xylose as well as glucose in processing of biomass into ethanol. Utilization of the xylose portion of biomass, e.g., from corn stover, would lead to a large increase in the overall efficiency of, for example, corn biofuel production and allow for utilization of more xylose-rich alternative feedstocks. Lignocellulose feedstocks have been cost prohibitive for the amount of ethanol recovered. Other substrates that may be employed include but are not limited to switchgrass, poplar, sorghum and sugarcane bagasse.

In one embodiment, a recombinant yeast is provided that has been genetically engineered to include one or more copies of one or more non-native genes that facilitate xylose fermentation, wherein the non-native genes include a xylulokinase gene (e.g., XYL3) or a xylose isomerase gene (e.g., XYLA); and include one or more additional copies of one or more genes, e.g., native genes, that encode a transaldolase (e.g., Tal1) or a transketolase (e.g., Tkl); and optionally include one or more of a disabling mutation in a gene encoding Cox15 polypeptide so as to exhibit reduced amounts of functional Cox15 polypeptide; a disabling mutation in a gene encoding Isu1 polypeptide so as to exhibit reduced amounts of functional Isu1 polypeptide, a disabling mutation in a gene encoding Hog1 polypeptide so as to exhibit reduced amounts of functional Hog1 polypeptide, a disabling mutation in a gene encoding Ira2 polypeptide so as to exhibit reduced amounts of functional Ira2 polypeptide, or a disabling mutation in a gene encoding Gre3 polypeptide so as to exhibit reduced amounts of functional Gre3 polypeptide, or any combination thereof. In one embodiment, the gene encoding xylulokinase and the gene encoding xylose isomerase are from different organisms. In one embodiment, the gene encoding xylulokinase and the gene encoding xylose isomerase are from the same organism. In one embodiment, the gene encoding xylulokinase is from a different genus or species of yeast. In one embodiment, the gene encoding xylose isomerase is from a bacterium. In one embodiment, the bacterium is *Clostridium. Streptomyces, Bacteroidetes, Bacteroides, E. coli,* or *Bacillus*. In one embodiment, the recombinant yeast is from the genus *Saccharomyces*. In one embodiment, the recombinant yeast has at least two copies of the gene encoding xylulokinase. In one embodiment, the recombinant yeast has one copy of the gene encoding xylulokinase. In one embodiment, the recombinant yeast has one copy of the gene encoding xylose isomerase. In one embodiment, the recombinant yeast has at least two copies of the gene encoding xylose isomerase. In one embodiment, the recombinant yeast has one additional copy of the gene encoding transketolase. In one embodiment, the recombinant yeast has at least two additional copies of the gene encoding transketolase. In one embodiment, the recombinant yeast has one additional copy of the gene encoding transaldolase. In one embodiment, the recombinant yeast has at least two additional copies of the gene encoding transaldolase. In one embodiment, the disabling mutation in the gene encoding Isu1 polypeptide comprises a substitution of a tyrosine for the histidine at amino acid residue position 138 of SEQ ID NO:3. In one embodiment, the disabling mutation in the gene encoding Hog1 polypeptide comprises a deletion of the adenine at nucleotide position 844 of SEQ ID NO:7. In one embodiment, the transketolase has at least 80% amino acid sequence identity to SEQ ID NO:17 or SEQ ID NO:18. In one embodiment, the transaldolase has at least 80% v amino acid sequence identity to SEQ ID NO:19 or SEQ ID NO:20. In one embodiment, the xylose isomerase has at least 80% v amino acid sequence identity to any one of SEQ ID Nos. 10-12. In one embodiment, the xylulokinase has at least 80% amino acid sequence identity to any one of SEQ ID Nos. 13-16.

Further provided is a yeast inoculum, comprising the recombinant yeast described herein and a culture medium.

Also provided is a method of fermenting a hydrolysate having xylose into ethanol, comprising: contacting under ethanol-producing conditions the recombinant yeast and the hydrolysate for a period of time sufficient to allow fermentation of at least a portion of the hydrolysate into ethanol. In one embodiment, the method further comprises separating the ethanol from fermented hydrolysate. In one embodiment, the method further comprises hydrolyzing a cellulosic material to produce the hydrolysate comprising xylose; and contacting the recombinant yeast to the hydrolysate under conditions that permit fermentation. In one embodiment, the cellulosic material comprises a lignocellulosic biomass. In one embodiment, the lignocellulosic biomass comprises at least one material selected from the group consisting of agricultural residues, wood, municipal solid wastes, paper and pulp industry wastes, and herbaceous crops. In one embodiment, the conditions include aerobic conditions. In one embodiment, the conditions include anaerobic conditions.

In one embodiment, a recombinant yeast is provided that has been genetically engineered to include one or more additional copies of a native transketolase gene (e.g., encoding Tkl1) or a combination of a non-native xylulokinase gene (e.g., XYL3), a non-native xylose isomerase gene (e.g., XYLA), and a native transaldolase gene (e.g., encoding TAL1); and optionally include one or more of a disabling mutation in a gene encoding Cox15; a disabling mutation in a gene encoding Isu1 polypeptide so as to exhibit reduced amounts of functional Isu1 polypeptide, a disabling mutation in a gene encoding Hog1 polypeptide so as to exhibit reduced amounts of functional Hog1 polypeptide, a disabling mutation in a gene encoding Ira2 polypeptide so as to exhibit reduced amounts of functional Ira2 polypeptide, or a disabling mutation in a gene encoding Gre3 polypeptide so as to exhibit reduced amounts of functional Gre3 polypeptide.

In one embodiment, a recombinant yeast is provided that has been genetically engineered to: include at least two additional copies of a native transketolase gene, at least two copies of a non-native xylulokinase gene, at least two copies of a non-native xylose isomerase gene, and at least two additional copies of a native transaldolase gene; and optionally to include one or more of a disabling mutation in a gene encoding Cox15; a disabling mutation in a gene encoding ISU1 polypeptide so as to exhibit reduced amounts of functional Isu1 polypeptide, a disabling mutation in a gene encoding Hog1 polypeptide so as to exhibit reduced amounts of functional Hog1 polypeptide, a disabling mutation in a gene encoding Ira2 polypeptide so as to exhibit reduced amounts of functional Ira2 polypeptide, or a disabling mutation in a gene encoding Gre3 polypeptide so as to exhibit reduced amounts of functional Gre3 polypeptide.

BRIEF DESCRIPTION OF THE FIGURES

FIG. 3A-3C. Two independently evolved clones that ferment xylose aerobically contain overlapping duplications in ChrIV and ChrXVI. Average read depths between Y22-3 parental strain (Parent) and the evolved strains (Evo1 and Evo2) were analyzed using spplDer (Langdon et al., 2018) (A). TAL1-xylA-XYL3 expression cassette and TKL1 gene are duplicated in ChrIV (B) and ChrXVI (C), respectively. Parent, Evo1, and Evo2 indicate strains Y560, Y1031, and Y1033, respectively.

FIGS. 9A-9C. The engineered respiration-deficient mutant strain adapted to xylose aerobically two independent flasks. The respiration-deficient Parent strain was cultured in three different flasks (A). Two different cultures adapted to xylose aerobically within 19 (B) and 18 (C) generations. The evolved strains (Evo1 and Evo2) were evolved from the respiration-deficient Parent (Y583) strain containing one copy of the XYL cassette with deletion mutations in HOG1, ISU1, GRE3, IRA2, and COX15. Evo1 and Evo2 indicate strains Y1031 and Y1033, respectively.

DETAILED DESCRIPTION

Figure 1A:
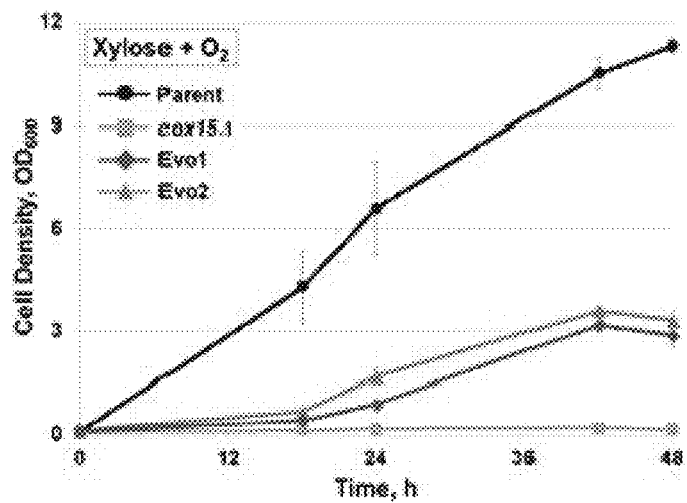
FIGS. 1A-1C. Adaptive laboratory evolution provided for engineered respiration-deficient yeast strains to ferment xylose into ethanol aerobically. The evolved (Evo1 and Evo2), respiration-deficient (cox15), and parent containing wild-type COX15 (Parent) strains were cultured aerobically in YPX medium. The evolved strains were evolved from the respiration-deficient strain. Average cell density (A), extracellular xylose (B), and ethanol (C) concentrations from independent triplicate experiments with SEM reported. Parent, cox15Δ, Evo1, and Evo2 indicate strains Y560, Y583, Y1031, and Y1033, respectively (Table 2).

Bottlenecks in the efficient conversion of xylose into cost-effective biofuels have limited the widespread use of plant lignocellulose as a renewable feedstock. The yeast *Saccharomyces cerevisiae* ferments glucose into ethanol with such high metabolic flux that it ferments high concentrations of glucose aerobically, a trait called the Crabtree-Warburg Effect. In contrast to glucose, most engineered *S. cerevisiae* strains do not ferment xylose at economically viable rates and yields, and they require respiration to achieve sufficient xylose metabolic flux and energy return for growth aerobically.

As disclosed herein, respiration-deficient *S. cerevisiae* strains were evolved to grow on and ferment xylose to ethanol aerobically, a trait analogous to the Crabtree-Warburg Effect for glucose. Through genome sequence comparisons and directed engineering, it was determined that duplications of genes encoding engineered xylose metabolism enzymes, as well as TKL1, a gene encoding a transketolase in the pentose phosphate pathway, were the causative genetic changes for the evolved phenotype. Reengineered duplications of these enzymes, in combination with deletion mutations in HOG1, ISU1, GRE3, and IRA2, increased the rates of aerobic and anaerobic xylose fermentation. Importantly, these genetic modifications function in another genetic background and they increase the rate and yield of xylose-to-ethanol conversion in industrially-relevant switchgrass hydrolysate, indicating that these specific genetic modifications may enable the sustainable production of industrial biofuels from yeast. A model is proposed for how key regulatory mutations prime yeast for aerobic xylose fermentation by lowering the threshold for overflow metabolism, allowing mutations to increase xylose flux and to redirect it into fermentation products.

Thus, the disclosure relates generally to methods and compositions for digesting lignocellulosic material and more particularly to methods that involve exposing the material to yeast variants, e.g., *S. cerevisiae* variants, having enhanced capacities for anaerobic and aerobic xylose fermentation, e.g., in industrially relevant lignocellulosic hydrolysates.

In a first aspect, provided herein is a recombinant yeast that has been genetically engineered to recombinantly express a xylose isomerase, a xyluokinase, a transaldolase and a transketolase. The recombinantly expressed xylose isomerase may be a native xylose isomerase. The recombinantly expressed xylose isomerase may be a non-native, e.g., from a different species, xylose isomerase. The recombinantly expressed xylulokinase may be a native xylulokinase. The recombinantly expressed xylulokinase may be a non-native xylulokinase. The recombinantly expressed transketolase may be a native transketolase. The recombinantly expressed trasnketolase may be a non-native transketolase. The recombinantly expressed transaldolase may be a native transaldolase. The recombinantly expressed transaldolase may be a non-native transaldolase. In one embodiment, there may be one, two, three or more copies of genes encoding the non-native enzymes. In one embodiment, there may be one, two, three or more additional copies of genes encoding the native enzymes, e.g., for a diploid, the recombinant yeast may have a total of three, four, five or more copies of the gene encoding the native enzyme.

In one embodiment, the recombinant yeast may exhibit reduced amounts of functional Isu1 polypeptide. In one embodiment, the recombinant yeast may exhibit reduced amounts of functional Hog1 polypeptide. In one embodiment, the recombinant yeast may exhibit reduced amounts of functional Ira2 polypeptide. In one embodiment, the recombinant yeast may exhibit reduced amounts of functional Gre3 polypeptide. In one embodiment, the recombinant yeast may exhibit reduced amounts of functional Cox15 polypeptide. The genetically engineered recombinant yeast is capable of increased aerobic xylose fermentation relative to a wild-type yeast or another recombinant yeast not exhibiting reduced amounts of functional Isu1 polypeptide, functional Hog1 polypeptide, functional Ira2 polypeptide, functional Gre3 polypeptide, or functional Cox15 polypeptide, or any combination thereof. Thus, the recombinant yeast may comprise a disabling mutation in a gene encoding Isu1 polypeptide. The disabling mutation may comprise a substitution of a tyrosine for the histidine at amino acid residue position 138 of SEQ ID NO:3. The recombinant yeast may further comprise a disabling mutation in a gene encoding Hog1 polypeptide and exhibit reduced amounts of functional Hog1 polypeptide. The disabling mutation in a gene encoding Isu1 may comprise a substitution of a tyrosine for the histidine at amino acid residue position 138 of SEQ ID NO:3, and the disabling mutation in the gene encoding Hog1 may comprise a deletion of the adenine at nucleotide position 844 of SEQ ID NO:7. The recombinant yeast may be of the genus *Saccharomyces*. The recombinant yeast may be of the species *Saccharomyces cerevisiae*. A portion of an extrachromosomal vector stably maintained in the recombinant yeast can comprise the disabling mutation. A nucleic acid sequence comprising the disabling mutation may be integrated into a chromosome of the recombinant yeast.

In another aspect, provided herein is a yeast inoculum comprising a recombinant yeast as provided herein and a culture medium.

In a further aspect, provided herein is a recombinant yeast that has been genetically engineered to recombinantly express a xylose isomerase, a xyluokinase, a transaldolase, and a transketolase. In one embodiment, the recombinant yeast exhibits reduced amounts of functional Isu1 and Hog1 polypeptides, and at least one of functional Gre3, Ira1, and Ira2 polypeptides, and optionally reduced amounts of Cox15. The recombinant yeast may be capable of increased anaerobic xylose fermentation relative to a wild-type yeast or another recombinant yeast not exhibiting reduced amounts of functional Isu1 and Hog1 polypeptides, and at least one of functional Gre3, Ira1, and Ira2 polypeptides. The recombinant yeast can comprise a disabling mutation in a gene encoding Isu1, a disabling mutation in a gene encoding Hog1, and at least one of a disabling mutation in a gene encoding Gre3, a disabling mutation in a gene encoding Ira1, and a disabling mutation in a gene encoding Ira2. The recombinant yeast may exhibit reduced amounts of functional Isu1, Hog1, Gre3, and Ira2 polypeptides and may be capable of increased anaerobic xylose fermentation relative to a wild-type yeast or another recombinant yeast not exhibiting reduced amounts of functional Isu1, Hog1, reE3, and/or Ira2 polypeptides. The disabling mutation in the gene encoding Isu1 can comprise a substitution of a tyrosine for the histidine at amino acid residue position 138 of SEQ ID NO:3; a disabling mutation in the gene encoding Hog1 can comprise a deletion of the adenine at nucleotide position 844 of SEQ ID NO:7; a disabling mutation in the gene encoding Gre3 can comprise a substitution of a threonine for the alanine at amino acid residue position 46 of SEQ ID NO:4; and a disabling mutation in the gene encoding Ira2 can comprise a substitution of a stop codon for the glutamate at amino acid residue at position 2927 of SEQ ID NO:2. The recombinant yeast may be of the genus *Saccharomyces*. The recombinant yeast may be of the species *Saccharomyces cerevisiae*. A portion of an extrachromosomal vector stably maintained in the recombinant yeast can comprise the disabling mutations. A nucleic acid sequence comprising the disabling mutations can be integrated into a chromosome of the recombinant yeast.

In another aspect, provided herein is a yeast inoculum comprising a recombinant yeast as provided herein and a culture medium.

In a further aspect, provided herein is a method of fermenting cellulosic material into ethanol. The method can comprise contacting under ethanol-producing conditions a recombinant yeast provided herein to cellulosic material for a period of time sufficient to allow fermentation of at least a portion of the cellulosic material into ethanol. The method can further comprise separating the ethanol from fermented cellulosic material. The method can further comprise hydrolyzing the cellulosic material to produce a hydrolysate comprising xylose; and contacting the recombinant yeast to the hydrolysate under conditions that permit fermentation. The cellulosic material can comprise a lignocellulosic biomass. The lignocellulosic biomass can comprise at least one material selected from the group consisting of agricultural residues, wood, municipal solid wastes, paper and pulp industry wastes, and herbaceous crops.

As can be appreciated, the present disclosure contemplates the use of recombinant yeast as described herein, including certain exemplary recombinant *Saccharomyces cerevisiae* strains specifically identified herein, for use in the fermentation of xylose-containing cellulosic materials and for production of ethanol or other biofuels and other bioproducts.

Compositions of the Disclosure

Efficient fermentation of cellulosic feedstock is an essential step in the production of biofuel from plant materials. While *S. cerevisiae* excels at fermentation of glucose from corn and sugar cane, the fermentation of renewable lignocellulosic biomass presents a significant challenge. Xylose, which is a pentose sugar and a major component of hemicellulose, can comprise almost 30% of total cell wall carbohydrate in grasses. Its conversion, along with glucose, into ethanol is important for any economically-viable cellulosic biofuel process. However, native *S. cerevisiae* cannot efficiently ferment xylose, as most strains have either lost or downregulated the activities of xylose catabolism proteins. Even when engineered to express the minimal enzymes from native xylose metabolizing organisms, *S. cerevisiae* is still unable ferment xylose from innocuous lab media at industrially-acceptable rates. However, several Ascomycete yeasts that both ferment and assimilate xylose have been identified, including *Pichia* stipites (*Scheffersomyces stipitis*) whose genome has been sequenced. The present disclosure is based, at least in part, on genetic modifications that permit substantially faster xylose fermentation under anaerobic conditions-conditions preferred for industrial ethanol production from plant biomass.

Accordingly, one aspect of the present disclosure relates to strains genetically engineered to be xylose-utilizing and ethanol-producing yeast strains. In particular, the present disclosure provides further genetic modifications to eukaryotic host cells that have been engineered to express xylose metabolism enzymes. Such further genetic modifications improve the efficiency of xylose metabolism in such host cells. In exemplary embodiments, modified host cells of the present disclosure are yeasts that have been additionally genetically engineered for enhanced anaerobic and/or aerobic xylose fermentation and increased ethanol production. The modified host cells are well-suited for producing a variety of fermentation products, including ethanol, in fermentation processes that use xylose or a combination of xylose and glucose as carbon sources.

As used herein, a "host cell" is a cell which has been transformed or transfected, or is capable of transformation or transfection by an exogenous polynucleotide sequence. A host cell that has been transformed or transfected may be more specifically referred to as a "recombinant host cell." A preferred host cell is a host cell that is naturally capable of alcoholic fermentation, preferably, anaerobic alcoholic fermentation. Host cells may also exhibit a high tolerance to ethanol, low pH, organic acids, and/or elevated temperatures. Such characteristics or activities of the host cell may be naturally present in the host cell or may be introduced or modified by genetic modification.

Exemplary host cells for the present disclosure include yeast cells, particularly yeast cells of the genus *Saccharomyces*. Preferred yeast species as host cells include *Saccharomyces cerevisiae, S. bulderi, S. barnetti, S. exiguus, S. uvarum, S. diastaticus, K. lactis, K. marxianus,* and *K fragilis*, of which yeast cells of the genus *Saccharomyces* and yeast cells of the species *Saccharomyces cerevisiae* are preferred. Yeasts of the genus *Saccharomyces* possess both a metabolic pathway and a fermentative pathway for respiration.

"Yeasts" are eukaryotic micro-organisms classified in the kingdom Fungi. Most reproduce asexually by budding, although some yeasts undergo sexual reproduction by meiosis. Yeasts are unicellular, although some species with yeast forms may become multi-cellular through the formation of a string of connected budding cells known as pseudohyphae, or false hyphae, as seen in most molds. Yeasts do not form a single taxonomic or phylogenetic grouping. The term "yeast" is often taken as a synonym for *Saccharomyces cerevisiae*, but the phylogenetic diversity of yeasts is illustrated by their assignment to two taxonomic classes of fungi, the ascomycetes and the basidiomycetes. As used herein, wild type yeast refers to a yeast strain designated GLBRCY0 (YB-210). GLBRCY0/YB-210 is a strain of *S. cerevisiae* that can be obtained from the ARS Culture Collection, National Center for Agricultural Utilization Research, Peoria, Ill., USA; under NRRL YB-210.

A suitable host yeast cell contains at least one native gene (a "xylose isomerase gene") that produces an active xylose isomerase enzyme that is capable of catalyzing the interconversion of D-xylose to D-xylulose. Xylose isomerase can also catalyze the interconversion of D-ribose to D-ribulose and D-glucose to D-fructose. The enzyme can be specific to the reduction of xylose or non-specific (i.e., capable of catalyzing the conversion of a range of pentose sugars). In some cases, a suitable host yeast cell is genetically engineered to contain an expression cassette containing *Clostridium phytofermentans* xylose isomerase (CphytoXylA), which can confer anaerobic xylose fermentation by *S. cerevisiae* with additional genetic modifications (see Brat et al., Applied Environmental Microbiol. 75:2304 (2009)), driven by the ScerTDH3 promoter. In exemplary embodiments, the expression cassette further comprises ScerTAL1, a Pentose Phosphate Pathway transaldolase enzyme that can improve xylose metabolism when overexpressed (see Ni et al., Applied Environmental Microbiol. 73:2061 (2007); Walfridsson et al., Applied Environmental Microbiol. 61:4184 (1995)), and SstipXyl3 driven by the ScerPGK1 and ScerTEF2 promoters, respectively. For example, the host yeast cell can comprise a TAL1-XylA-XYL3 gene expression cassette.

Recombinant yeast of the present disclosure can further comprise genetic modifications intended to delete or disrupt genes encoding certain polypeptides. By "delete or disrupt", it is meant that the entire coding region of the gene is eliminated (deletion), or the gene or its promoter and/or terminator region is modified (such as by deletion, insertion, or mutation) so that the gene no longer produces an active enzyme, or produces an enzyme with severely reduced activity. The deletion or disruption can be accomplished by genetic engineering methods, forced evolution or mutagenesis, and/or selection or screening.

Recombinant yeast of the present disclosure may comprise genetic modifications that cause reduced levels of, for example, functional Isu1, Gre3, Ira2, Ira1, Cox15, and/or Hog1 polypeptides, or any combination thereof. Isu1 is a polypeptide for mitochondrial iron-sulfur (Fe—S) protein biogenesis. Gre3 is an aldolase enzyme. Hog1 is a mitogen-activated protein (MAP) kinase involved in osmoregulation. Ira1 and Ira2 are Ras GTPase activating proteins that act as a negative regulators of cyclic AMP (cAMP) signaling. Consistent with their role as negative regulators of the Ras-cAMP pathway, disruption of either Ira2 or Ira1 decreases the rate at which Ras proteins hydrolyze GTP to GDP and increases intracellular cAMP levels (Tanaka et al., Mol Cell Biol 9(2):757-68 (1990)). The amino acid sequence of an exemplary Ira2 is set forth as SEQ ID NO:2. The amino acid sequence of an exemplary Gre3 is set forth as SEQ ID NO:4, respectively. The amino acid sequence of an exemplary Isu1 is set forth as SEQ ID NO:3. The amino acid sequence of an exemplary Hog1 is set forth as SEQ ID NO:5.

In some cases, a recombinant yeast of the present disclosure may comprise a disabling mutation that substitutes a threonine amino acid residue for the alanine located amino acid residue position 46 of SEQ ID NO:4, whereby the yeast exhibits a reduced amount of functional Gre3 polypeptide. In other cases, a recombinant yeast of the present disclosure may comprise a disabling mutation that substitutes a stop codon for the glutamate at amino acid residue at position 2927 of SEQ ID NO:2, whereby the yeast exhibits a reduced amount of functional Ira2 polypeptide. Alternatively, a recombinant yeast may comprise a disabling mutation Ira1, whereby the recombinant yeast exhibits a reduced amount of functional Ira1. In other cases, a recombinant yeast of the present disclosure may comprise a disabling mutation that substitutes a tyrosine for the histidine at amino acid residue position 138 of SEQ ID NO:3, whereby the yeast exhibits a reduced amount of functional Isu1 polypeptide. In further cases, a recombinant yeast of the present disclosure may comprise a disabling mutation that deletes an adenine nitrogenous base at nucleotide position 844, e.g., SEQ ID NO:7, of a sequence that encodes SEQ ID NO:5, whereby the deletion causes a codon frame-shift and the yeast exhibits a reduced amount of functional HOG1 polypeptide.

In exemplary embodiments, a recombinant yeast of the disclosure comprises a disabling mutation at each of loci ISU1, GRE3, HOG1, COX15, and IRA2, whereby the mutations result in reduced amounts of functional Isu1, Gre3, Hog1, Cox15 and Ira2 polypeptides, respectively. In some cases, the disabling mutations include a missense mutation in the S. cerevisiae gene encoding Isu1, a missense mutation in the gene encoding Gre3, an aldolase enzyme, a missense mutation in the gene encoding Ira2, and a codon frame-shift mutation in the gene encoding Hog1. Deletion of GRE3 was previously shown to improve xylose fermentation in xylose isomerase-engineered S. cerevisiae strains (Traff et al., Applied and Environmental Microbiol. 67:5668 (2001)). In exemplary embodiments, a recombinant yeast of the present disclosure comprises a disabling mutation at the GRE3 locus that substitutes a threonine for the alanine at amino acid residue position 46 of SEQ ID NO:4; a disabling mutation at the IRA2 locus that substitutes a stop codon for the glutamate at amino acid residue at position 2927 of SEQ ID NO:2; a disabling mutation at the ISU1 locus that substitutes a tyrosine for the histidine at amino acid residue position 138 of SEQ ID NO:3; and a disabling mutation at the HOG1 locus that deletes an adenine nitrogenous base at nucleotide position 844 of a nucleotide sequence, e.g., SEQ ID NO:7, that encodes SEQ ID NO:5. A disabling mutation in the gene encoding COX15 may be accomplished by deleting all or a portion of that gene.

Genetically modified yeasts of the present disclosure containing genetic modifications that reduce or disrupt expression of one or more of Isu1, Hog1, Gre3, Ira2, Cox15, and/or Ira1 polypeptides are useful to ferment xylose pentose sugars to desirable fermentation products such as ethanol. For example, genetically engineered yeast comprising disabling mutations at three loci (e.g., isu1Δhog1Δgre3Δ; isu1Δhog1Δira2Δ; isu1Δhog1Δira1Δ) or four loci (e.g., isu1Δhog1Δgre3Δ, and either ira1Δ or ira2Δ) exhibit substantially faster anaerobic xylose fermentation relative to controls. Anaerobic xylose fermentation was fastest for genetically engineered yeast comprising mutations in four loci (isu1Δhog1Δgre3Δ, and either ira1Δ or ira2Δ). Recombinant yeast may not comprise null mutations at an IRA1 locus and an IRA2 locus since the double mutation is lethal. For aerobic xylose metabolism, a genetically engineered yeast comprises genetic modifications that reduces or disrupt Isu1 polypeptide expression. Such a genetically engineered yeast may have mutations at additional loci.

It is contemplated that certain additional genetic modifications may produce other desirable characteristics and/or to enable the yeast cell to produce certain products at industrially-acceptable levels.

Genetic modification of the host cell can be accomplished in one or more steps via the design and construction of appropriate vectors and transformation of the host cell with those vectors. Nucleic acid constructs useful in the disclosure may be prepared in conventional ways, by isolating the desired genes from an appropriate host, by synthesizing all or a portion of the genes, or combinations thereof. Similarly, the regulatory signals, the transcriptional and translational initiation and termination regions, may be isolated from a natural source, be synthesized, or combinations thereof. The various fragments may be subjected to endonuclease digestion (restriction), ligation, sequencing, in vitro mutagenesis, primer repair, or the like. The various manipulations are well known in the literature and will be employed to achieve specific purposes.

The various nucleic acids and/or fragments thereof may be combined, cloned, isolated and sequenced in accordance with conventional ways. Standard techniques of molecular biology, microbiology, recombinant DNA, and immunology, which are within the skill of the art, are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

The nucleotides which occur in the various nucleotide sequences appearing herein have their usual single-letter designations (A, G, T, C or U) used routinely in the art. In the present specification and claims, references to Greek letters may either be written out as alpha, beta, etc. or the corresponding Greek letter symbols (e.g., α, β, etc.) may sometimes be used.

The term "isolated nucleic acid" used in the specification and claims means a nucleic acid isolated from its natural environment or prepared using synthetic methods such as those known to one of ordinary skill in the art. Complete purification is not required in either case. The nucleic acids of the disclosure can be isolated and purified from normally associated material in conventional ways such that in the purified preparation the nucleic acid is the predominant species in the preparation. At the very least, the degree of purification is such that the extraneous material in the preparation does not interfere with use of the nucleic acid of the disclosure in the manner disclosed herein. The nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene. Specifically excluded from this definition are nucleic acids present in mixtures of clones, e.g., as those occurring in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine, as described in a preceding definition.

After each manipulation, the DNA fragment or combination of fragments (polynucleotides) may be inserted into the cloning vector, the vector transformed into a cloning host, e.g., E. coli, the cloning host grown up, lysed, the plasmid isolated and the fragment analyzed by restriction analysis, sequencing, combinations thereof, or the like. "Polynucleotide(s)" generally refers to any polyribonucleotide or polydeoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

Targeted integration can be accomplished by designing a vector having regions that are homologous to the upstream (5'-) and downstream (3'-) flanks of the target gene. Either of both of these regions may include a portion of the coding region of the target gene. The gene cassette (including associated promoters and terminators if different from those of the target gene) and selection markers (with associated promoters and terminators as may be needed) can reside on a vector between the regions that are homologous to the upstream and downstream flanks of the target gene. Targeted cassette insertion can be verified by any appropriate method such as, for example, PCR. A host cell may be transformed according to conventional methods that are known to practitioners in the art. Electroporation and/or chemical (such as calcium chloride- or lithium acetate-based) transformation methods can be used. The DNA used in the transformations can either be cut with particular restriction enzymes or used as circular DNA. Methods for transforming yeast strains are described in WO 99/14335, WO 00/71738, WO 02/42471, WO 03/102201, WO 03/102152 and WO 03/049525; these methods are generally applicable for transforming host cells in accordance with this disclosure. Other methods for transforming eukaryotic host cells are well known in the art such as from standard handbooks, such as Sambrook and Russel (2001) "Molecular Cloning: A Laboratory Manual (3rd edition)," Cold Spring Harbor Laboratory, Cold Spring Harbor Laboratory Press, or F. Ausubel et al., eds., "Current protocols in molecular biology," Green Publishing and Wiley Interscience, New York (1987).

In another aspect, compositions of the present disclosure include yeast inoculums comprising recombinant yeast as provided herein. A yeast inoculum of the present disclosure can comprise a recombinant yeast as provided herein and (b) a culture medium. In exemplary embodiments, the recombinant yeast is S. cerevisiae and the culture medium is a liquid culture medium. Yeast inocula of the present disclosure include large-scale preparations of sufficient quantities of viable yeast cells for use in, for example, xylose fermentation and other industrial ethanol-producing methods. A yeast inoculum of the present disclosure can be contacted to cellulosic material for xylose fermentation.

Methods of the Disclosure

The methods provided by the present disclosure involve the incorporation of genetic modifications into a host organism, e.g., incorporating genes encoding certain polypeptides into a single host organism, and the use of those organisms to convert xylose to ethanol. In particular, the present disclosure provides methods of fermenting cellulosic material comprising the 5-carbon sugar xylose under anaerobic or aerobic conditions, where the method comprises use of a recombinant yeast.

In exemplary embodiments, recombinant yeast of the present disclosure are used to make a useful fuel (e.g., ethanol) or plant material-derived chemical feedstock by converting xylose and other sugars under appropriate fermentation conditions. The sugars can come from a variety of sources including, but not limited to, cellulosic material. The cellulosic material can be lignocellulosic biomass. As used herein, the term "lignocellulosic biomass" refers to any materials comprising cellulose, hemicellulose, and lignin, wherein the carbohydrate polymers (cellulose and hemicelluloses) are tightly bound to the lignin. Generally, lignocellulosic material for making ethanol is feedstock such as corn stover, which consists of the stems, cobs, and leaves from the corn plants (i.e., the non-grain material). Corn stover is typically shredded by mechanical means and incorporated by tillage into topsoil for decomposition. In addition to lignocellulosic ethanol production from corn stover, other feedstocks such as sorghum, wheat, or another grain can be used. In some cases, lignocellulosic biomass comprises material selected from the group consisting of materials that comprise at least 75% cellulose, cellulose/hemicelluloses, xylose, biomass, and chitin. In other cases, the lignocellulosic biomass comprises at least one material selected from the group consisting of agricultural residues, wood, municipal solid wastes, paper and pulp industry wastes, and herbaceous crops. As used herein, the term "biomass" refers to a renewable energy source, is biological material from living or recently living organisms. As an energy source, biomass can either be used directly, or converted into other energy products such as biofuel. Biomass includes plant or animal matter that can be converted into fibers or other industrial chemicals, including biofuels. Industrial biomass can be grown from numerous types of plants, including miscanthus, switchgrass, hemp, corn, poplar, willow, sorghum, sugarcane, bamboo, and a variety of tree species, ranging from eucalyptus to oil palm (palm oil). Thus, biomass can include wood biomass and non-wood biomass.

In some cases, cellulosic material is contacted with one or more of the genetically engineered yeasts disclosed herein (e.g., a yeast strain genetically modified to exhibit reduced amounts of functional Isu1, Gre3, Hog1, Ira1, Cox15, and/or Ira2 polypeptides) under anaerobic or aerobic conditions. For example, a method of fermenting cellulosic material can comprise contacting under anaerobic conditions a recombinant yeast as provided herein to cellulosic material for a period of time sufficient to allow fermentation of at least a portion of the cellulosic material. In exemplary embodiments, a recombinant yeast used according to the methods provided herein is *Saccharomyces cerevisiae*.

The fermentation process may be an aerobic or an anaerobic fermentation process. Anaerobic fermentation is herein defined as a fermentation process run in the absence of oxygen or in which substantially no oxygen is consumed, preferably less than 5, 2.5 or 1 mmol/L/h, e.g., 0 mmol/L/h is consumed (i.e., oxygen consumption is not detectable), and where organic molecules serve as both electron donor and electron acceptors. In the absence of oxygen, NADH produced in glycolysis and biomass formation cannot be oxidized by oxidative phosphorylation.

In some cases, the method can include a first hydrolyzation step. For example, when cellulosic material is used in the methods disclosed herein, the material can be hydrolyzed to produce a hydrolysate comprising xylose, which is subsequently contacted to one or more recombinant yeasts of the present disclosure. As used herein, the term "hydrolysate" refers to a fermentable sugar-containing product produced from cellulosic material (e.g., biomass), typically through pretreatment and saccharification processes. In general, cellulosic material is pretreated using thermal, physical, and/or chemical treatments, and saccharified enzymatically. Physical and chemical treatments may include grinding, milling, cutting, base treatment such as with ammonia or NaOH, and acid treatment. In some cases, plant biomass can be pretreated using AFEX™. While highly effective at pretreating grasses for enzymatic hydrolysis, AFEX™ pretreatment generates diverse inhibitory compounds from corn stover that impair xylose fermentation (Schwalbach et al., Applied Environ. Microbiol. 78:3442 (2012); Koppram et al., Biotechnol. Biofuels 5:32 (2012); Lau & Dale, PNAS USA 106:1368 (2009)). The inhibitory compounds are degradation products derived from plant cell walls such as hemicellulose and lignin-derived acetate and aromatic molecules.

Enzymatic saccharification typically makes use of an enzyme composition or blend to break down cellulose and/or hemicellulose and to produce a hydrolysate containing 6-carbon sugars (e.g., glucose) and 5-carbon sugars (e.g., xylose, arabinose). For review of saccharification enzymes, see Lynd et al., Microbiol. Mol. Biol. Rev. 66:506-577 (2002). Saccharification enzymes may be obtained commercially. In some cases, saccharification enzymes may be produced using recombinant microorganisms that have been engineered to express one or more saccharifying enzymes.

In some cases, methods of the present disclosure further comprise an ethanol separation or extraction step. Following conversion of sugars into ethanol, the ethanol can be separated from a fermentation culture using, for example, a standard distillation method or by filtration using membranes or membrane systems known in the art. Methods of separating or extracting are not restricted to those disclosed herein.

Methods of the present disclosure can be conducted continuously, batch-wise, or some combination thereof.

In another aspect, provided herein are methods for producing fuels and chemical feedstocks from glycerol (or glycerin). Glycerol is a by-product of biodiesel production, which, using a recombinant yeast of the present disclosure, could be further converted to a fuel or chemical feedstock such as, for example, ethanol, lactic acid, isobutanol, and propanediol. In some cases, a method of converting glycerol to ethanol can comprise contacting glycerol to one or more of the genetically engineered yeasts disclosed herein (e.g., a yeast strain genetically modified to exhibit reduced amounts of functional Isu1, Gre3, Hog1, Ira1, Cox15, and/or Ira2 polypeptides) under appropriate fermentation conditions. In exemplary embodiments, methods are provided for producing lactic acid from glycerol. In such cases, the method comprises contacting under anaerobic conditions a recombinant yeast provided herein to glycerol for a period of time sufficient to allow fermentation of at least a portion of the glycerol into lactic acid. Lactic acid is in high demand as a chemical feedstock for the biodegradable plastic known as polylactic acid (PLA), a biopolymer that is useful in a variety of applications including packaging material and medical devices (e.g., surgical sutures, orthopedic implants). The raw materials to manufacture lactic acid are expensive and limit use of PLA. In other cases, the method of converting glycerol into a useful fuel comprises contacting under anaerobic conditions a recombinant yeast as provided herein to glycerol for a period of time sufficient to allow fermentation of at least a portion of the glycerol into ethanol or butanol.

In exemplary embodiments, a recombinant yeast used according to the methods provided herein is *Saccharomyces cerevisiae* (*S. cerevisiae*). Following conversion of glycerol into ethanol, the fuel or chemical feedstock can be separated from a fermentation culture using, for example, a standard distillation method or by filtration using membranes or membrane systems known in the art. Methods of separating or extracting are not restricted to those disclosed or exemplified herein.

Articles of Manufacture

In a further aspect, the present disclosure provides an article of manufacture containing any one or more of the recombinant yeasts disclosed herein is provided. An article of manufacture can contain one of the microorganisms disclosed herein (e.g., one or more of the yeast strains), or an article of manufacture can contain two or more of the microorganisms disclosed herein. Articles of manufacture disclosed herein also can include, for example, components necessary for growth of the particular microorganism(s).

It is understood that this disclosure is not limited to the particular methodology, protocols, materials, and reagents described, as these may vary. It is also to be understood that the terminology used herein is for the purpose of describing particular embodiments only, and is not intended to limit the scope of the present disclosure, which will be limited only by the appended claims.

It must be noted that as used herein and in the appended claims, the singular forms "a," "an," and "the" include plural reference unless the context clearly dictates otherwise. As well, the terms "a" (or "an"), "one or more" and "at least one" can be used interchangeably herein. It is also to be noted that the terms "comprising," "including," and "having" can be used interchangeably.

Exemplary Sequences

Exemplary xylose isomerase sequences for use in the host cells and methods of the disclosure include but are not limited to (SEQ ID NO: 10)
mknyfpnvpe vkyegpnstn pfafkyydae rivagktmke hcrfalswwh tlcaggadpf gvttmdrsyg nitdpmefak akvdagfelm tklgieyfcf hdadiapege nfeeskknlf -continued

```
vivdyikekm dqtgikllwg tannfghprf mhgastscna
dvfayaaaki knaldatikl ggkgyvfwgg regyetllnt
dlgleldnma rlmkmaveyg rangfdgdfy iepkpkeptk
hqydfdtatv lgflrkygle kdfkmniean hatlaghtfe
helalarvng vfgsvdanqg dpnlgwdtdq fptdvhsatl
amlevlkagg ftngglnfda kvrrgsfefd diaygyiagm
dtfalglika aeiiedgria kfvedryasy ktgigkaivd
gttsleeleq yvlthnepvm qsgrqevles ivnnilfr,
                                        (SEQ ID NO: 11)
mknyfpnvpe vkyegpnstn pfafkyydan kvvagktmke
hcrfalswwh tlcaggadpf gvttmdrtyg nitdpmelak
akvdagfelm tklgieffcf hdadiapegd tfeeskknlf
eivdyikekm dqtgikllwg tannfshprf mhgastscna
dvfayaaaki knaldatikl ggkgyvfwgg regyetllnt
dlgleldnma rlmkmaveyg rangfdgdfy iepkpkeptk
hqydfdtatv laflrkygle kdfkmniean hatlaghtfe
helamarvng afgsvdanqg dpnlgwdtdq fptdvhsatl
amlevlkagg ftngglnfda kvrrgsfefd diaygyiagm
dtfalglika aeiiddgria kfvddryasy ktgigkaivd
gttsleeleq yvlthsepvm qsgrqevlet ivnnilfr,
                                        (SEQ ID NO: 12)
MKNYFPNVPEVKYEGPNSTNPFAFKYYDANKVVAGKTMKEHCRFALSWWH
TLCAGGADPFGVTTMDRTYGNITDPMELAKAKVDAGFELMTKLGIEFFCF
HDADIAPEGDTFEESKKNLFEIVDYIKEKMDQTGIKLLWGTANNFSHPRF
MHGASTSCNADVFAYAAAKIKNALDATIKLGGKGYVFWGGREGYETLLNT
DLGLELDNMARLMKMAVEYGRANGFDGDFYIEPKPKEPTKHQYDFDTATV
LAFLRKYGLEKDFKMNIEANHATLAGHTFEHELAMARVNGAFGSVDANQG
DPNLGWDTDQFPTDVHSATLAMLEVLKAGGFTNGGLNFDAKVRRGSFEFD
DIAYGYIAGMDTFALGLIKAAEIIDDGRIAKFVDDRYASYKTGIGKAIVD
GTTSLEELEQYVLTHSEPVMQSGRQEVLETIVNNILFR,
``` or a polypeptide having at least 80%, 82%, 85%, 86%, 88%, 90%, 92%, 94%, 95%, 97%, 98% or 99% amino acid sequence identity thereto.

Exemplary xylulokinase sequences for use in the host cells and methods of the disclosure include but are not limited to

```
                                        (SEQ ID NO: 13)
mtttpfdapd klflgfdlst qqlkiivtde nlaalktynv
efdsinssvq kgviaindei skgaiispvy mwldaldhvf
edmkkdgfpf nkvvgisgsc qqhgsvywsr taekvlseld
aesslssqmr saftfkhapn wqdhstgkel eefervigad
aladisgsra hyrftglqir klstrfkpek ynrtarislv
ssfvasvllg ritsieeada cgmnlydiek refneellai
aagvhpeldg veqdgeiyra ginelkrklg pvkpityese
gdiasyfvtr ygfnpdckiy sftgdnlati islplapnda
lislgtsttv liitknyaps sqyhlfkhpt mpdhymgmic
ycngslarek vrdevnekfn vedkkswdkf neildkstdf
nnklgiyfpl geivpnaaaq ikrsvlnskn eivdvelgdk
nwqpeddvss ivesqtlscr lrtgpmlsks gdssassssas
pqpegdgtdl hkvyqdlvkk fgdlytdgkk qtfesltarp
nrcyyvggas nngsiirkmg silapvngny kvdipnacal
ggaykaswsy eceakkewig ydqyinrlfe vsdemnsfev
kdkwleyang vgmlakmese lkh,
                                        (SEQ ID NO: 14)
mtttpfdapd klflgfdlst qqlkiivtde nlaalktynv
efdsinssvq kgviaindei skgaiispvy mwldaldhvf
edmkkdgfpf nkvvgisgsc qqhgsvywsr taekvlseld
aesslssqmr saftfkhapn wqdhstgkel eefervigad
aladisgsra hyrftglqir klstrfkpek ynrtarislv
ssfvasvllg ritsieeada cgmnlydiek refneellai
aagvhpeldg veqdgeiyra ginelkrklg pvkpityese
gdiasyfvtr ygfnpdckiy sftgdnlati islplapnda
lislgtsttv liitknyaps sqyhlfkhpt mpdhymgmic
ycngslarek vrdevnekfn vedkkswdkf neildkstdf
nnklgiyfpl geivpnaaaq ikrsvlnskn eivdvelgdk
nwqpeddvss ivesqtlscr lrtgpmlsks gdssassssas
pqpegdgtdl hkvyqdlvkk fgdlytdgkk qtfesltarp
nrcyyvggas nngsiirkmg silapvngny kvdipnacal
ggaykaswsy eceakkewig ydqyinrlfe vsdemnsfev
kdkwleyang vgmlakmese lkh,
                                        (SEQ ID NO: 15)
mtttpfdapd klflgfdlst qqlkiivtde nlaalktynv
efdsinssvq kgviaindei skgaiispvy mwldaldhvf
edmkkdgfpf nkvvgisgsc qqhgsvywsr taekvlseld
aesslssqmr saftfkhapn wqdhstgkel eefervigad
aladisgsra hyrftglqir klstrfkpek ynrtarislv
ssfvasvllg ritsieeada cgmnlydiek refneellai
aagvhpeldg veqdgeiyra ginelkrklg pvkpityese
gdiasyfvtr ygfnpdckiy sftgdnlati islplapnda
lislgtsttv liitknyaps sqyhlfkhpt mpdhymgmic
ycngslarek vrdevnekfn vedkkswdkf neildkstdf
nnklgiyfpl geivpnaaaq ikrsvlnskn eivdvelgdk
nwqpeddvss ivesqtlscr irtgpmlsks gdssassssas
pqpegdgtdl hkvyqdlvkk fgdlftdgkk qtfesltarp
```
nrcyyvggas nngsiixkmg silapvngny kvdipnacal ggaykaswsy eceakkewig ydqyinrlfe vsdemnsfev kdkwleyang vgmlakmese lkh, (SEQ ID NO: 16)
MTTTPFDAPDKLFLGFDLSTQQLKIIVTDENLAALKTYNVEFDSINSSVQ

KGVIAINDEISKGAIISPVYMWLDALDHVFEDMKKDGFPFNKVVGISGSC

QQHGSVYWSRTAEKVLSELDAESSLSSQMRSAFTFKHAPNWQDHSTGKEL

EEFERVIGADALADISGSRAHYRFTGLQIRKLSTRFKPEKYNRTARISLV

SSFVASVLLGRITSIEEADACGMNLYDIEKREFNEELLAIAAGVHPELDG

VEQDGEIYRAGINELKRKLGPVKPITYESEGDIASYFVTRYGFNPDCKIY

SFTGDNLATIISLPLAPNDALISLGTSTTVLIITKNYAPSSQYHLFKHPT

MPDHYMGMICYCNGSLAREKVRDEVNEKFNVEDKKSWDKFNEILDKSTDF

NNKLGIYFPLGEIVPNAAAQIKRSVLNSKNEIVDVELGDKNWQPEDDVSS

IVESQTLSCRLRTGPMLSKSGDSSASSSASPQPEGDGTDLHKVYQDLVKK

FGDLYTDGKKQTFESLTARPNRCYYVGGASNNGSIIRKMGSILAPVNGNY

KVDIPNACALGGAYKASWSYECEAKKEWIGYDQYINRLFEVSDEMNSFEV

KDKWLEYANGVGMLAKMESELKH, or a polypeptide having at least 80%, 82%, 85%, 86%, 88%, 90%, 92%, 94%, 95%, 97%, 98% or 99% amino acid sequence identity thereto.

Exemplary transketolase (TKL) sequences for use in the host cells and methods of the disclosure include but are not limited to (SEQ ID NO: 17)
mtqftdidkl avstirilav dtvskansgh pgaplgmapa ahvlwsqmrm nptnpdwinr drfvlsngha vallysmlhl tgydlsiedl kqfrqlgsrt pghpefelpg vevttgplgq gisnavgmam aqanlaatyn kpgftlsdny tyvflgdgcl qegisseass laghlklgnl iaiyddnkit idgatsisfd edvakryeay gwevlyveng nedlagiaka iaqaklskdk ptlikmttti gygslhagsh svhgaplkad dvkqlkskfg fnpdksfvvp qevydhyqkt ilkpgveann kwnklfseyq kkfpelgael arrlsgqlpa nwesklptyt akdsavatrk lsetvledvy nqlpeliggs adltpsnltr wkealdfqpp ssgsgnysgr yirygireha mgaimngisa fganykpygg tflnfvsyaa gavrlsalsg hpviwvathd sigvgedgpt hqpietlahf rslpniqvwr padgnevsaa yknsleskht psiialsrqn lpqlegssie saskggyvlq dvanpdiilv atgsevslsv eaaktlaakn ikarvvslpd fftfdkqple yrlsvlpdnv pimsvevlat tcwgkyahqs fgidrfgasg kapevfkffg ftpegvaera qktiafykgd klisplkkaf, (SEQ ID NO: 18)
MTQFTDIDKLAVSTIRILAVDTVSKANSGHPGAPLGMAPAAHVLWSQMRM

NPTNPDWINRDRFVLSNGHAVALLYSMLHLTGYDLSIEDLKQFRQLGSRT

PGHPEFELPGVEVTTGPLGQGISNAVGMAMAQANLAATYNKPGFTLSDNY

TYVFLGDGCLQEGISSEASSLAGHLKLGNLIAIYDDNKITIDGATSISFD

EDVAKRYEAYGWEVLYVENGNEDLAGIAKAIAQAKLSKDKPTLIKMTTTI

GYGSLHAGSHSVHGAPLKADDVKQLKSKFGFNPDKSFVVPQEVYDHYQKT

ILKPGVEANNKWNKLFSEYQKKFPELGAELARRLSGQLPANWESKLPTYT

AKDSAVATRKLSETVLEDVYNQLPELIGGSADLTPSNLTRWKEALDFQPP

SSGSGNYSGRYIRYGIREHAMGAIMNGISAFGANYKPYGGTFLNFVSYAA

GAVRLSALSGHPVIWVATHDSIGVGEDGPTHQPIETLAHFRSLPNIQVWR

PADGNEVSAAYKNSLESKHTPSIIALSRQNLPQLEGSSIESASKGGYVLQ

DVANPDIILVATGSEVSLSVEAAKTLAAKNIKARVVSLPDFFTFDKQPLE

YRLSVLPDNVPIMSVEVLATTCWGKYAHQSFGIDRFGASGKAPEVFKFFG

FTPEGVAERAQKTIAFYKGDKLISPLKKAF, or a polypeptide having at least 80%, 82%, 85%, 86%, 88%, 90%, 92%, 94%, 95%, 97%, 98% or 99% amino acid sequence identity thereto.

Exemplary transaldolase (Tal) sequences for use in the host cells and methods of the disclosure include but are not limited to (SEQ ID NO: 19)
msepaqkkqk vannsleqlk asgtvvvadt gdfgsiakfq pqdsttnpsl ilaaakqpty aklidvavey gkkhgkttee qvenavdrll vefgkeilki vpgrvstevd arlsfdtqat iekarhiikl feqegvsker vlikiastwe giqaakelee kdgihcnltl lfsfvqavac aeaqvtlisp fvgrildwyk sstgkdykge adpgvisvkk iynyykkygy ktivmgasfr stdeiknlag vdyltispal ldklmnstep fprvldpvsa kkeagdkisy isdeskfrfd lnedamatek lsegirkfsa divtlfdlie kkvta, (SEQ ID NO: 20)
MSEPAQKKQKVANNSLEQLKASGTVVVADTGDFGSIAKFQPQDSTTNPSL

ILAAAKQPTYAKLIDVAVEYGKKHGKTTEEQVENAVDRLLVEFGKEILKI

VPGRVSTEVDARLSFDTQATIEKARHIIKLFEQEGVSKERVLIKIASTWE

GIQAAKELEEKDGIHCNLTLLFSFVQAVACAEAQVTLISPFVGRILDWYK

SSTGKDYKGEADPGVISVKKIYNYYKKYGYKTIVMGASFRSTDEIKNLAG

VDYLTISPALLDKLMNSTEPFPRVLDPVSAKKEAGDKISYISDESKFRFD

LNEDAMATEKLSEGIRKFSADIVTLFDLIEKKVTA, or a polypeptide having at least 80%, 82%, 85%, 86%, 88%, 90%, 92%, 94%, 95%, 97%, 98% or 99% amino acid sequence identity thereto.

Exemplary Ira2 sequences for use, e.g., to decrease or disable expression, in the host cells and methods of the disclosure include but are not limited to (SEQ ID NO: 2)

```
msqptknkkk ehgtdskssr mtrtlvnhil ferilpilpv
esnlstysev eeyssfiscr svlinvtvsr danamvegtl
eliesllqgh eiisdkgssd viesiliilr llsdaleynw
qnqeslhynd isthvehdqe qkyrpklnsi lpdyssthsn
gnkhffhqsk pqalipelas kllescaklk fntrtlqilq
nmishvhgni lttlsssilp rhksyltrhn hpshckmids
tlghilrfva asnpseyfef irksvqvpvt qththshshs
hslpssvyns ivphfdlfsf iylskhnfkk yleliknlsv
tlrktiyhcl llhysakaim fwimarpaey yelfnllkdn
nnehskslnt lnhtlfeeih stfnvnsmit tnqnahqgss
spsssspssp pssssdnnn qniiakslsr qlshhqsyiq
qqserklhss wttnsqssts lssststnstt tdfsthtqpg
eydpslpdtp tmsnitisas sllsqtptpt tqlqqrlnsa
aaaaaaaasp snstptgyta eqqsrasyda hktghtgkdy
dehflsvtrl dnvlelythf ddtevlphts vlkflttltm
fdidlfneln atsfkyipdc tmhrpkerts sfnntahetg
sektsgikhi tqglkkltsl psstkktvkf vkmllrnlng
nqavsdvall dtmrallsff tmtsavflvd rnlpsvlfak
rlipimgtnl svgqdwnski nnslmvclkk nsttfvqlql
iffssaiqfd helllarlsi dtmannlnmq klclytegfr
iffdipskke lrkaiavkis kffktlfsii adillqefpy
fdeqitdiva sildgtiine ygtkkhfkgs spslcsttrs
rsgstsqssm tpvsplgldt dicpmntlsl vgsstsrnsd
nvnslnsspk nlssdpylsh lvaprarhal ggpssiirnk
ipttltsppg teksspvqrp qtesisatpm aitnstplss
aafgirsplq kirtrrysde slgkfmkstn nyiqehlipk
dlneatlqda rriminifsi fkrpnsyfii phninsnlqw
vsqdfrnimk pifvaivspd vdlqntaqsf mdtllsnvit
ygesdenisi egyhllcsyt vtlfamglfd lkinnekrqi
llditvkfmk vrshlagiae ashhmeyisd sekltfplim
gtvgralfvs lyssqqkiek tlkiayteyl sainfherni
ddadktwvhn iefveamchd nyttsgsiaf qrrtrnnilr
fatipnaill dsmrmiykkw htythsksle kqerndfrnf
agilaslsgi lfinkkilqe mypylldtvs elkknidsfi
skqcqwlnyp dlltrensrd ilsvelhpls fnllfnnlrl
klkelacsdl sipenessyv lleqiikmlr tilgrdddny
vmmlfsteiv dlidlltdei kkipaycpky lkaiiqmtkm
fsalqhsevn lgvknhfhvk nkwirqitdw fqvsiareyd
fenlskplke mdlvkrdmdi lyidtaieas taiayltrht
fleippaasd pelsrsrsvi fgfyfnilmk glekssdrdn
ypvflrhkms vlndnvilsl tnlsntnvda slqftlpmgy
sgnrnirnaf levfinivtn yrtytaktdl gkleaadkfl
rytiehpqls sfgaavcpas didayaagli nafetrnath
ivvaqlikne iekssrptdi lrrnscatrs lsmlarskgn
eylirtlqpl lkkiiqnrdf feieklkped sdaerqielf
vkymnelles isnsvsyfpp plfyicqniy kvacekfpdh
aiiaagsfvf lrffcpalvs pdseniidis hlsekrtfis
lakviqnian gsenfsrwpa lcsqkdflke csdrifrfla
elcrtdrtid iqvrtdptpi afdyqflhsf vylyglevrr
nvlneakhdd gdidgddfyk ttflliddvl gqlgqpkmef
sneipiyire hmddypelye fmnrhafrni etstayspsv
hestssegip iitltmsnfs drhvdidtva ykflqiyari
wttkhcliid ctefdeggld mrkfislvmg llpevapknc
igcyyfnvne tfmdnygkcl dkdnvyvssk iphyfinsns
deglmksvgi tgqglkvlqd irvslhditl ydekrnrftp
vslkigdiyf qvlhetprqy kirdmgtlfd vkfndvyeis
rifevhvssi tgvaaeftvt fqderrlifs spkyleivkm
fyyaqirles eyemdnnsst sspnsnnkdk qqkertkllc
hlllvsligl fdeskkmkns synliaatea sfglnfgshf
hrspevyvpe dtttflgvig kslaesnpel taymfiyvle
alknnviphv yiphticgls ywipnlyqhv yladdeegpe
nishifrili rlsvretdfk avymqyvwll llddgrltdi
ivdevinhal erdsenrdwk ktislltvlp ttevanniiq
kilakirsfl pslkleamtq swseltilvk isihvffets
llvqmylpei lfivsllidv gprelrsslh qllmnvchsl
ainsalpqdh rnnldeisdi fahqkvkfmf gfsedkgril
qifsassfas kfnildffin nilllmeyss tyeanvwktr
ykkyvlesvf tsnsflsars imivgimgks yiteglckam
lietmkviae pkitdehlfl aishiftysk iveglcpnld
lmkhlfwfst lflesrhpii fegallfvsn cirrlymaqf
enesetslis tllkgrkfah tflskienls givwnednft
hilifiinkg lsnpfiksta fdflkmmfrn syfehqinqk
sdhylcymfl lyfvlncnqf eellgdvdfe gemvnienkn
tipkillewl ssdnenanit lyqgailfkc svtdepsrfr
faliirhllt kkpicalrfy svirneirki safeqnsdcv
plafdilnll vthsesnsle klheesierl tkrglsivts
sgifaknsdm mipldvkped iyerkrimtm ilsrmscsa,
``` or a polypeptide having at least 80%, 82%, 85%, 86%, 88%, 90%, 92%, 94%, 95%, 97%, 98% or 99% amino acid sequence identity thereto.

Exemplary sequences to decrease or disable expression of Isu1 in the host cells of the disclosure include but are not limited to sequences that encode (SEQ ID NO: 3)
Met Leu Pro Val Ile Thr Arg Phe Ala Arg Pro Ala Leu Met Ala Ile Arg Pro Val Asn Ala Met Gly Val Leu Arg Ala Ser Ser Ile Thr Lys Arg Leu Tyr His Pro Lys Val Ile Glu His Tyr Thr His Pro Arg Asn Val Gly Ser Leu Asp Lys Lys Leu Pro Asn Val Gly Thr Gly Leu Val Gly Ala Pro Ala Cys Gly Asp Val Met Arg Leu Gln Ile Lys Val Asn Asp Ser Thr Gly Val Ile Glu Asp Val Lys Phe Lys Thr Phe Gly Cys Gly Ser Ala Ile Ala Ser Ser Ser Tyr Met Thr Glu Leu Val Gln Gly Met Thr Leu Asp Asp Ala Ala Lys Ile Lys Asn Thr Glu Ile Ala Lys Glu Leu Ser Leu Pro Pro Val Lys Leu His Cys Ser Met Leu Ala Glu Asp Ala Ile Lys Ala Ala Ile Lys Asp Tyr Lys Ser Lys Arg Asn Thr Pro Thr Met Leu Ser, or a polypeptide having at least 80%, 82%, 85%, 86%, 88%, 90%, 92%, 94%, 95%, 97%, 98% or 99% amino acid sequence identity thereto.

Exemplary sequences to decrease or disable expression of Gre3 in the host cells of the disclosure include but are not limited to sequence that encode (SEQ ID NO: 4)
Met Ser Ser Leu Val Thr Leu Asn Asn Gly Leu Lys Met Pro Leu Val Gly Leu Gly Cys Trp Lys Ile Asp Lys Lys Val Cys Ala Asn Gln Ile Tyr Glu Ala Ile Lys Leu Gly Tyr Arg Leu Phe Asp Gly Ala Cys Asp Tyr Gly Asn Glu Lys Glu Val Gly Glu Gly Ile Arg Lys Ala Ile Ser Glu Gly Leu Val Ser Arg Lys Asp Ile Phe Val Val Ser Lys Leu Trp Asn Asn Phe His His Pro Asp His Val Lys Leu Ala Leu Lys Lys Thr Leu Ser Asp Met Gly Leu Asp Tyr Leu Asp Leu Tyr Tyr Ile His Phe Pro Ile Ala Phe Lys Tyr Val Pro Phe Glu Glu Lys Tyr Pro Pro Gly Phe Tyr Thr Gly Ala Asp Asp Glu Lys Lys Gly His Ile Thr Glu Ala His Val Pro Ile Ile Asp Thr Tyr Arg Ala Leu Glu Glu Cys Val Asp Glu Gly Leu Ile Lys Ser Ile Gly Val Ser Asn Phe Gln Gly Ser Leu Ile Gln Asp Leu Leu Arg Gly Cys Arg Ile Lys Pro Val Ala Leu Gln Ile Glu His His Pro Tyr Leu Thr Gln Glu His Leu Val Glu Phe Cys Lys Leu His Asp Ile Gln Val Val Ala Tyr Ser Ser Phe Gly Pro Gln Ser Phe Ile Glu Met Asp Leu Gln Leu Ala Lys Thr Thr Pro Thr Leu Phe Glu Asn Asp Val Ile Lys Lys Val Ser Gln Asn His Pro Gly Ser Thr Thr Ser Gln Val Leu Leu Arg Trp Ala Thr Gln Arg Gly Ile Ala Val Ile Pro Lys Ser Ser Lys Lys Glu Arg Leu Leu Gly Asn Leu Glu Ile Glu Lys Lys Phe Thr Leu Thr Glu Gln Glu Leu Lys Asp Ile Ser Ala Leu Asn Ala Asn Ile Arg Phe Asn Asp Pro Trp Thr Trp Leu Asp Gly Lys Phe Pro Thr Phe Ala, or a polypeptide having at least 80%, 82%, 85%, 86%, 88%, 90%, 92%, 94%, 95%, 97%, 98% or 99% amino acid sequence identity thereto.

Exemplary sequences to decrease or disable expression of Hog1 in the host cells of the disclosure include but are not limited to sequences that encode (SEQ ID NO: 5)
Met Thr Thr Asn Glu Glu Phe Ile Arg Thr Gln Ile Phe Gly Thr Val Phe Glu Ile Thr Asn Arg Tyr Asn Asp Leu Asn Pro Val Gly Met Gly Ala Phe Gly Leu Val Cys Ser Ala Thr Asp Thr Leu Thr Ser Gln Pro Val Ala Ile Lys Lys Ile Met Lys Pro Phe Ser Thr Ala Val Leu Ala Lys Arg Thr Tyr Arg Glu Leu Lys Leu Leu Lys His Leu Arg His Glu Asn Leu Ile Cys Leu Gln Asp Ile Phe Leu Ser Pro Leu Glu Asp Ile Tyr Phe Val Thr Glu Leu Gln Gly Thr Asp Leu His Arg Leu Leu Gln Thr Arg Pro Leu Glu Lys Gln Phe Val Gln Tyr Phe Leu Tyr Gln Ile Leu Arg Gly Leu Lys Tyr Val His Ser Ala Gly Val Ile His Arg Asp Leu Lys Pro Ser Asn Ile Leu Ile Asn Glu Asn Cys Asp Leu Lys Ile Cys Asp Phe Gly Leu Ala Arg Ile Gln Asp Pro Gln Met Thr Gly Tyr Val Ser Thr Arg Tyr Tyr Arg Ala Pro Glu Ile Met Leu Thr Trp Gln Lys Tyr Asp Val Glu Val Asp Ile Trp Ser Ala Gly Cys Ile Phe Ala Glu Met Ile Glu Gly Lys Pro Leu Phe Pro Gly Lys Asp His Val His Gln Phe Ser Ile Ile Thr Asp Leu Leu Gly Ser Pro Pro Lys Asp Val Ile Asn Thr Ile Cys Ser Glu Asn Thr Leu Lys Phe Val Thr Ser Leu Pro His Arg Asp Pro Ile Pro Phe Ser Glu Arg Phe Lys Thr Val Glu Pro Asp Ala Val Asp Leu Leu Glu Lys Met Leu Val Phe Asp Pro Lys Lys Arg Ile Thr Ala Ala Asp Ala Leu Ala His Pro Tyr Ser Ala Pro Tyr His Asp Pro Thr Asp Glu Pro Val Ala Asp Ala Lys Phe Asp Trp His Phe Asn Asp Ala Asp Leu Pro Val Asp Thr Trp Arg Val Met Met

```
Tyr Ser Glu Ile Leu Asp Phe His Lys Ile Gly Gly

Ser Asp Gly Gln Ile Asp Ile Ser Ala Thr Phe Asp

Asp Gln Val Ala Ala Ala Thr Ala Ala Ala Ala Gln

Ala Gln Ala Gln Ala Gln Ala Gln Val Gln Leu Asn

Met Ala Ala His Ser His Asn Gly Ala Gly Thr Thr

Gly Asn Asp His Ser Asp Ile Ala Gly Gly Asn Lys

Val Ser Asp His Val Ala Ala Asn Asp Thr Ile Thr

Asp Tyr Gly Asn Gln Ala Ile Gln Tyr Ala Asn Glu

Phe Gln Gln,
``` or a polypeptide having at least 80%, 82%, 85%, 86%, 88%, 90%, 92%, 94%, 95%, 97%, 98% or 99% amino acid sequence identity thereto. An exemplary nucleotide sequence encoding HOG1 is

```
                                    (SEQ ID NO: 7)
atgaccacta acgaggaatt cattaggaca cagatattcg gtacagtttt cgagatcaca aatagataca atgatttaaa ccccgttggg atgggggcat tggggttggt ttgctcagcc acggacactt tgacatctca gccagttgcc attaagaaaa tcatgaaacc tttttccact gcagtgctgg ccaaaaggac atatcgtgaa ctaaaactac taaaacatct aagacacgag aacttgattt gccttcagga catatttctt tctccattgg aagatatata ttttgtcacg gaattacaag gaacagattt acatagactc ttgcaaacaa gacccttgga aaagcaattt gttcagtatt tcctatacca aattctaagg ggtttaaaat acgttcactc cgcgggcgtc attcatagag atttgaaacc gagcaacatt ctgattaatg aaaactgtga tttgaagatt tgcgatttcg gtctagcaag aattcaagac cctcaaatga caggctatgt ttccactaga tactacaggg cacctgaaat catgctaacg tggcaaaaat atgacgtcga ggtcgacatt tggtccgctg gttgtatttt tgccgaaatg attgaaggta agcctttgtt ccctgggaaa gatcatgttc accaattttc gatcatcact gacttgttgg gatctccgcc aaaggatgtg ataaatacta tttgttccga aaatactcta aaatttgtta cttcgttacc acacagagat ccaattccat tttctgaaag atttaaaaca gtcgaacctg atgccgtaga cctttttggaa
```

```
aaaatgctgg ttttttgatcc taagaagaga atcactgcgg cggatgcctt ggctcatcct tattcggctc cttaccacga tccaacggat gaaccagtag ccgatgccaa gttcgattgg cactttaatg acgctgatct gcctgtcgat acctggcgtg ttatgatgta ctcagaaatc ctagacttcc ataagattgg tggcagtgat ggacagattg atatatctgc cacgtttgat gaccaagttg ctgcagccac cgctgccgcg gcgcaggcac aggctcaggc tcaggctcaa gttcagttaa acatggctgc gcattcgcat aatggcgctg gcactactgg aaatgatcac tcagatatag ctggtggaaa caaagtcagc gatcatgtag ctgcaaatga caccattacg gactacggta accaggccat acagtacgct aatgagttcc aacagtaa,
``` or a nucleotide sequence having at least 80%, 82%, 85%, 86%, 88%, 90%, 92%, 94%, 95%, 97%, 98% or 99% nucleic acid sequence identity thereto.

Exemplary sequences to decrease or disable expression of Cox15 in the host cells of the disclosure include but are not limited to sequences that encode

```
                                    (SEQ ID NO: 6)
mlfrnievgr qaaklltrts srlawqsiga srnistirqq irktqlynfk ktvsirpfsl sspvfkphva sesnpiesrl ktsknvaywl igtsglvfgi vvlggltrlt esglsitewk pvtgtlppmn qkeweeefik ykespefkll nshidldefk fiffmewihr lwgraigavf ilpavyfavs kktsghvnkr lfglagllgl qgfvgwwmvk sgldqeqlda rkskptvsqy rltthlgtaf flymgmlwtg leilreckwi knpvqaislf kkldnpaigp mrkislalla vsfltamsgg mvagldagwv yntwpkmger wfpssrelmd enfcrredkk dlwwrnllen pvtvqlvhrt cayvaftsvl aahmyaikkk aviprnamts lhvmmgvvtl qatlgiltil ylvpislasi hqagalallt sslvfasqlr kprapmrnvi itlphsskvt sgkilseask laskpl,
``` or a polypeptide having at least 80%, 82%, 85%, 86%, 88%, 90%, 92%, 94%, 95%, 97%, 98% or 99% amino acid sequence identity thereto.

Exemplary sequences to decrease or disable expression of IRA1 in the host cells of the disclosure include but are not limited to sequences such as

```
                                    (SEQ ID NO: 8)
cacccgtcct gtggatcatc ttttgccctg caaatagagc ttcaaactta acattcttct tcagcatata acatacaaca agattaaggc tctttctaaa atgaatcaaa gcgatccgca agacaaaaaa aatttcccaa tggaatactc tttgaccaag catctttttt tttgataggc ttctacttgt tcttcccata gaatctaatt tgaaaacata tgctgatgtg gaggcagatt
```

-continued

```
cagttttcaa ttcgtgtcgg tccatcattt tgaatatagc catcactaag gacttgaacc cgattatcga aaacacatta ggtttaattg acttgattgt gcaagatgaa gaaattacgt ctgacaatat tacagatgat attgcccatt ctatattggt tcttttgaga ttactgagtg atgtttttga gtattactgg gatcaaaaca atgacttcaa gaaaattaga acgataatt acaaaccggg attttcaagt cacaggccaa acttccatac atctaggcca aagcacacga gaatcaatcc agctttggcg acgatgttac tatgtaaaat ttctaagctg aagttcaata caagaacttt aaaggtttta cagaacatgt ctcaccatct ttctggcagc gctactatct caaaatcgag tattttaccc gattcacagg aattttttaca aaagagaaac tatccagcat ataccgagaa aatagattta acaatagatt atatccagag attcatatct gcttccaatc atgttgaatt cacaaagtgt gtcaaaacaa aagttgttgc acctttattg atatcacaca cctcaaccga attgggcgta gtaaaccact tggatttatt tggttgtgag tatttgactg ataagaatct gctagcatat ctggacatac tacaacacct gtcaagttac atgaagagga ccattttttca ttcgcttttg ttatattatg cttccaaagc ttttttattt tggataatgg caaggccaaa agaatacgtc aaaatttata acaatctaat atcatcagat tataatagtc cgtcttcttc atctgataat ggtggttcga ataattctga taaaacgtct atatcccaac tagtctcact gttattcgat gacgtttatt ccacttttag tggatcatca ttattaacaa atgtcaataa tgaccaccac taccatcttc atcattcatc ttcttcatca aagacgacca acactaatag tccaaactct atatcaaaaa cgtcgataaa gcagtcgagt gtgaatgctt ctggcaatgt ttctccgtct cagttttcta ctgggaatga tgcatcgcct acttccccta tggcatcatt gagttcaccc ttaaacacga acatcctagg gtatccgtta tctccaatca cttcaacact aggacaggcg aatacttcca catcgactac ggctgcaact accaaaacag atgcagatac gccctctact atgaatacta acaacaataa taacaataac aacagcgcta atcttaataa tattccacaa cgcatatttt ccttagatga catttcatcc tttaactcga gtagaaaatc actcaatcta gatgatagta actccttgtt tctttgggat acttctcagc attctaatgc atcgatgaca aatacaaata tgcatgcagg agttaataat tctcagtctc agaacgatca gtcttctttta aactatatgg aaaatattat ggagctgtat tccaactata ccggatcaga actatcctcc catactgcca tattaaggtt tttggtggtt ctgaccttat tagacagtga agtatatgat gagatgaact caaattcgta tagaaaaatt tcggaaccga taatgaatat taatccgaag gactctaata cttcaagttg gggctcagca tccaaaaacc caagtatcag gcacctcacc catggcttaa aaaaacttac tttacagcaa ggcaggaaac gtaacgttaa atttttgaca tatttgatta gaaatttgaa tgggggacag ttcgtttcag atgtttcctt gattgactct atcaggtcca ttctattctt aatgacaatg acgtcttcta tatcccaaat cgattcaaat attgcttctg ttatttttttc gaagagattc tacaacttgt tgggtcaaaa tttagaggtc ggcaccaatt ggaattctgc cactgcaaat acttttattt ctcattgtgt tgaaaggaat ccccttacac ataggcgttt acaattagag ttttttgcaa gcggtttaca gctggattct gatttatttt taagacattt acaactggaa aaagaactca atcacataga ccttcccaaa atatcgttat acactgaagg attagggta ttttttcacc tagtaagcac caaaaaactt catgaggata ttgcagaaaa aacctcctct gtgttaaaga gacttttctg cataattgct gatattttgt tgaaagcaac gccttatttt gacgataatg taaccaagat tattgcttct atattggatg ggcatatttt agatcaattt gacgctgcgc gaacactttc taatgatgat catgtcagtt ttgatgctgc cacaagcgtt tacactgagc
```

```
caaccgaaat tattcataac tcatcggatg cctcgttagt ctcttcactt tcccaatcac ccttatcaat taactcagga agcaatatca ccaatacgcg cacctgggat attcaatcaa tcttaccaac cttatcgaac agatcaagtg cttctgattt gagcttgtct aacattttga ctaatccgtt ggaggcacaa caaaataata atgcaaactt gttagcccat agattatctg gggttcctac tactaagaga tacgcttcac cgaacgactc tgaaagatca cgacaaagtc catattcttc tccgccgcaa ttgcaacaaa gtgacttgcc ttctccgctc tcagtcctct cgtcaagtgc aggattttct tctaatcatt cgattacggc aaccccaact attttgaaaa acatcaaatc tccaaaacca aacaaaacaa aaaaaattgc tgatgataaa caattgaaac agccttctta ttcaagagta atactgagtg acaatgatga agcaagaaag attatgatga acattttcag cattttcaaa agaatgacca actggtttat acgcccagat gctaatacag aattcccgaa gacttttacg gatattataa aaccacttttt gtctctata ttggattcta atcaaagact acaagttaca gcgcgggctt ttattgaaat cccattaagt tatatagcta cttttgaaga cattgataat gatcttgacc caagagtact gaatgaccat tatttgttat gtacatatgc cgttactttg tttgcttcat cattgtttga tttgaagtta gaaaatgcga agagagagat gctactagac attattgtta aatttcaacg agtccgttct tatttatcaa atttagcaga aaaacacaac ctagtccagg caataattac gacggagagg ttgacgctgc cattattagt tggtgctgta ggaagtggaa ttttcatttc attatactgc agtcgtggaa atacgccacg cttaataaaa atttcatgtt gtgaatttct acgatccttg agattttatc aaaaatacgt aggcgctttg gatcaatatt ccatttacaa tattgatttc atagatgcta tggcccagga caatttcact gcctcaggat cagtggcttt gcaacggcgt ctaagaaata atatttttaac ttatatcaaa ggatccgact caatccttttt ggattcaatg gacgtgatttt acaagaagtg gttttacttc agctgttcga aatcagttac gcaagaggaa ctagtagatt ttagaagctt ggcaggcatt ctagcttcta tgtcaggtat tctgtctgat atgcaagagt tggaaaaaag caagagcgct ccagataatg aaggagacag cttatcattt gagtcacgaa atcccgctta tgaggtgcac aaaagtctta aactcgagtt aacgaaaaaa atgaatttct ttatttcaaa acaatgtcaa tggttgaata atccaaatct attaacaaga gaaaattcga gagatatatt aagtattgag ttgcatcctc tatcttttaa cttattgttt aacaacctag gactgaaaat agatgaactg atgtcaattg atctttcaaa gtcacatgag gattcatcgt ttgttttact agagcagata ataattataa taagaactat actaaagagg gatgatgatg aaaagataat gctactcttt tcgacggact tgcttgatgc ggtcgataag ttgatcgaaa tagtggagaa aatttccatc aagtcctcca aatattataa gggaattatc caaatgtcga aaatgtttag agcatttgag cactctgaaa agaacctggg catttcaaat catttccatt taaagaataa atggttgaag ttagttattg gttggttcaa actatctatt aataaggatt atgattttga aaacctgtca agaccattaa gggaaatgga tttgcagaaa agggacgaag attttttgta tatcgacact tctattgaat ctgcaaaagc attggcttac ctaacacata atgttccttt agaaataccg ccttcaagct caaaagaaga ttggaacaga tcttctacag tatcatttgg caatcacttt actattttgt taaaaggtct ggagaaaagc gcggacctga atcagtttcc agtttcatta aggcataaga tcagtatact taatgaaaat gtaataatag cgctaacgaa cttatctaat gccaatgtca acgtttcttt aaaattcact ttaccaatgg gttattctcc aaataaagat atcagaatcg cctttttaag agttttcatc gacatagtaa
```

-continued

```
ccaactatcc agttaacccT gagaaacatg aaatggataa aatgctagct atagacgact tcctgaaata tataatcaag aacccaatat tagcattttt cggaagttta gcgtgttctc ctgctgatgt tgatttatat gctggtggat tcttaaacgc ctttgacact agaaatgcgt ctcatatcct tgttactgag ctccttaaac aagaaatcaa acgggccgca agatcagacg atattctcag aagaaatagt tgtgcaacaa gggctttgtc actttacact agatctagag gtaacaaata tttgataaaa actttgagac ccgttttgca agggatagtg ataacaagg agtcttttga aattgataag atgaaaccag gatccgaaaa ctccgaaaag atgttagact tatttgagaa gtacatgaca agattaattg acgcaattac aagttctatt gatgatttcc caatagaatt agttgatatc tgtaaaacaa tttacaatgc tgctagtgta aattttccag aatacgcata tattgccgtt gggtcattcg ttttcttgag gtttatcggg cctgctttag ttagtcctga ttcggaaaat atcattattg ttacgcacgc ccatgacaga aagccctta ttacactagc taaagttatt caaagtttag ctaatggcag ggaaaatata ttcaagaaag atatcttagt ttcaaaagaa gagttttga aacctgtag tgataaaata ttcaattttt tgtctgaatt gtgcaagata ccgactaaca atttcaccgt caatgtaaga gaagatccga caccaataag ctttgactac tcattttgc ataaattctt ttacctcaat gagtttacca taagaaaaga aattattaat gaatccaaat taccagggga gttcagcttt ttgaaaaata ctgttatgct caacgacaaa attcttggtg tattgggaca acctagcatg gaaataaaaa atgaaattcc tccttttgta gtcgagaatc gggaaaaata tccttcattg tatgaattca tgagtcgcta tgccttcaaa aaagtggaca tgaaagaaga agaagaggat aatgcgccat ttgtacatga agcaatgaca ttggatggca tacaaatcat tgtcgtaact tttaccaatt gcgagtacaa taattttgta atggactcac tggtctataa agttctgcag atatatgcaa gaatgtggtg ctctaaacat tatgtagtta tcgattgtac caccttttat gggggtaagg ctaatttcca aaaattgact actctatttt tcagtttgat accagagcaa gcatcaagta attgtatggg atgttattac ttcaacgtca acaaatcatt tatggaccaa tgggcctcat catatactgt agaaaatccg tacttggtca ctacaattcc ccgttgtttc atcaacagca atactgacca agtttgata aagtccttag gattgagtgg taggagtttg gaagttttga aagatgtaag agttactttg catgatatta ccctttatga caaggaaaaa agaagtttt gtcccgtgtc cttgaagata ggaaacaaat acttccaagt tttacatgag attccgcagt tgtacaaggt taccgtatca aacaggacat tcagcatcaa attcaacaat gtttacaaga tatcaaattt aatttcagtc gatgtctcta acaccacagg cgtttcctcg gaatttacgt taagtcttga taatgaagaa aagttggtat tttgcagtcc gaagtaccta gaaattgtga aaatgtttta ttatgcccag ttaaagatgg aagaagactt tggtacggat ttttcgaacg atatttcatt ttcaacatcc tcttcagcag ttaatgcttc ttactgcaat gttaaagaag ttggtgaaat tatatcacat ttgtcattgg tgatccttgt aggtttattc aatgaggatg atctcgtcaa aaacatatca tacaaccttc tcgtggcaac gcaagaagca tttaatttag attttgggac aaggcttcac aaatcccag agacatatgt acccgatgat accaccacgt tcttggccct aattttcaag gcttttttcag aatcttcaac ggaactaact ccatatatat
```

-continued

```
ggaaatatat gctggatggc cttgaaaacg acgtgattcc tcaagaacat attcctacgg
ttgtctgttc attgtcatac tgggtaccaa acttatatga acatgtatat ttggcaaatg
acgaagaggg accagaggcg atttcacgta taatctatag cttaatcagg ttgacggtca
aagagccaaa tttcacgaca gcttaccttc aacagatttg gtttttactg gcattggatg
gtcgtctcac gaacgtgata gttgaagaaa tagtaagtca tgcgctggat agagattcag
aaaacagaga ctggatgaaa gctgtgtcaa tactaaccag ttttccaacg acagagattg
cttgtcaggt aatagagaag ctaataaata tgatcaaatc ttttctacct tctctagcag
ttgaggcttc cgcacacagt tggtctgagc ttactatttt atcaaaaatt agtgtgtcaa
ttttctttga atcacccta ctttcccaga tgtatttacc ggagattctt ttcgctgtgt
ctctgttaat tgatgtcggt ccttcggaaa taagagtctc attgtacgag ttgttgatga
atgtttgtca ttctttaacc aacaatgagt ccttacctga aaggaatagg aaaaatttgg
atatcgtctg tgcaacattc gcacgtcaaa agttgaactt tatctccggt tttagccaag
aaaaaggtag agttttacca aattttgccg cttcctcctt ctccagtaaa ttcggaacat
tagatctctt cactaaaaac attatgctat tgatggaata tggttctatt tcagagggtg
cacaatggga ggcaaaatat aagaaatatt tgatggatgc gattttggc catcggtcgt
tcttctctgc gagagctatg atgattctag gtataatgag taagtcgcac acgtcccttt
tcctttgtaa agaactttta gttgaaacca tgaaggtctt cgcagagcca gttgtggatg
atgaacaaat gttcatcatt atagctcatg tctttactta cagcaaaatt gtcgaagggt
tagatccttc ttcagaatta atgaaagagc tattttggct tgctacaata tgtgttgaat
cccctcatcc tttactcttt gaaggtggtc tcctgttcat ggtaaattgt ttgaagcgac
tgtacacggt ccatcttcaa cttggattcg atggcaaatc gctagccaaa aaattaatgg
aatctagaaa ttttgctgct acgcttttgg ctaagttaga gtcatacaat ggatgcatat
ggaacgaaga taattttcct catattattt taggtttcat tgcaaacggt ttatccattc
ctgtcgtaaa aggagccgca ttagattgtc tacaggccct tttcaagaat acatattacg
aaagaaagtc caacccaaaa tcctccgatt atctttgtta cctttttctta ctccatttgg
tcttaagtcc tgaacaactt tctaccttgt tacttgaagt cggcttcgaa gatgaactgg
tacctttaaa taatacacta aaagtgccac ttactttgat caactggcta agttcagact
cagataaatc taatatagtc ttataccaag gagcactttt gtttagctgt gttatgtcag
acgaaccatg taaattccgt tttgctctat tgatgaggta tttgctcaaa gtcaaccta
tttgtgtatt caggttctat acgctgacta gaaaggaatt caggaggtta tcaaccctag
aacaatcatc tgaagcggtt gctgtctctt ttgaattgat tgggatgctt gttacacaca
gtgagtttaa ttacctagag gaatttaatg atgaaatggt cgaacttta aaaaagagag
gcttgtcagt tgtgaagcct ctggatattt ttgatcagga acatatagaa aagttaaaag
gagagggtga acatcaagtg gcaatttatg agagaaaaag attagcaaca atgatactgg
caagaatgtc gtgctcctaa ttttaaatta gagtattgca gtgattatat acgttttcc
ttataattat attttgtttt atatttgttg gattgtagat tttaaattaa atgaaacgta
gagatttgtg taaagtataa tgattgcaag gttaagagtg aaacattttt agagcactac
taactagcat tttccaaggt ggaaagatcc gaaaaagcac gattaccgga aatccaactg
ttgaccattt ccaaacttgc ctccggttga tc,
``` or a nucleotide sequence having at least 80%, 82%, 85%, 86%, 88%, 90%, 92%, 94%, 95%, 97%, 98% or 99% nucleic acid sequence identity thereto.

Exemplary disabling mutations include but are not limited to:

| Gene | Functional Gene Annotation | Nucleotide Difference | Amino Acid Difference |
|---|---|---|---|
| ISU1 | Fe—S cluster assembly | C412T | H138Y |
| HOG1 | MAP kinase signaling | A844del | M282frameshift[4] |
| GRE3 | Aldose reductase | G136A[5] | A46T |
| IRA2 | Inhibitor of RAS | G8782T | E2928Stop |

The invention will be described by the following non-limiting examples.

EXAMPLE

Corn stover biomass, the most common source of carbon for production of bioethanol, is about 35% glucose polymer and about 19% xylose polymer. Current methods of bioethanol production can only access the glucose, as fermentation of xylose to ethanol is too slow and inefficient to be economically viable. Opening up xylose as a viable carbon source would increase the total amount of fuel available per unit of feedstock, as well as enabling the usage of feedstocks with a higher ratio of xylose to glucose. It has been a goal of researchers and industry for some time to generate large amounts of bioethanol from non-food feedstocks including switchgrass, but the only way the economics as using switchgrass as an ethanol feedstock work is if xylose as well as glucose can be efficiently fermented.

In this study, genetic changes were identified that enable S. cerevisiae to ferment xylose into ethanol at high flux, such that it can ferment xylose aerobically without the need for respiration, a hallmark of the Crabtree-Warburg Effect for glucose. Respiration was blocked in a xylose-consuming S. cerevisiae strain by deleting COX15, which encodes a mitochondrial inner membrane protein involved in the synthesis of heme A, an essential prosthetic group for cytochrome c (Barros et al., 2001; Glerum et al., 1997). This respiration-deficient mutant strain was then subjected to aerobic ALE with xylose as the primary carbon source. Evolved clones selected for their abilities to ferment xylose into ethanol aerobically without respiration were then genome-sequenced to determine the causative genetic changes. By reengineering two genetic changes found in the evolved strains into the original parent strain, a strain was generated with increased xylose fermentation aerobically in the absence of respiration. Importantly, this reengineered strain fermented xylose into ethanol at faster rates anaerobically in both lab medium and lignocellulosic hydrolysate. Finally, these genetic changes increased xylose conversion in another strain background, suggesting that the combination of genetic modifications could be incorporated into existing industrial S. cerevisiae strains Materials and Methods Media Standard undefined yeast lab media were prepared as previously described (Sherman, 2002). Briefly, media for culturing yeast contained 10 g/L yeast extract, 20 g/L peptone (YP), and various carbon source concentrations (X=20-30 g/L xylose, D=20 g/L dextrose/glucose, Gal=20 g/L galactose, Gly=20 g/L glycerol, EtOH=15 g/L ethanol). Solid media also contained 2.5% agar and 200 µg/mL Geneticin (US Biological, Swampscott, MA), 200 µg/mL Hygromycin B (US Biological, Swampscott, MA), 100 µg/mL Nourseothricin (Jena Bioscience, Jena, Germany), or 200 µg/mL Zeocin (Thermo Fisher Scientific, Waltham, MA) as needed. AFEX-pretreated switchgrass hydrolysate (ASGH) was prepared as described elsewhere (Zhang et al., 2020).

Construction of Engineered S. cerevisiae Strains

Yeast strains used in this study are described in Table 2. Deletions of COX15, TAL1, xylA, XYL3, TKL1, GRE3, IRA2, HOG1, and ISU1 were performed by integration of polymerase chain reaction (PCR) products generated from LoxP-KanMX-LoxP (pUG6) or LoxP-HphMX-LoxP (pUG75) plasmid templates (Guldener et al., 1996) and primers containing 40-60 bp of homology sequences flanking the targeted gene (Parreiras et al., 2014). PCR products were purified and transformed (Gietz and Schiestl, 2007) into the appropriate strains. Cre recombinase-mediated excision of LoxP-flanked antibiotic markers was carried out as published elsewhere (Guldener et al., 1996). Complementation of the cox15Δ mutation was performed with the modified pRS416 plasmid (Christianson et al., 1992) Christianson et al., 1992) with the URA3 auxotrophic marker replaced with the HphMX marker (pRSCENHygMX) and containing the COX15 promoter, open reading frame (ORF), and terminator. Insertion of additional copies of TAL1-xylA-XYL3 expression cassette (XYL cassette) and TKL1 promoter, terminator, and ORF were performed using CRISPR/Cas9-mediated genome editing as previously described (Higgins et al., 2018) with some modifications. First, a KanMX antibiotic marker was used to replace the GRE3 ORF (gre3Δ::LoxP-KanMX) or inserted between nucleotides 199269 and 199270 of ChrI (ChrI$^{199269}$) by homologous recombination in the desired strain. ChrI$^{199269}$ is the site of pseudogene, which has been previously used as a location for transgene insertion (Hittinger and Carroll, 2007). Selected strains were then transformed with the pXIPHOS plasmid (Higgins et al., 2018) to express Cas9 and an sgRNA sequence (ATGAAGGAGAAAACT-CACCG; SEQ ID NO:1), which was designed by CRISpy-pop (Stoneman et al., 2020) to target KanMX. The XYL cassette and TKL1 PCR products containing 50-60 bp of flanking sequences to GRE3 and the ChrI locus, respectively, were co-transformed at 20-fold molar excess as repair templates. Transformed colonies were restreaked onto YPD twice to cure the pXIPHOS plasmid, followed by PCR and Sanger sequencing verification of TAL1-xylA-XYL3 and TKL1 insertions. All strains were confirmed for gene deletion and antibiotic marker excision by PCR with independent outside flanking primers. Sanger sequencing of PCR products and DNA plasmids was performed by University of Wisconsin-Madison Biotechnology Center.

Adaptive Laboratory Evolution (ALE)

ALE for selection of clones that ferment xylose aerobically without respiration was performed using the GLBRCY583 (Y583) strain, which lacks COX15. Three separate flasks containing 30 mL YP medium with 3% xylose and 0.05% glucose were inoculated with Y583 to optical density at 600 nm wavelength ($OD_{600}$) of 0.2 and shaken at 250 rpm and 30° C. When the cell densities of each flask reached $OD_{600}$=2-6, the cultures were subcultured with fresh medium to $OD_{600}$=0.2. Medium for the second passage included 0.1% glucose, whereas all subsequent passages lacked glucose. Between 6-8 passages for each culture were performed until the maximum cell densities were reached within 48 h and all xylose was consumed from the medium as determined by high performance liquid chromatography (HPLC) and refractive index detection (RID) (Schwalbach et al., 2012). Two out of the three ALE cultures that displayed significant growth on xylose-only medium were plated onto YPX+Hygromycin B agar plates. Isolated colonies from the two evolved flasks were tested for growth on xylose aerobically in flask experiments described below. $OD_{600}$ measurements were performed using 1-cm pathlength cuvettes and a Beckman Coulter DU720 spectrophotometer. Single clones (Evo1 and Evo2) from the two independently-evolved flasks with the fastest cell growth and xylose consumption rates were selected for further study.

Genomic DNA Library Preparation and Sequence Analysis

Genomic DNA preparation and Illumina sequencing were performed as described previously (Sato et al., 2016) with some modifications. DNA was submitted to the University of Wisconsin-Madison Biotechnology Center. DNA concentration was verified using the Qubit® dsDNA HS Assay Kit (Life Technologies, Grand Island, NY). Samples were prepared according the TruSeq Nano DNA LT Library Prep Kit (Illumina Inc., San Diego, California, USA) with minor modifications. Samples were sheared using a Covaris M220 Ultrasonicator (Covaris Inc, Woburn, MA, USA), and were size selected for an average insert size of 550 bp using SPRI bead-based size exclusion. Quality and quantity of the finished libraries were assessed using an Agilent DNA1000 chip and Qubit® dsDNA HS Assay Kit, respectively. Libraries were standardized to 2 nM.

Cluster generation was performed using the Illumina PE Cluster Kits v4 and the Illumina cBot. Paired-end, 125 bp sequencing was performed, using v4 SBS chemistry on an Illumina HiSeq2500 sequencer. Images were analyzed using the Illumina Pipeline, version 1.8.2. All DNA sequencing reads have been deposited in the NCBI SRA under BioProject PRJNA279877. Paired-end reads were mapped to GLBRCY22-3 (GCA_001634645.1) (McIlwain et al., 2016) using Bwa-mem 0.7.12-r1039 (Li, 2013). Genomic variants were identified using GATK (v3.4) (McKenna et al., 2010) with duplicate marking and indel realignment. Variants were called using Haplotype Caller without input of known sites/variants. GATK variant filtration was done using the GATK-recommended criteria: QD<2, FS>60, and MQ<40. Coverage analysis was performed by summing unique counts in 500-bp non-overlapping windows using custom Python and R scripts and visualized using the spplDer pipeline (Langdon et al., 2018).

Cell Culturing and Phenotypic Growth Analysis

Aerobic tube and anaerobic flask fermentation assays were performed as previously described (Parreiras et al., 2014) with some modifications. For aerobic and anaerobic growth assays, inoculum cultures were started from single colonies grown in YPD medium overnight and passaged to $OD_{600}=0.3$. Log phase cultures were then diluted to $OD_{600}=0.1$ in the appropriate medium at the start of the assay. Yeast cultures were grown in culture tubes containing 10 mL of medium shaken at 250 rpm at 30° C. or in 30 mL of medium stirred with a magnetic stir bar in flasks placed in an anaerobic chamber (Coy Laboratory Products Inc. Grass Lake, MI), which was maintained with 2-5% $H_2$, 2-5% $CO_2$ and 90-95% $N_2$.

For COX15 complementation experiments, cox15Δ strains transformed with the pRSCENHygMX (Empty vector) or pRSCENHygMX-COX15 plasmid were cultured in medium containing 200 μg/mL Hygromycin B. For cell culture experiments using Antimycin A, yeast cells were grown to log phase in YPD medium aerobically and then shifted into tubes containing 10 mL fresh YPD or YPX medium treated with 10 μL DMSO or 10 μL of 0.5 mg/mL Antimycin A in DMSO (0.5 μg/mL final concentration, A8674, Sigma-Aldrich, St. Louis, MO), and incubated at 30° C. with shaking. For aerobic cell growth assay using glucosamine, yeast cells were grown to log phase in YPD medium aerobically and then shifted into tubes containing 10 mL fresh YPD or YPD medium treated with 250 μL of 200 mg/mL D-(+)-glucosamine hydrochloride (5 mg/mL final concentration, G4875, Sigma-Aldrich), and incubated at 30° C. with shaking.

For anaerobic bioreactor experiments, fermentations were conducted in 0.25 L Minibio bioreactors (Applikon Biotechnology Inc., Foster City, CA) containing 100 mL of 7% glucan-loading ASGH. Prior to fermentation, hydrolysates were adjusted to pH 5.0 and filtered through a 0.2 μm filter to remove precipitates and to ensure sterility. After transfer to the fermentation vessel, hydrolysates were sparged with 100% $N_2$ at the flow rate of ~20 mL/min overnight before the inoculation. S. cerevisiae strains were grown to early stationary phase in YPD aerobically and then diluted $OD_{600}=0.2$ in fresh YPD for ~10 h. Cultures were then centrifuged at 3,000×g for 5 min, the cell pellets were resuspended into ~10 mL of hydrolysate from the pre-sparged vessels and then inoculated back into each bioreactor to a starting $OD_{600}$ of 0.5. Fermentations were conducted at 30° C. with continuous stirring (500 rpm) and sparged at ~20 mL/min with 100% $N_2$. During the fermentation, pH was maintained at 5.0 by automated addition of 5% NaOH. Cell density measurements were blanked with $OD_{600}$ measurements from uninoculated hydrolysate diluted 1:10 or 1:25 with water. Extracellular glucose, xylose, ethanol, glycerol, and galactose concentrations for all experiments were determined by HPLC-RID. Calculations for xylose consumption and ethanol production rates and yields from anaerobic bioreactor fermentations were determined for the time period after all glucose was depleted and as described elsewhere (Sato et al., 2016).

Results

Evolved Yeast Mutants Convert Xylose into Ethanol Aerobically in the Absence of Respiration Previously, a S. cerevisiae strain was engineered to express single copies of xylose isomerase (xylA from Clostridium phytofermentans) and xylulokinase (XYL3 from Scheffersomyces stipitis), as well as an additional copy of the native transaldolase TAL1 by genomic insertion of a DNA cassette (henceforth called the "XYL cassette"). Informed by ALE (Sato et al., 2016), deletion mutations were engineered in HOG1, ISU1, GRE3, and IRA2 to enable rapid conversion of xylose into ethanol anaerobically. Interestingly, this xylose-fermenting strain (hereafter referred to as the "Parent" strain) converted xylose into ethanol in the presence of oxygen, albeit worse than the theoretically expected ethanol yield from xylose. However, this Parent strain could not grow on and fennent xylose aerobically in the presence of Antimycin A (Sato et al., 2016), or with the cox15Δ mutation, which is essential for the function of Electron Transport Chain Complex IV (FIG. 8). Thus, the Parent strain requires respiration to grow on xylose in the presence of oxygen.

Figure 1B:
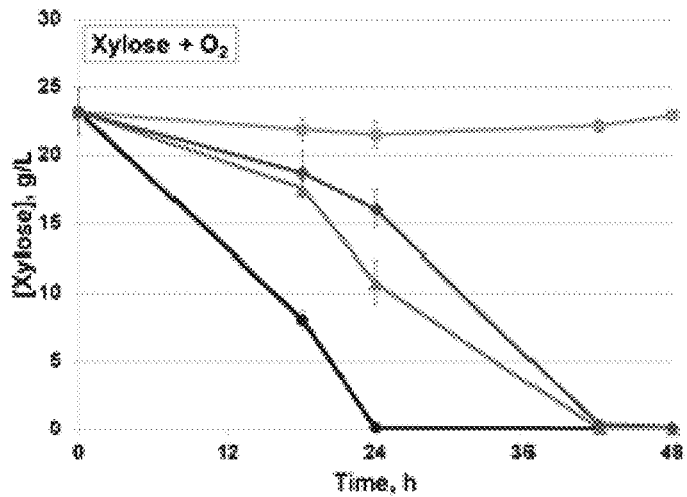
Figure 1C:
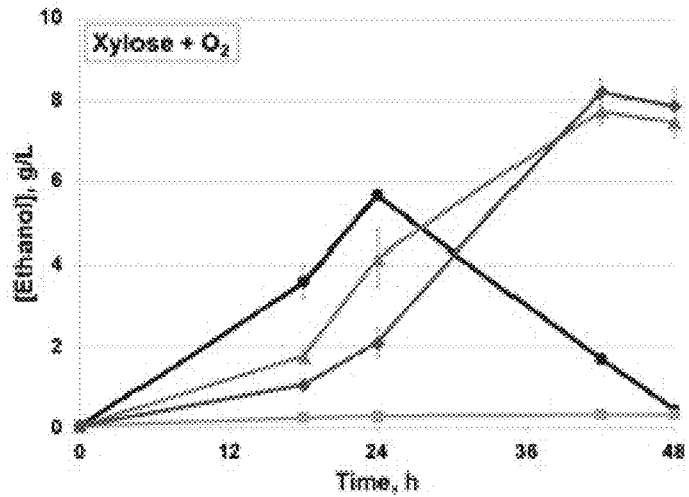
Figure 2A:
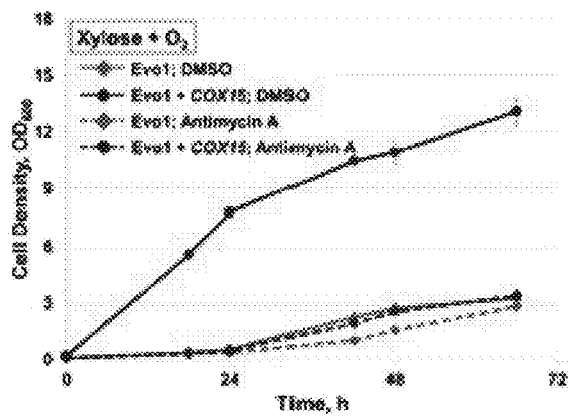
FIGS. 2A-2F. Evolved strains can ferment xylose into ethanol aerobically in the presence of Antimycin A. The evolved strains (Evo1 and Evo2) containing the empty plasmid (Evo1+Empty or Evo2+Empty) or pRSCEN-HygMX-COX15 plasmid (Evo1+COX15 or Evo2+COX15) were cultured aerobically in YPX+Hygromycin B medium containing a DMSO control or were cultured aerobically 0.5 µg/mL Antimycin A, an inhibitor of Complex III. Average cell density (A and D), extracellular xylose (B and E), and ethanol (C and F) concentrations from independent triplicate experiments with SEM are reported. Evo1, Evo2, Evo1+COX15, and Evo2+COX15 indicate strains Y1031+Empty, Y1033+Empty, Y1031+COX15, and Y1033+COX15, respectively.
Figure 2D:
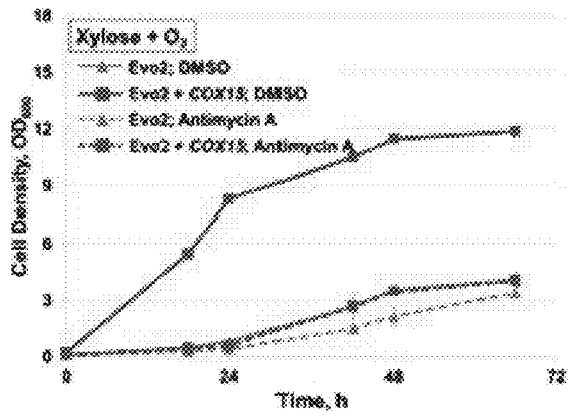
Figure 2B:
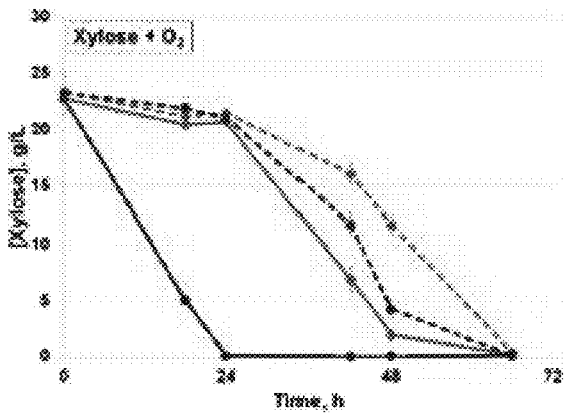
Figure 2E:
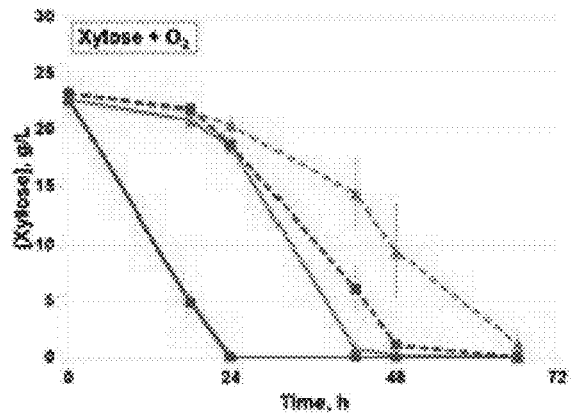
Figure 2C:
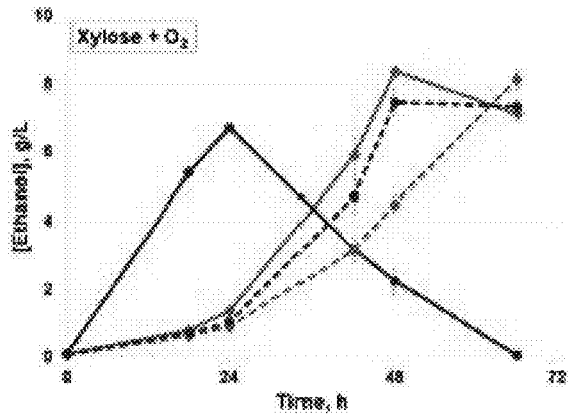
Figure 2F:
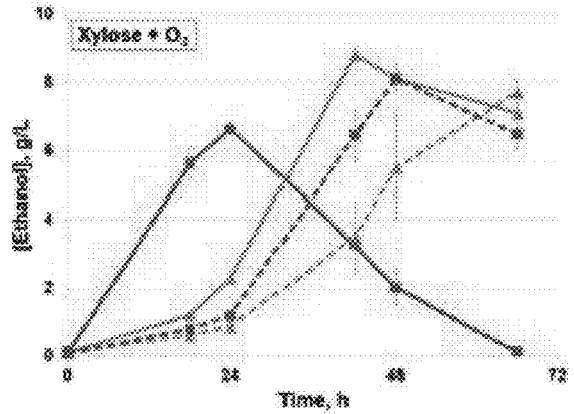
Figure 8A:
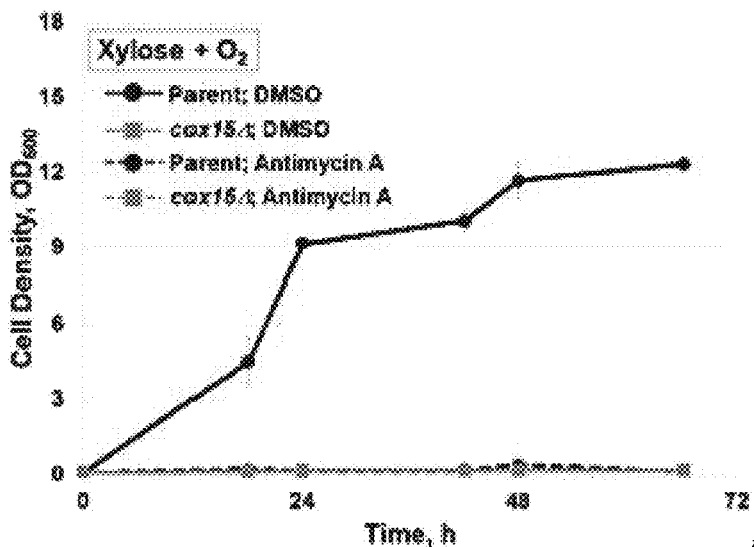
FIGS. 8A-8C. Respiration is required for aerobic conversion of xylose into ethanol by the mutant gre3Δ hog1Δ isu1Δ ira2Δ xylose-fermenting strain. Respiration-deficient (cox15Δ), and parent containing wild-type COX15 (Parent) strains were cultured aerobically in YPX medium containing DMSO control or 0.5 µg/mL Antimycin A. Average cell density (A), extracellular xylose (B), and ethanol (C) concentrations from independent triplicate experiments with SEM are reported. Parent and cox15Δ indicate strains Y560 and Y583, respectively (Table 2).
Figure 8B:
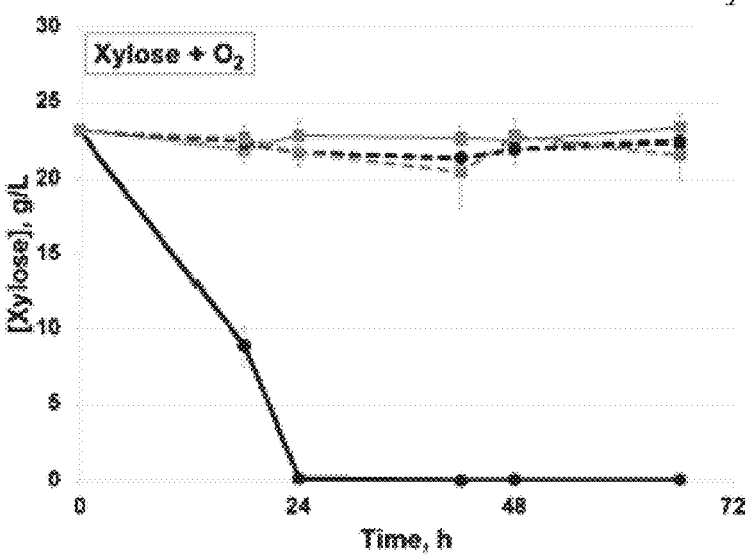
Figure 8C:
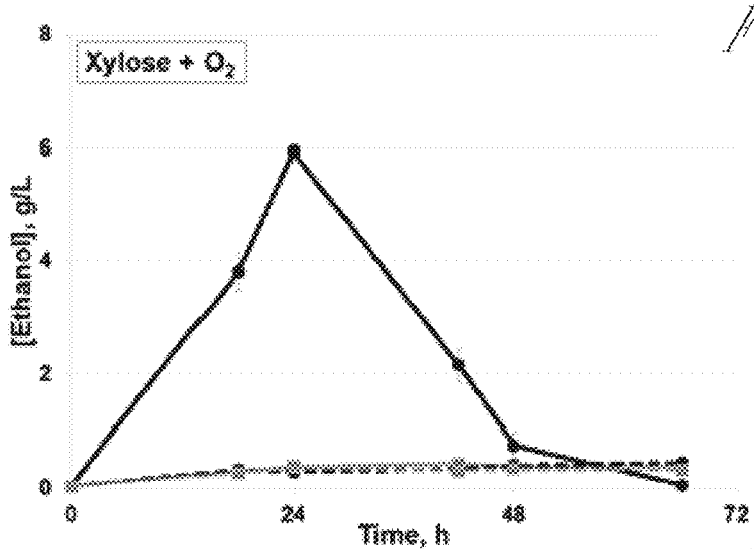
Figure 10A:
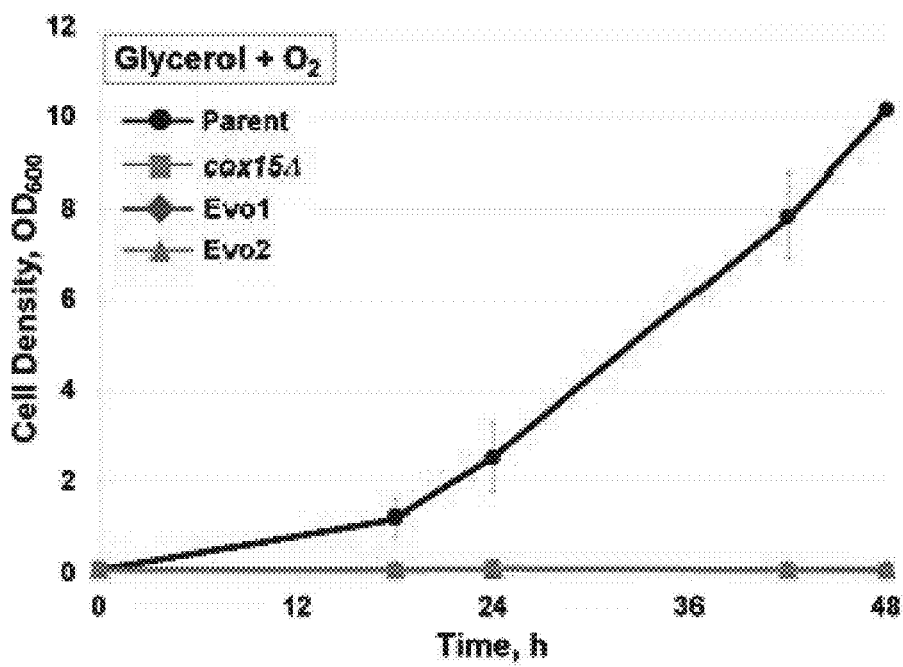
FIGS. 10A-10B. Evolved mutations do not enable growth on respiratory carbon sources aerobically. The evolved (Evo1 and Evo2), respiration-deficient (cox15Δ), and Parent containing wild-type COX15 strains were cultured aerobically in YP medium containing glycerol (A) or galactose (B). The evolved strains were evolved from the respiration-deficient strain. Average cell density from independent triplicate experiments with SEM is reported. Parent, cox15, Evo1, and Evo2 indicate strains Y560, Y583, Y1031, and Y1033, respectively.
Figure 10B:
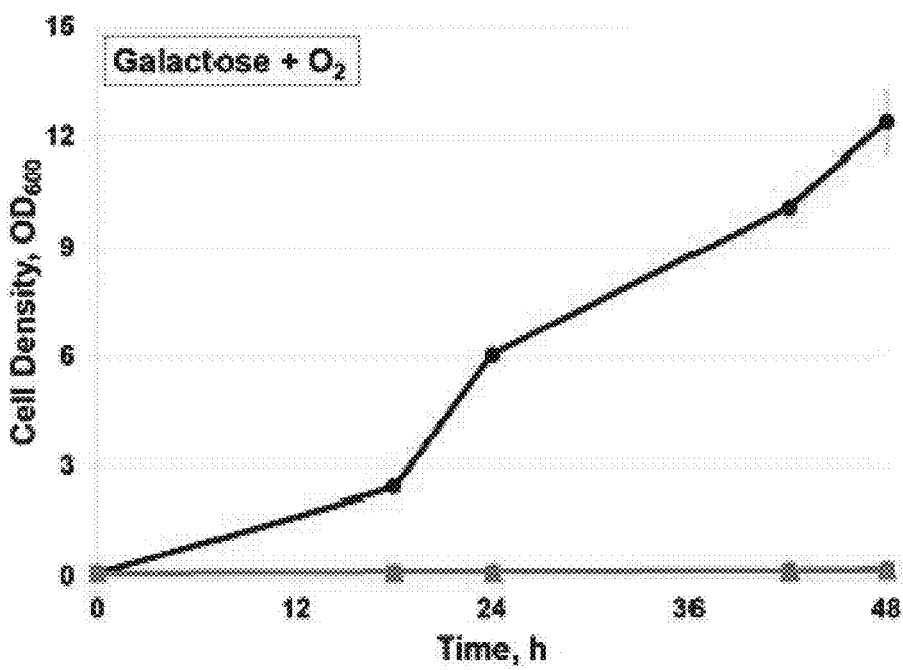

To increase the flux of xylose to ethanol without aerobic respiration, ALE was used to select for respiration-deficient mutants that grow aerobically on xylose. Specifically, the Parent strain with the cox15Δ mutation was evolved aerobically on xylose in three separate flasks (FIG. 8A). Two out of the three flasks displayed significant growth during the third passage (FIG. 8B-C). From each of these two flasks, independent clones (Evo1 and Evo2) were isolated and confirmed to grow on and ferment xylose into ethanol aerobically (FIG. 1). The evolved strains grew on and consumed xylose more slowly than the Parent strain, but they produced higher levels of ethanol, likely due to their inabilities to respire. It was confirmed that the Evo1 and Evo2 strains did not evolve the ability to respire without COX15 since both Evo1 and Evo2 strains did not grow on glycerol or galactose (FIG. 9). These results indicated that the evolved strains ferment xylose into ethanol aerobically without the requirement for respiration. A possible, albeit unlikely, mechanism for aerobic growth on xylose by the evolved strains could be from bypassing the need for Cox15p. To test this, the Evo1 and Evo2 strains were transformed with a low copy plasmid with or without COX15. The evolved strains expressing COX15 restored the ability to respire xylose and ethanol aerobically (FIG. 2). Then these strains were cultured in xylose aerobically with the addition of Antimycin A, which inhibits oxidative phosphorylation by the Electron Transport Chain Complex III. The evolved strains, with or without COX15, could grow on and ferment xylose into ethanol aerobically in the presence of Antimycin A (FIG. 2), which is a phenotype analogous to how Crabtree-Warburg-positive yeasts metabolize glucose. Together, these results suggest that the evolved strains can metabolize xylose into ethanol aerobically without the requirements for Complex III and IV activities.

Evolved Mutations do not Bypass Glucose Repression

Figure 11A:
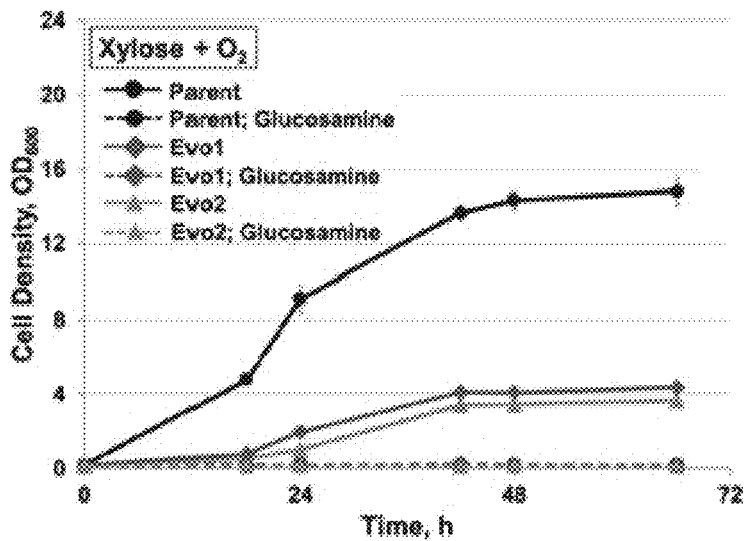
FIGS. 11A-11C. Evolved mutations do not enable growth on xylose when under glucose-repression. The evolved (Evo1 and Evo2) and parent containing wild-type COX15 (Parent) strains were cultured aerobically in YPX medium with or without 0.5 µg/mL glucosamine. Average cell density (A), extracellular xylose (B), and ethanol (C) concentrations from independent triplicate experiments with SEM are reported. Parent, Evo1, and Evo2 indicate strains Y560, Y1031, and Y1033, respectively.
Figure 11B:
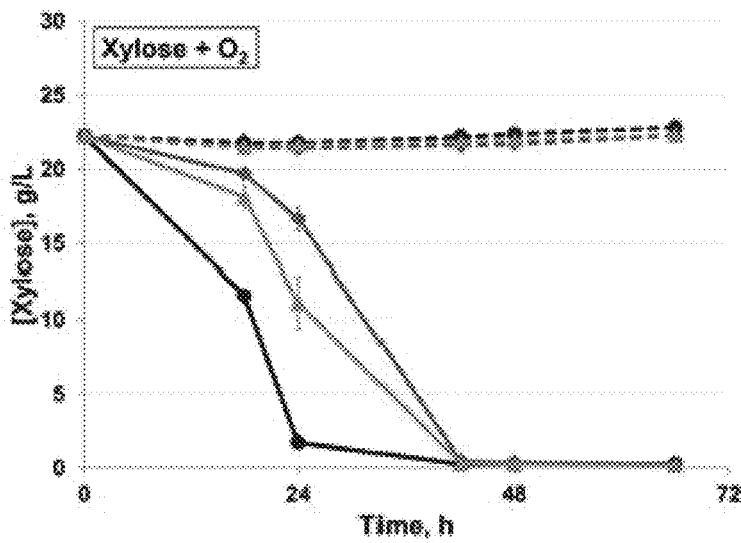
Figure 11C:
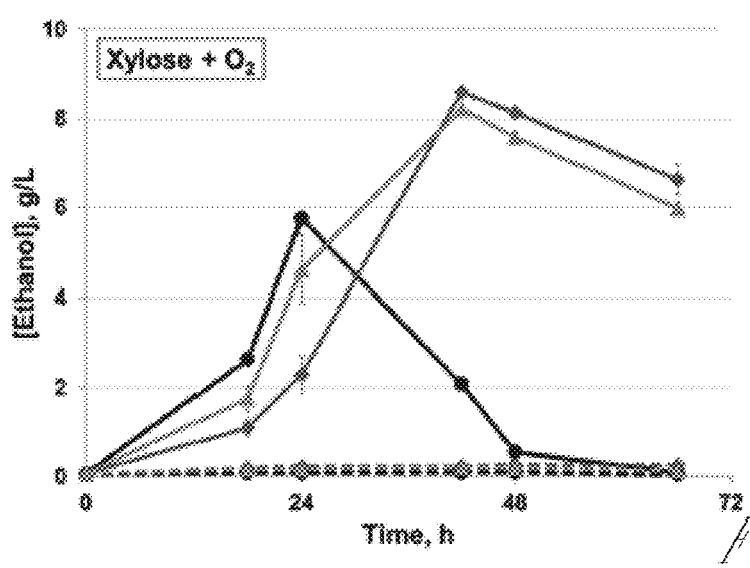

Another hallmark of Crabtree-Warburg-positive yeasts is glucose-mediated repression of metabolic pathways. In the presence of high levels of glucose, the Snf1p pathway is inactivated to repress the expression of genes involved in gluconeogenesis, respiration, and non-fermentable carbon metabolism, leading Crabtree-Warburg-positive yeasts to metabolize glucose first (Kayikci and Nielsen, 2015). Extracellular glucose is also bound by the sensors Rtg2p and Snf3p, leading to a signaling cascade that relieves repression by the transcription factor Rtg1p (Johnston and Kim, 2005). These regulatory pathways likely lead to inefficient fermentation of other sugars, such as xylose, present in lignocellulosic hydrolysates into ethanol; thus, overcoming glucose repression is important for the biofuel industry. It was examined whether aerobic xylose fermentation by the evolved strains could be repressed by the non-metabolizable glucose analog, glucosamine. Aerobic growth and xylose consumption by both the Parent and the evolved strains were blocked in the presence of glucosamine (FIG. 11), which suggests that the fermentation of xylose into ethanol aerobically by the Evo1 and Evo2 strains requires genes and pathways that are repressed by glucose.

Evolved Mutations Enhance the Rate of Anaerobic Xylose Fermentation

Figure 12A:
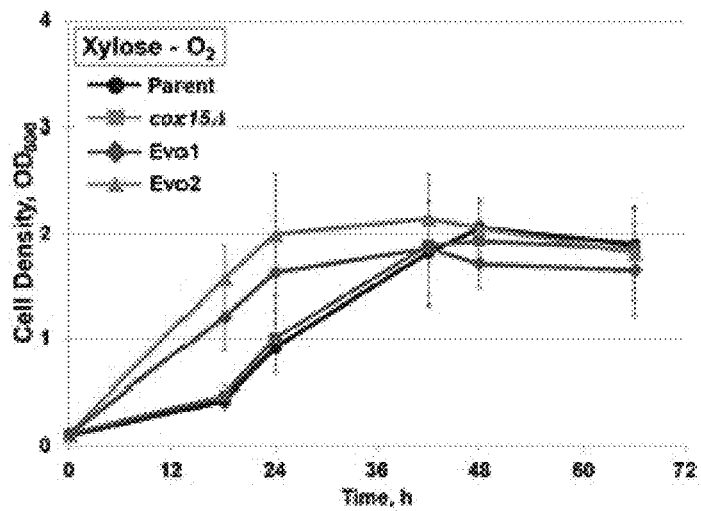
FIGS. 12A-12C. Evolved strains ferment xylose into ethanol anaerobically faster than their parent strain. The evolved (Evo1 and Evo2), respiration-deficient (cox15Δ), and Parent containing wild-type COX15 strains were cultured anaerobically in YPX medium. The evolved strains were evolved from the respiration-deficient strain. Average cell density (A), extracellular xylose (B), and ethanol (C) concentrations from independent triplicate experiments with SEM are reported. Parent, cox15Δ, Evo1, and Evo2 indicate strains Y560, Y583, Y1031, and Y1033, respectively.
Figure 12B:
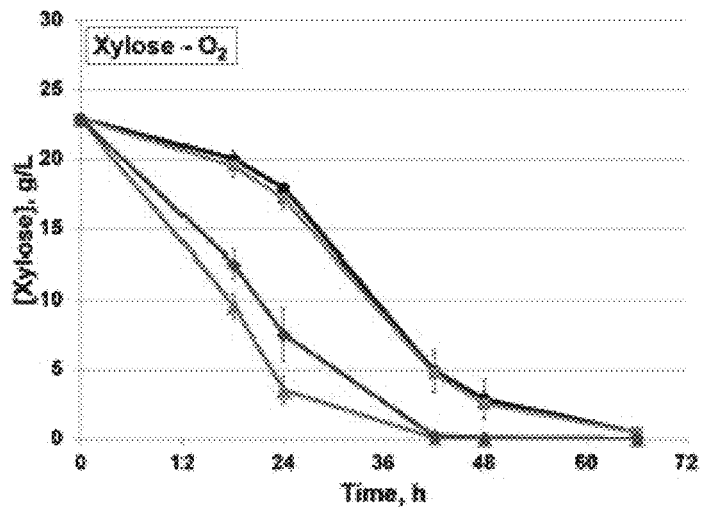
Figure 12C:
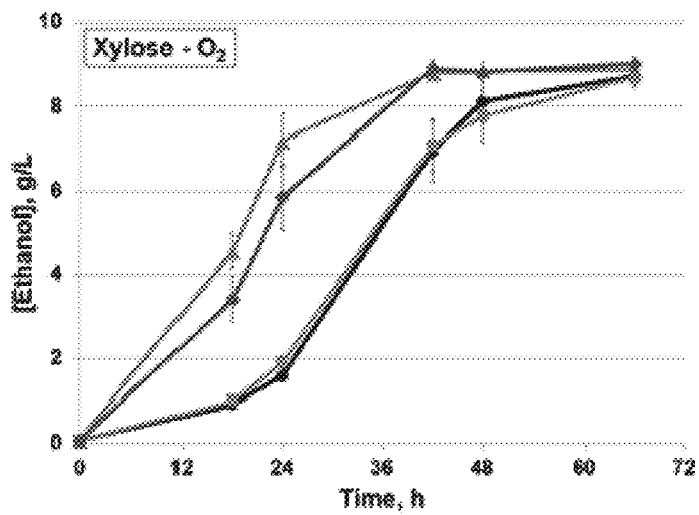

The Crabtree-Warburg Effect in S. cerevisiae is a product of high glucose flux, which consequentially results in rapid glucose consumption aerobically and anaerobically. Thus, S. cerevisiae is used as an industrial workhorse for its ability to rapidly convert glucose into biofuels without the costly need for aeration. It was investigated if the evolved mutations positively impacted the rate of anaerobic xylose fermentation. Under anaerobic conditions, both the evolved strains fermented xylose into ethanol faster than the Parent strain, with or without COX15 (FIG. 12). Unexpectedly, the evolved strains expressing COX15 displayed slightly increased anaerobic xylose fermentation rates but had no differences in final ethanol titer (FIG. 13), suggesting that COX15 may have direct or indirect anaerobic functions in xylose fermentation. Importantly, these studies further indicate that the evolved mutations increase the rate of xylose fermentation under anaerobic conditions.

Evolved Strains Contain Overlapping Duplications in ChrIV and XVI

To identify the evolved genetic changes that caused the Crabtree-Warburg-like phenotype, the Evo1 and Evo2 strains were sequenced using Illumina HiSeq technology and mapped their sequencing reads to the Y22-3 parental genome (McIlwain et al., 2016). Multiple single nucleotide changes in the evolved strains were identified that were not present in the unevolved cox15 strain. However, the mutations in the two independently evolved strains did not overlap in the same genes or in genes within the same pathways or biological functions. Nevertheless, when comparing the read coverages across all chromosomes, it was found that the read coverages across regions of ChrII, IV, and XVI were two-fold higher in the evolved strains than the unevolved cox15Δ strain, indicating that segmental duplications occurred during the directed evolution (FIG. 3A). Despite being evolved independently, both the evolved strains had duplications of nearly identical 92 kb region of ChrIV and in a large, 410 kb overlapping region of ChrXVI, whereas the ChrII duplication was only present in the Evo1 strain. It was found that the duplicated region of ChrIV contained the XYL cassette expressing TAL1, xylA, and XYL3, which had been inserted into the HO locus (Parreiras et al., 2014) (FIG. 3B). The overlapping region in ChrXVI notably included TKL1, which encodes transketolase, a pentose phosphate pathway enzyme involved in xylose catabolism (FIG. 3C).

Figure 4A:
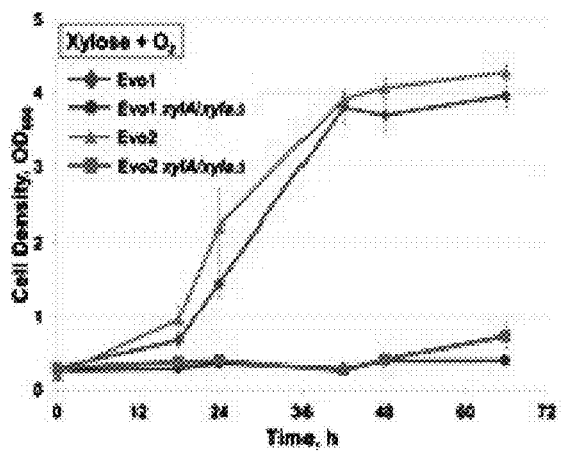
FIGS. 4A-4F. Duplications of xylA (A-C) and TKL1 (D-F) are responsible for aerobic xylose fermentation by the evolved strains. The evolved strains (Evo1 and Evo2) and the evolved strains with deletion of one copy of xylA or TKL1 were cultured aerobically in YPX medium. Average cell density (A and D), extracellular xylose (B and E), and ethanol (C and F) concentrations from independent triplicate experiments with SEM are reported. Evo1, Evo2, Evo1 xylA/xylaΔ, Evo2 xylA/xylaΔ, Evo1 TKL1/tkl1Δ, and Evo2 TKL1/tkl1Δ indicate strains Y1031, Y1033, Y1176, Y1183, Y1185, and Y1189, respectively.
Figure 4D:
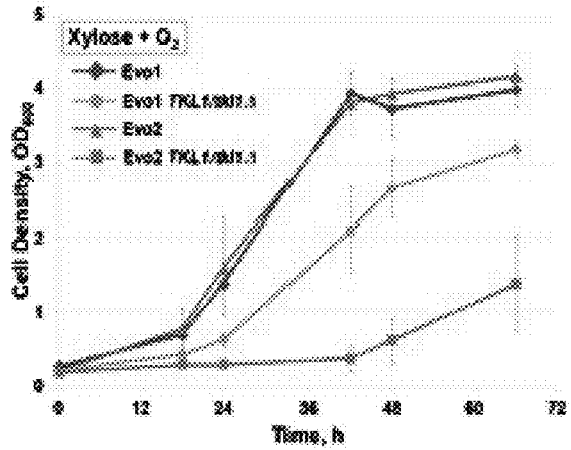
Figure 4B:
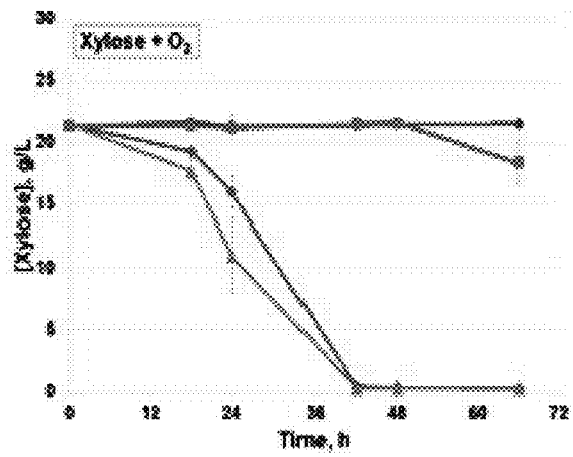
Figure 4E:
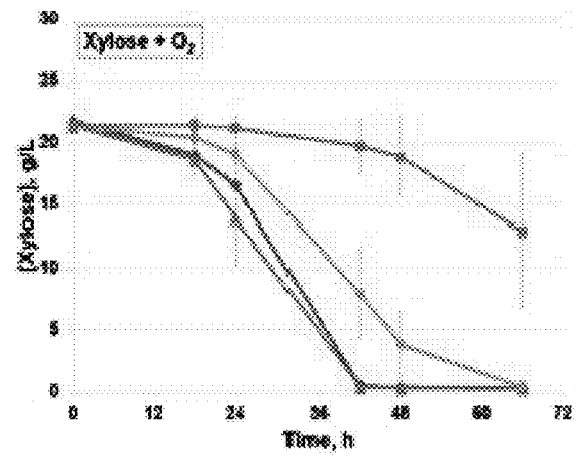
Figure 4C:
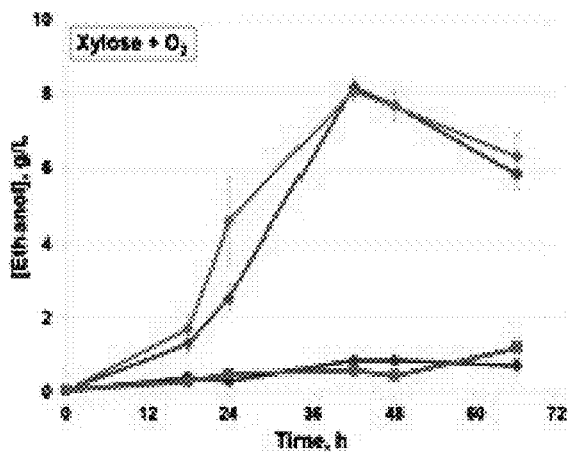
Figure 4F:
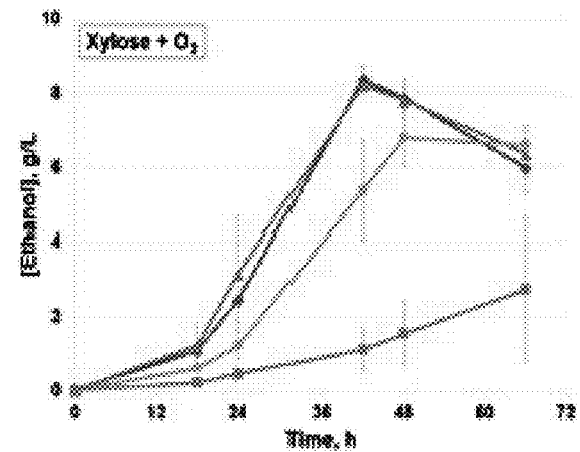

Duplications of Engineered Xylose Metabolism Genes and TKL1 are Required for Robust Aerobic Xylose Fermentation It was sought to confirm whether duplications of the engineered xylose metabolism genes TAL1, xylA, and XYL3 from ChrIV and TKL1 from ChrXVI were important for the ability of the evolved strains to ferment xylose aerobically without respiration. Each of the four genes from the evolved strains were individually deleted and tested for their requirement in aerobic xylose fermentation. Deletion of the second copy of xylA blocked aerobic xylose fermentation by both evolved strains (FIG. 4A-C), whereas deletion of an extra copy of TAL1 had no effect (FIG. 14). In contrast, deletion of an extra copy of XYL3 had a modest effect on the Evo1 strain but little effect on the Evo2 strain, suggesting that the genetic bases for the Evo1 and Evo2 phenotypes are overlapping but not identical (FIG. 14). Consistent with this hypothesis, deletion of an extra copy of TKL1 had a stronger effect on the Evo2 strain, significantly decreasing aerobic xylose fermentation rate, whereas the Evo1 strain with the extra copy of TKL1 deleted displayed modestly decreased xylose fermentation (FIG. 4D-F). Together, these results suggest that duplications of xylA, XYL3, and TKL1 are important for aerobic xylose fermentation without respiration in the evolved strains.

Figure 5A:
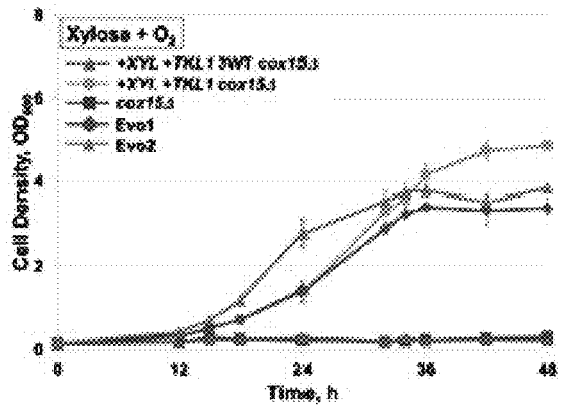
FIGS. 5A-5F. Duplications of the XYL cassette and TKL1 together with deletion mutations in HOG1, ISU1, and IRA2 enhance fermentation of xylose aerobically and anaerobically. The evolved strains (Evo1 and Evo2) and the engineered strains with deletion of COX15 were cultured aerobically in YPX medium (A-C). The engineered strains with wild-type COX15 were cultured anaerobically in YPX medium (D-F). Average cell density (A and D), extracellular xylose (B and E), and ethanol (C and F) concentrations from independent triplicate experiments with SEM are reported. 3WT indicates a genotype of wild-type HOG1, ISU1, and IRA2.
Figure 5D:
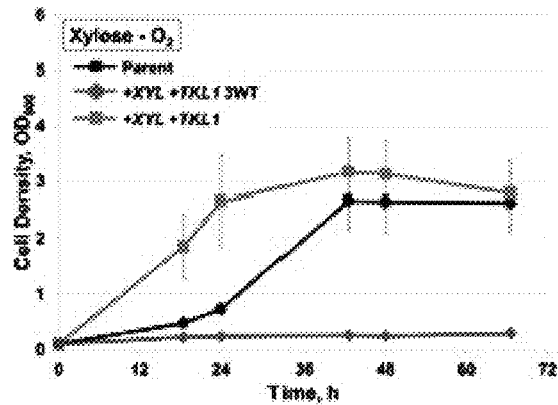
Figure 5B:
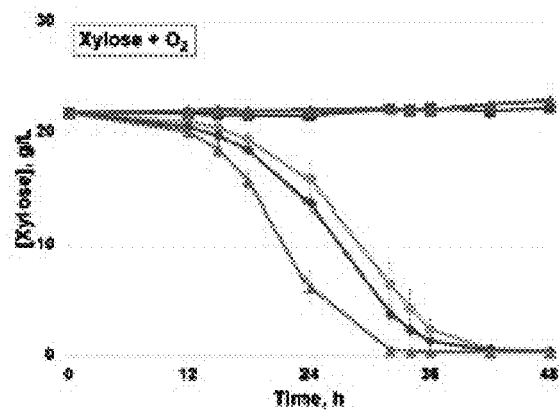
Figure 5E:
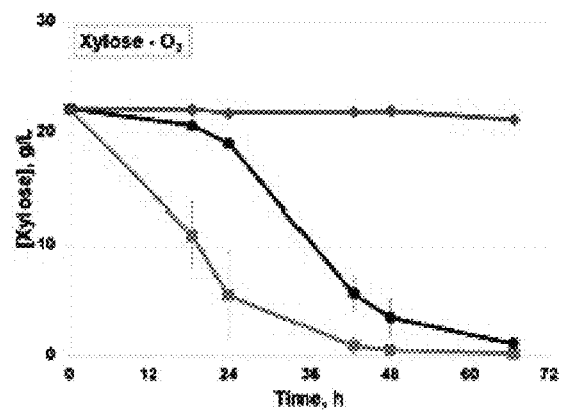
Figure 5C:
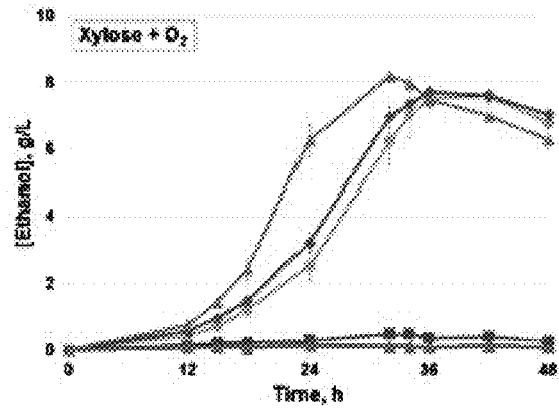
Figure 5F:
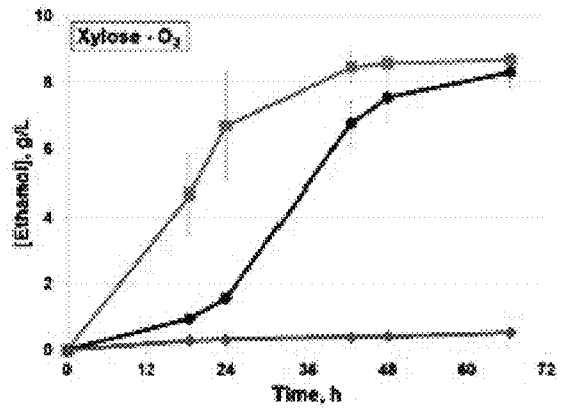
Figure 6A:
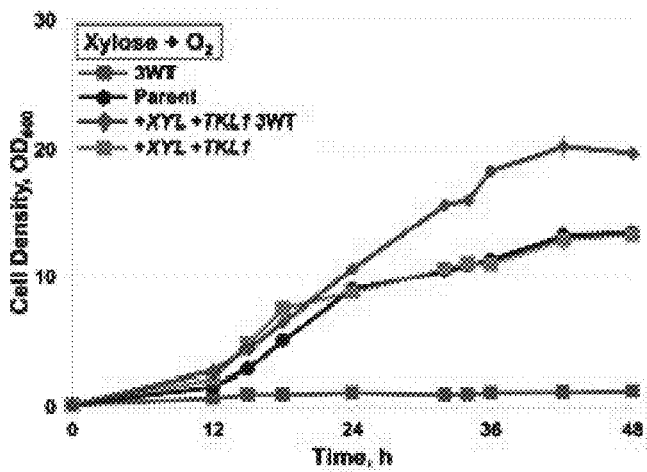
FIGS. 6A-6C. Duplications of the XYL cassette and TKL1 increase the xylose conversion rate, while deletion mutations in HOG1, ISU1, and IRA2 reprogram aerobic xylose metabolism from respiration into fermentation. The engineered strains with wild-type COX15 were cultured aerobically in YPX medium. Average cell density (A), extracellular xylose (B), and ethanol (C) concentrations from independent triplicate experiments with SEM are reported. All the strains contain at least one copy of the XYL cassette and TKL1. 3WT indicates a genotype of wild-type HOG1, ISU1, and IRA2.
Figure 6B:
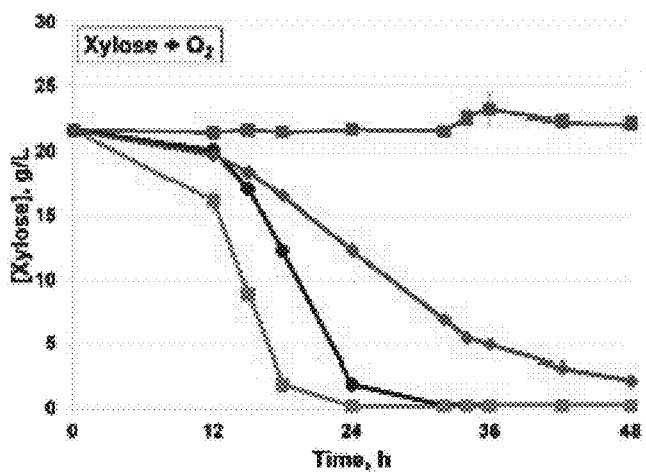
Figure 6C:
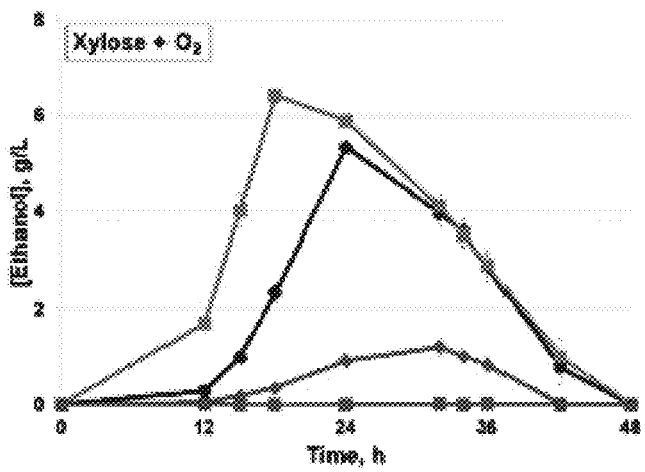
Figure 13A:
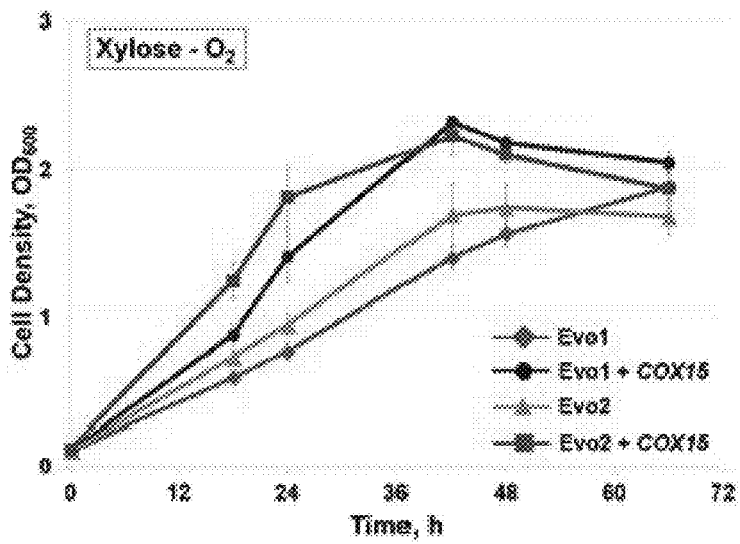
FIGS. 13A-13C. Restoration of COX15 modestly enhances anaerobic xylose fermentation by the evolved strains. The evolved strains (Evo1 and Evo2) transformed with the empty vector control and the evolved strains expressing COX15 (Evo1+COX15 and Evo2+COX15) were cultured anaerobically in YPX medium. Average cell density (A), extracellular xylose (B), and ethanol (C) concentrations from independent triplicate experiments with SEM are reported. Evo1, Evo2, Evo1+COX15, and Evo2+COX15 indicate strains Y1031+Empty, Y1033+Empty, Y1031+COX15, and Y1033+COX15, respectively.
Figure 13B:
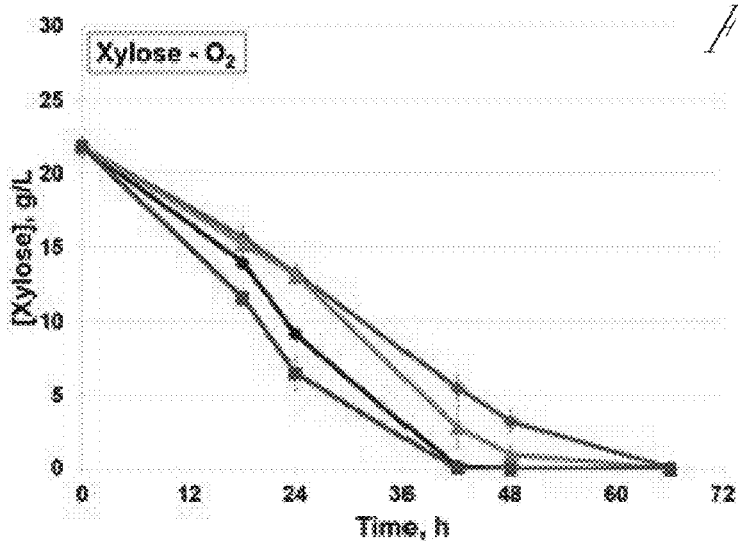
Figure 13C:
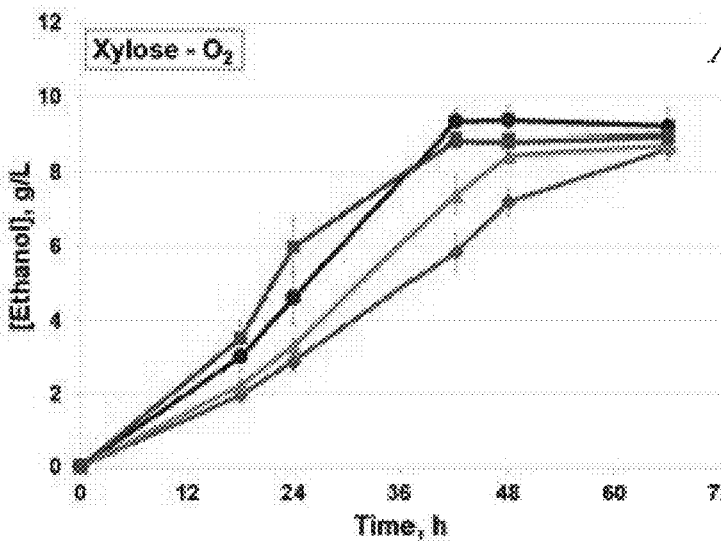
Figure 14A:
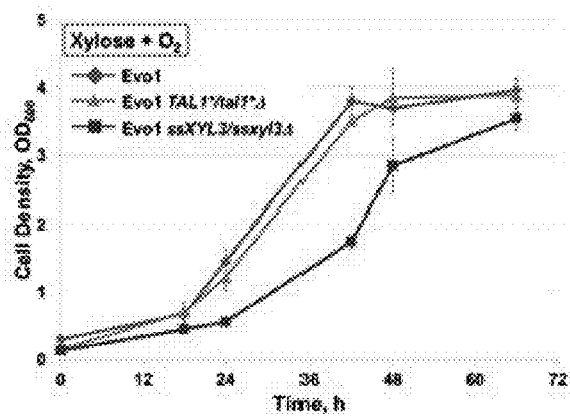
FIGS. 14A-14F. Evolved strains have different requirements for the extra copy of XYL3 and no requirement for the extra copy of TAL1 in aerobic xylose fermentation. The evolved strains (Evo1 and Evo2) and the evolved strains with a deletion of one copy of XYL3 or TAL1 were cultured aerobically in YPX medium. Average cell density (A, D), extracellular xylose (B, E), and ethanol (C, F) concentrations from independent triplicate experiments with SEM are reported. Asterisk (*) refers to the engineered copy of TAL1 (note that native TAL1 remained in all strains, so strains tested have 2 or 3 copies of TAL1). Evo1, Evo2, Evo1 TAL1*/tal1*Δ, Evo2 TAL1*/tal1*Δ, Evo1 ssXYL3/Ssxyl3Δ, and Evo2 ssXYL3/Ssxyl3Δ indicate strains Y1031, Y1033, Y1174, Y1181, Y1178, and Y1184, respectively.
Figure 14D:
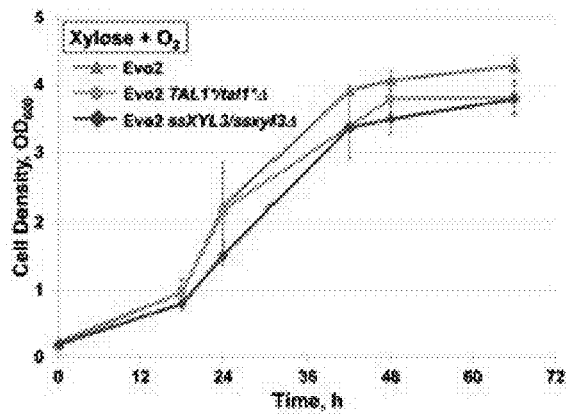
Figure 14B:
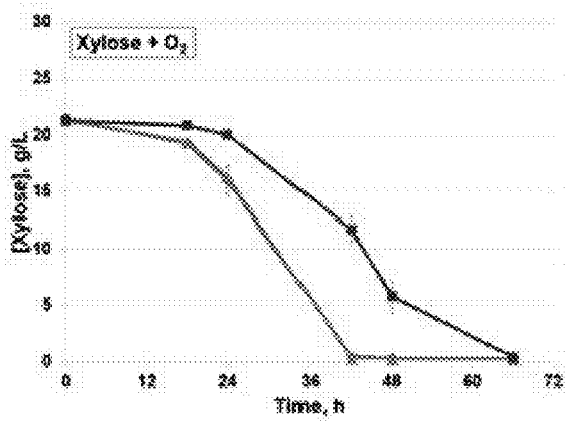
Figure 14E:
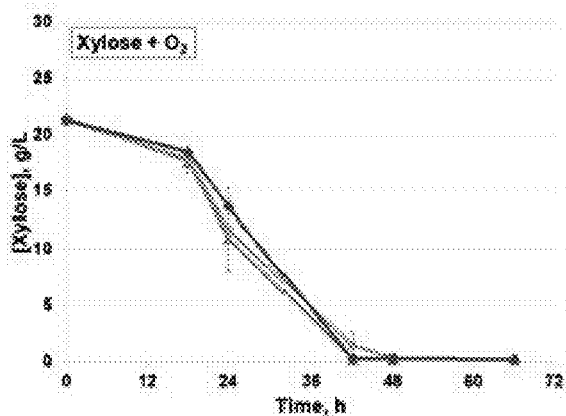
Figure 14C:
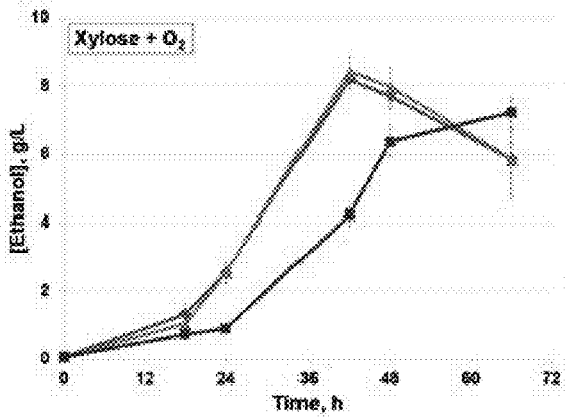
Figure 14F:
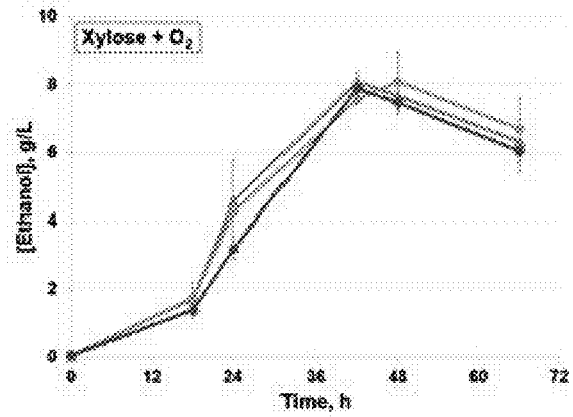
Figure 15A:
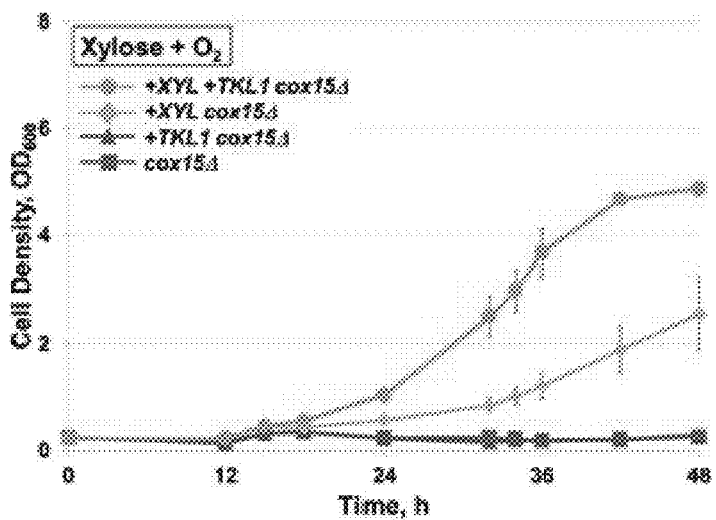
FIGS. 15A-15C. Duplication of the XYL cassette alone enables modest xylose fermentation aerobically. The engineered strains with deletion of COX15 were cultured aerobically in YPX medium. Average cell density (A), extracellular xylose (B), and ethanol (C) concentrations from independent triplicate experiments with SEM are reported. All the engineered strains were based on the gre3Δ hog1Δ isu1Δ ira2Δ mutant strain containing one copy of the XYL cassette and TKL1 as the Parent strain. cox15Δ, +XYL cox15Δ, +TKL1 cox15Δ, and +XYL+TKL1 cox15Δ, indicate strains Y1370, Y1372, Y1406, and Y1374, respectively.
Figure 15B:
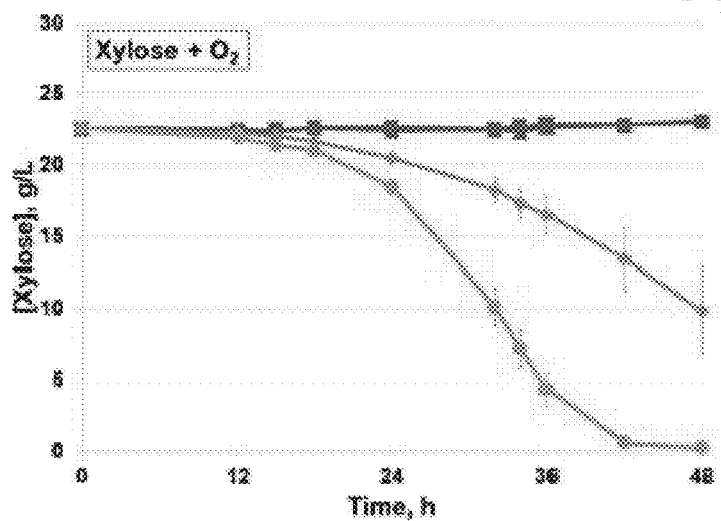
Figure 15C:
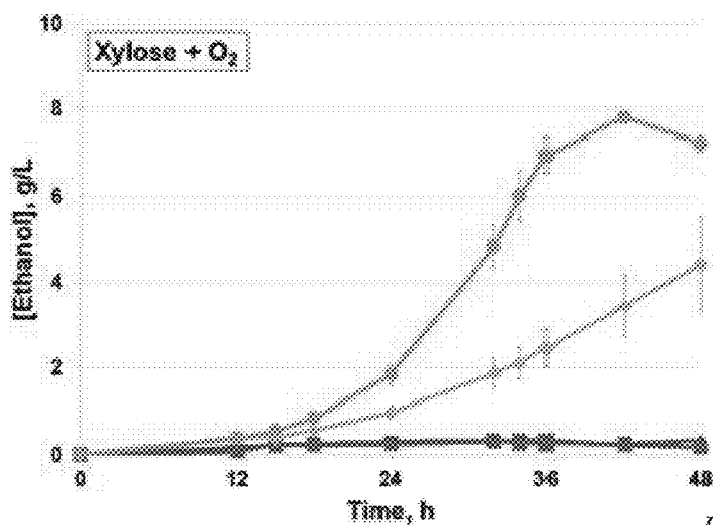
Figure 16A:
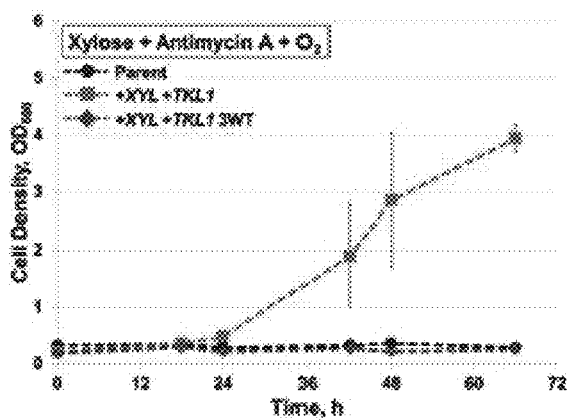
FIGS. 16A-16F. Duplications of the XYL cassette and TKL1 enable respiration-dependent growth on xylose aerobically. The engineered strains with wild-type COX15 were cultured aerobically in YPX (A-C) and YPD (D-F) media containing 0.5 μg/mL Antimycin A. Average cell density (A, D), extracellular xylose (B, E), and ethanol (C, F) concentrations from independent triplicate experiments with SEM are reported. All the engineered strains were based on the gre3Δ hog1Δ isu1Δ ira2Δ mutant strain containing one copy of the XYL cassette and TKL1 as the Parent strain. 3WT indicates a genotype of wild types HOG1, ISU1, and IRA2. Parent, +XYL+TKL1, and +XYL+TKL1 3WT indicate strains Y560, Y1327, and Y1348, respectively.
Figure 16D:
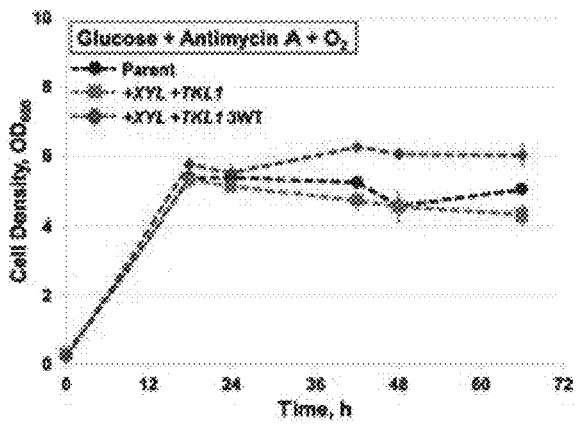
Figure 16B:
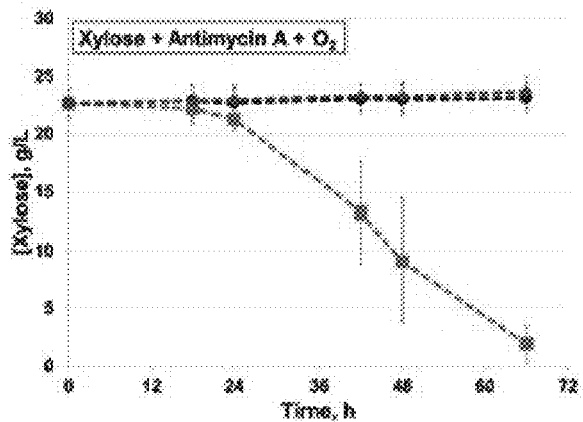
Figure 16E:
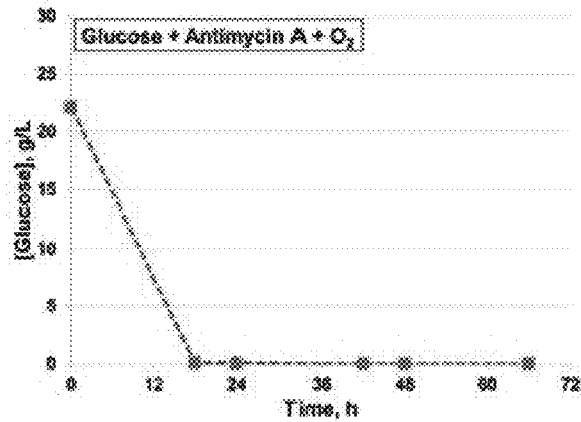
Figure 16C:
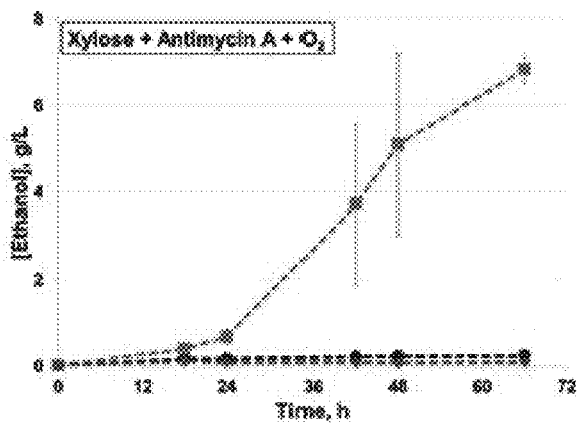
Figure 16F:
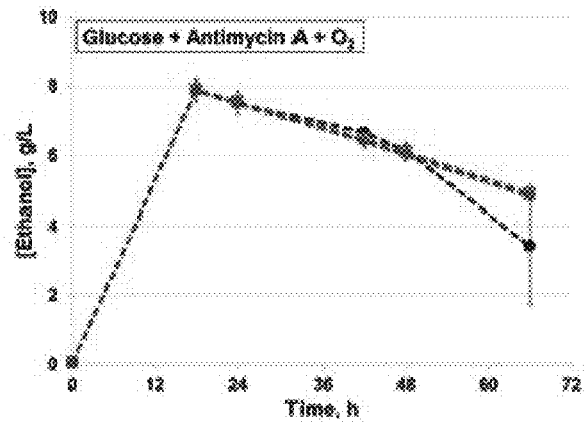
Figure 17A:
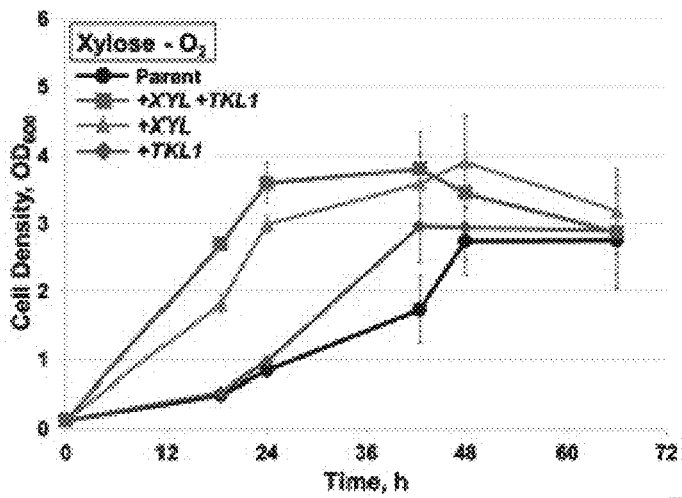
FIGS. 17A-17C. The combination of the duplicated XYL cassette and TKL1 enable faster xylose fermentation anaerobically. The engineered strains with wild-type COX15 were cultured anaerobically in YPX medium. Average cell density (A), extracellular xylose (B), and ethanol (C) concentrations from independent triplicate experiments with SEM are reported. All the engineered strains were based on the gre3Δ hog1Δ isu1Δ ira2Δ mutant strain containing one copy of the XYL cassette and TKL1 as the Parent strain. Parent, +XYL, +TKL1, and +XYL+TKL1 indicate strains Y560, Y1228, Y1309, and Y1327, respectively.
Figure 17B:
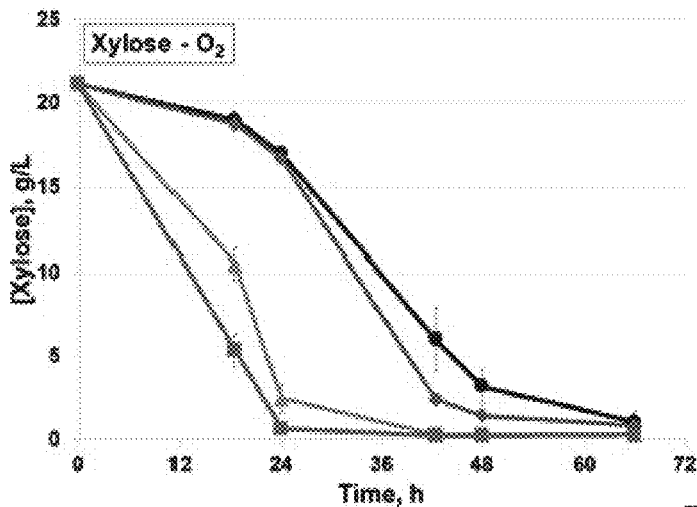
Figure 17C:
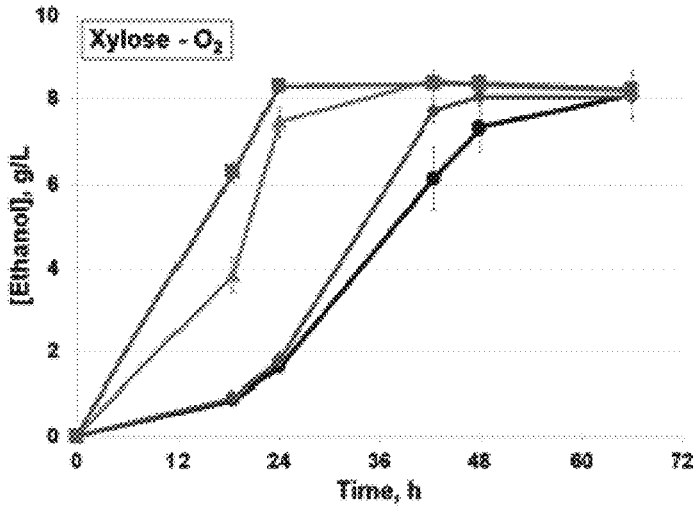

Duplicated Genes Synergize with Hog1Δ, Isu1Δ, and Ira2Δ Mutations to Enhance Xylose Conversion Aerobically and Anaerobically To directly test whether additional copies of the xylose metabolism genes and TKL1 enable xylose fermentation aerobically without respiration, second copies of the XYL cassette and TKL1 were engineered into the Parent strain containing the cox15Δ mutation. The cox15Δ strain engineered with additional copies of the xylose metabolism genes and TKL1 displayed rapid consumption of and growth on xylose aerobically (FIG. 5A-C), similarly to the Evo1 and Evo2 strains. In contrast, insertion of an additional copy of TKL1 into the cox15Δ strain did not enable growth on xylose aerobically, while insertion of a second copy of the XYL cassette caused modestly faster growth aerobically on xylose (FIG. 15). This result suggests that duplications of the XYL cassette and TKL1 together allow for respiration-independent aerobic xylose fermentation. When two copies of the XYL cassette and TKL1 were engineered into the cox15Δ strain containing wild-type HOG1, ISU1, and IRA2 (denoted as "3WT"), the strain did not metabolize xylose aerobically (FIG. 5A-C). This result further suggests that the hog1Δ, isu1Δ, and ira2Δ mutations, in combination with two copies of the XYL cassette and TKL1, enable aerobic xylose fermentation. It was shown that the increased rates of xylose conversion into ethanol by the evolved yeast strains were not dependent upon the deletion of COX15 aerobically or anaerobically (FIGS. 12 and 13). Similarly, it was found that expressing second copies of the XYL cassette and TKL1 in the COX15-containing Parent strain also increased the rates of xylose consumption and ethanol production aerobically (FIG. 6) and increased overall xylose fermentation anaerobically (FIG. 5D-F). Interestingly, when the Parent strain was engineered with a duplicated XYL cassette and TKL1, as well as wild-type HOG1, ISU1, and IRA2, it grew rapidly on xylose aerobically but produced very low amounts of ethanol, suggesting that this strain primarily respired xylose (FIG. 6). Indeed, aerobic growth and consumption of xylose, but not glucose, by this strain were completely blocked in the presence of Antimycin A. In contrast, the Parent strain engineered with the duplicated XYL cassette and TKL1, and containing deletion mutations in HOG1, ISU1, and IRA2 maintained rapid xylose conversion into ethanol aerobically under Antimycin A treatment (FIG. 16). Together, these results suggest that additional copies of the XYL cassette and TKL1 enhance aerobic respiration of xylose, while deletions of HOG1, ISU1, and IRA2 redirect xylose metabolism from respiration to fermentation. The Parent strain engineered with both the additional XYL cassette and the additional copy of TKL1, along with wild-type HOG1, ISU1, and IRA2 did not grow on xylose anaerobically (FIG. 5D-F). This result further supports the conclusion that two copies of the xylose metabolism genes and TKL1 synergize with mutations in HOG1, ISU1, GRE3, and IRA2 to promote both aerobic and anaerobic xylose fermentation. When the Parent strain was engineered with an additional copy of TKL1 or the XYL cassette alone, more modest increases in the rate of xylose conversion into ethanol anaerobically were observed (FIG. 17).

Engineered Gene Duplications and Deletion Mutations have Broad Utility

Figure 18A:
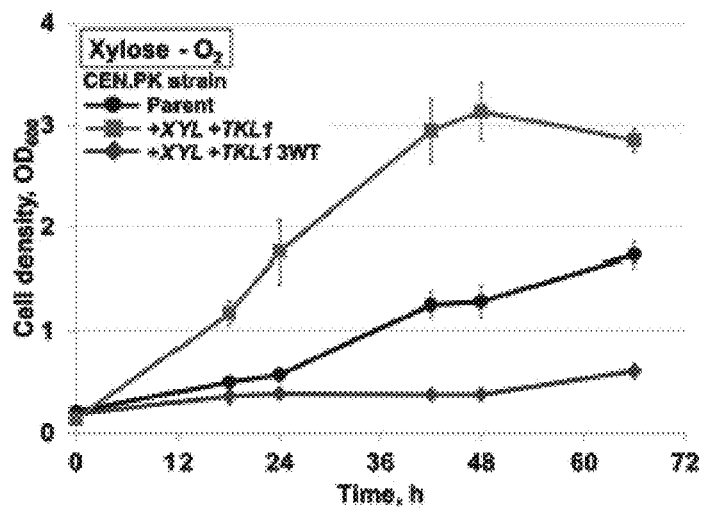
FIGS. 18A-18C. Duplications of the XYL cassette and TKL1 together with deletion mutations in HOG1, ISU1, GRE3, and IRA2 enable faster anaerobic xylose fermentation in the CEN.PK strain background. The engineered CEN.PK113-5D strains with wild-type COX15 were cultured anaerobically in YPX medium. Average cell density (A), extracellular xylose (B), and ethanol (C) concentrations from independent triplicate experiments with SEM are reported. All the engineered CEN.PK113-5D strains were based on the gre3Δ hog1Δ isu1Δ ira2Δ mutant strain containing one copy of the XYL cassette and TKL1 as the Parent strain. 3WT indicates a genotype of wild types HOG1, ISU1, and IRA2. Parent, +XYL+TKL1, and +XYL+TKL1 3WT indicate strains Y176, Y1429, and Y1431, respectively.
Figure 18B:
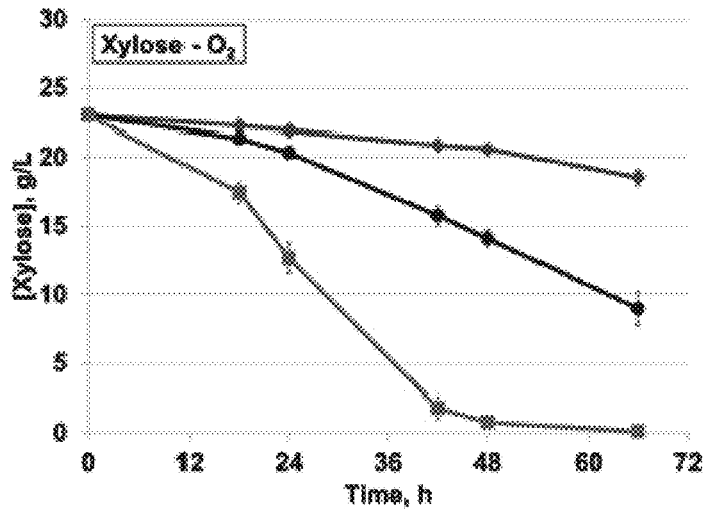
Figure 18C:
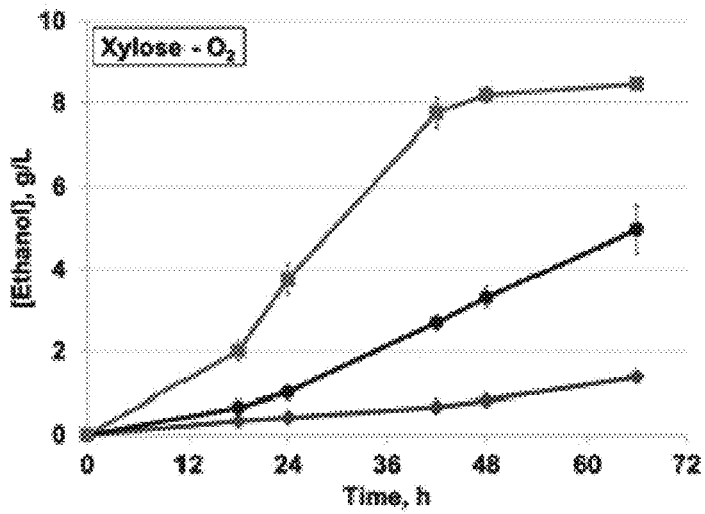

Mutations in HOG1 and IRA2/PKA pathway genes, as well as ISU1, have been shown to enhance xylose metabolism in multiple strain backgrounds (Dos Santos et al., 2016; Osiro et al., 2019; Sato et al., 2016), suggesting that these genetic modifications have universal utility. Similarly, the generality of the disclosed genetic modifications in another strain background was tested. First, additional copies of the XYL cassette and TKL1 were introduced into the commonly used strain CEN.PK113-5D (Landi et al., 2011). As in the Y22-3 strain background, extra copies of the XYL cassette and TKL1 significantly enhanced anaerobic xylose fermentation in the CEN.PK113-5D background also containing mutations in HOG1, ISU1, GRE3, and IRA2 (FIG. 18). However, these genetic duplications were not effective in the CEN.PK113-5D background containing wild-type HOG1, ISU1, and IRA2. These results suggest that the genetic modifications disclosed herein can be applied to different strain backgrounds.

Engineering the Duplications and Deletion Mutations Improves the Rate of Xylose Fermentation in Industrially Relevant Switchgrass Hydrolysate As another test of the utility of the genetic modifications, it was investigated whether the combination of gene duplications and deletions enables accelerated xylose fermentation from pretreated and hydrolyzed lignocellulosic biomass to ethanol. Specifically, a comparison of the Parent strain containing single copies of the XYL cassette and TKL1, as well as deletion mutations in HOG1, ISU1, GRE3, and IRA2; the engineered Parent strain with extra copies of the XYL cassette and TKL1; and the modified Parent strain containing duplications of the XYL cassette and TKL1, but containing wild-type HOG1, ISU1, and IRA2, was conducted. The three strains were cultured anaerobically in bioreactors containing AFEX-pretreated switchgrass hydrolysate (ASGH) (Tables 1 and 2), which contains inhibitory compounds that are known to inhibit cell growth and fermentation (Parreiras et al., 2014). As when cultured anaerobically in YPX media (FIG. 5D-F), the engineered Parent strain containing extra copies of the XYL cassette and TKL1 consumed xylose and produced ethanol significantly faster than the Parent strain, whereas the ethanol yield from xylose was not significantly different between these two strains (Table 1). The modified Parent strain containing the duplications but wild-type HOG1, ISU1, and IRA2 consumed little xylose and did not produce ethanol from xylose. These results suggest that extra copies of the XYL cassette and TKL1, in combination with deletion mutations in HOG1, ISU1, and IRA2, enable accelerated xylose conversion from lignocellulosic hydrolysate into ethanol anaerobically. On the other hand, duplications of the XYL cassette and TKL1 did not affect glucose conversion kinetics, whereas deletion mutations in HOG1, ISU1, and IRA2 slightly improved glucose consumption and ethanol production rates (Table 3). Thus, the genetic modifications could improve industrial processes by significantly and specifically improving the conversion of xylose into biofuels from lignocellulosic biomass.

TABLE 1

Xylose conversion kinetics of engineered *S. cerevisiae* strains from AFEX-pretreated switchgrass hydrolysate (ASGH) fermentations.

| Strain | Y1348 (+XYL, +TKL1, 3WT) | Y560 (4Δ) | Y1327 (+XYL, +TKL1, 4Δ) |
|---|---|---|---|
| Specific xylose consumption rate[1] | 0.010 ± 0.008* | 0.048 ± 0.008** | 0.098 ± 0.004 |
| Specific ethanol production rate from xylose[2] | ND | 0.013 ± 0.002*** | 0.028 ± 0.004 |
| Ethanol productivity from xylose[3] | ND | 0.064 ± 0.011** | 0.16 ± 0.01 |
| % of theoretical yield from xylose [4] | ND | 43.9 ± 8.2 | 55.9 ± 7.8 |

[1]In g xylose consumed/OD$_{600}$/h ± SEM
[2]In g ethanol produced/OD$_{600}$/h ± SEM
[3]In g ethanol produced/L/h ± SEM
[4] Percentage of maximum theoretical ethanol yield ± SEM
ND = Not determined; the rate of ethanol production did not exceed the rate of stripping
3WT = HOG1 ISU1 IRA2
4Δ = gre3Δ hog1Δ isu1Δ ira2Δ
*p < 0.05, Y1348 vs. Y1327
**p < 0.05, Y560 vs. Y1327
***p < 0.07, Y560 vs. Y1327

All the experiments were performed in biological triplicate.

TABLE 2

*Saccharomyces cerevisiae* strains used in this study.

| Strain Name (GLBRCY#) | Name in Figure | Description | Reference |
|---|---|---|---|
| Y22-3 | | NRRL YB-210MATa spore HOΔ::ScTAL1-CpXylA-SsXYL3-LoxP-KanMX-LoxP | Parreiras et al. (2014) |
| Y36 | 3WT | Y22-3 with LoxP-KanMX-LoxP maker excised by Cre | Parreiras et al. (2014) |
| Y286 | | Y36 gre3Δ::LoxP ira2Δ::LoxP hog1Δ::LoxP-KanMX-LoxP isu1Δ::LoxP | Sato et al. (2016) |
| Y560 | Parent | Y286 with LoxP-KanMX-LoxP maker excised by Cre | This study |
| Y583 | cox15Δ | Y286 cox15Δ::LoxP-HphMX-LoxP | This study |
| Y1031 | Evo1 | Y583 from aerobic xylose ALE flask B and without KanMX and HphMX cassettes | This study |
| Y1033 | Evo2 | Y583 from aerobic xylose ALE flask A and without KanMX and HphMX cassettes | This study |
| Y1031 + Empty | Evo1 + Empty | Y1031 transformed with pRSCENHygMX plasmid | This study |
| Y1033 + Empty | Evo2 + Empty | Y1033 transformed with pRSCENHygMX plasmid | This study |
| Y1031 + COX15 | Evo1 + COX15 | Y1031 transformed with pRSCENHygMX-COX15 plasmid | This study |
| Y1033 + COX15 | Evo2 + COX15 | Y1033 transformed with pRSCENHygMX-COX15 plasmid | This study |
| Y1176 | Evo1 xylA/xylaΔ | Evo1 ScTAL1-CpXylA-SsXYL3-LoxP/TAL1-xylaΔ::LoxP-KanMX-LoxP-SsXYL3 | This study |
| Y1183 | Evo2 xylA/xylaΔ | Evo2 ScTAL1-CpXylA-SsXYL3-LoxP/TAL1-xylaΔ::LoxP-KanMX-LoxP-SsXYL3 | This study |
| Y1185 | Evo1 TKL1/tkl1Δ | Evo1 TKL1/tkl1Δ::LoxP-KanMX-LoxP | This study |
| Y1189 | Evo2 TKL1/tkl1Δ | Evo2 TKL1/tkl1Δ::LoxP-KanMX-LoxP | This study |
| Y1327 | +XYL +TKL1 | Y560 gre3Δ::ScTAL1-CpXylA-SsXYL3 ChrI::ScTKL1 | This study |
| Y1348 | +XYL +TKL1 3WT | Y560 gre3Δ::ScTAL1-CpXylA-SsXYL3 ChrI::ScTKL1 with wild-type HOG1, ISU1 and IRA2 | This study |
| Y1374 | +XYL +TKL1 cox15Δ | Y1327 cox15Δ::LoxP-KanMX-LoxP | This study |
| Y1376 | +XYL +TKL1 3WT cox15Δ | Y1348 cox15Δ::LoxP-KanMX-LoxP | This study |

TABLE 3

Glucose conversion kinetics of engineered *S. cerevisiae* strains from ASGH fermentations.

| Strain | Y1348 (+XYL, +TKL1, 3WT) | Y560 (4Δ) | Y1327 (+XYL, +TKL1, 4Δ) |
|---|---|---|---|
| Exponential growth rate[1] | 0.19 ± 0.01* | 0.13 ± 0.01 | 0.13 ± 0.01 |
| Specific glucose consumption rate[2] | 1.36 ± 0.10* | 1.86 ± 0.13 | 1.84 ± 0.06 |
| Specific ethanol production rate from glucose[3] | 0.58 ± 0.03* | 0.82 ± 0.06 | 0.85 ± 0.02 |
| Ethanol productivity from glucose[4] | 2.27 ± 0.60 | 1.75 ± 0.20** | 1.61 ± 0.16 |
| % of theoretical yield from glucose[5] | 90.3 ± 2.3 | 88.5 ± 1.8 | 89.4 ± 2.4 |

[1]In $OD_{600}$/h ± SEM
[2]In g glucose consumed/$OD_{600}$/h ± SEM
[3]In g ethanol produced/$OD_{600}$/h ± SEM
[4]In g ethanol produced/L/h ± SEM
[5]Percentage of maximum theoretical ethanol yield ± SEM
3WT = HOG1 ISU1 IRA2
4Δ = gre3Δ hog1Δ isu1Δ ira2Δ
*$p < 0.05$, Y1348 vs. Y1327
**$p < 0.06$, Y560 vs. Y1327

All the experiments were performed in biological triplicate.

TABLE 4

Xylose conversion kinetics of engineered S. cerevisiae strains from AFEX-pretreated switchgrass hydrolysate (ASGH) fermentations.

| Strain | Y1348 (+XYL +TKL1 3WT) | Y560 (Parent) | Y1327 (+XYL +TKL1) |
|---|---|---|---|
| Specific xylose consumption rate[a] | $0.010 \pm 0.008^e$ | $0.048 \pm 0.008^f$ | $0.098 \pm 0.004$ |
| Specific ethanol production rate from xylose[b] | ND | $0.013 \pm 0.002^g$ | $0.028 \pm 0.004$ |
| Ethanol productivity from xylose[c] | ND | $0.064 \pm 0.011^f$ | $0.16 \pm 0.01$ |
| % of theoretical yield from xylose[d] | ND | $43.9 \pm 8.2$ | $55.9 \pm 7.8$ |

ND = Not determined; the rate of ethanol production did not exceed the rate of stripping. 3WT = HOG1 ISU1 IRA2.
[a] In g xylose consumed/$OD_{600}$/h ± SEM.
[b] In g ethanol produced/$OD_{600}$/h ± SEM.
[c] In g ethanol produced/L/h ± SEM.
[d] Percentage of maximum theoretical ethanol yield ± SEM.
[e] $p < 0.05$, Y1348 vs. Y1327.
[f] $p < 0.05$, Y560 vs. Y1327.
[g] $p < 0.07$, Y560 vs. Y1327.

Discussion

Xylose has been targeted as a prospective carbon source for producing sustainable biofuels since it is the second most abundant sugar in plant-derived biomass (Lee et al., 2021). Thus, many studies have attempted to engineer S. cerevisiae to efficiently convert xylose into biofuels in a manner comparable to easily fermentable sugars like glucose (Demeke et al., 2015; Dos Santos et al., 2016; Feng et al., 2018; Lee et al., 2020; Parreiras et al., 2014; Sato et al., 2016; Zeng et al., 2017). The Crabtree/Warburg Effect was first described in tumor cells where lactate was aerobically fermented in high levels of glucose, along with decreased respiration (Crabtree, 1929; Warburg et al., 1927). This phenomenon also occurs in S. cerevisiae, which ferments high levels of glucose into ethanol under aerobic conditions (Pfeiffer and Morley, 2014). A similar effect has not been observed with xylose and other carbon sources in yeasts because it requires high metabolic flux, which is achieved for glucose partially through the repression of other metabolic pathways and the upregulation of hexose transporters and glycolytic enzymes (Kayikci and Nielsen, 2015; Pfeiffer and Morley, 2014). Through ALE and genetic manipulations, it was determined that a suite of genetic changes enable strains to grow on xylose aerobically without respiration (FIG. 3). These genetic changes impart a trait that is analogous to the Crabtree-Warburg Effect for xylose, although repression by glucosamine (FIG. 11) indicates that the aerobic fermentation of xylose and glucose are still using different metabolic and regulatory pathways.

Increased expression of metabolic enzymes by integrating multiple gene copies has been shown by others to increase the rate of xylose utilization and anaerobic fermentation. In particular, several studies engineered S. cerevisiae with genes overexpressing xylose isomerase (xylA), xylulokinase (XYL3), and non-oxidative pentose phosphate pathway (RKI1, RPE1, TAL1, TKL1, TKL2, and NQM1) in combination with the deletion of the gene encoding aldose reductase, GRE3 (Bracher et al., 2019; Demeke et al., 2013; Kuyper et al., 2005; Verhoeven et al., 2017). Deletions of several genes involved in iron-sulfur cluster biogenesis (ISU1) and various signaling pathways (HOG1, IRA2, BCY1, and SSK1) can also contribute to improved xylose metabolic flux in strains engineered with xylose isomerase, likely by reprogramming regulatory systems (Dos Santos et al., 2016; Myers et al., 2019; Sato et al., 2016; Wagner et al., 2019). Herein, it is disclosed that increased copy number of the XYL cassette and TKL1 played roles enabling aerobic xylose fermentation in a strain containing deletion mutations in HOG1, ISU1, and IRA2 (FIGS. 5A-C and 6), a trait not previously described in any yeast strain. Adding only a second copy of the XYL cassette resulted in increased xylose fermentation rate, whereas adding only a second copy of TKL1 had no effect on xylose fermentation (FIG. 15). Thus, in addition to the regulatory mutations, at least two copies of xylA allow for enzymatic capacity to initiate xylose fermentation aerobically, while a second copy of TKL1 further enhances this trait. Moreover, two copies of both the XYL cassette and TKL1 led to increased xylose fermentation rate anaerobically in lab medium and switchgrass hydrolysate (FIGS. 5D-F, and 17, and Table 1), demonstrating that the genetic changes also increase xylose metabolic flux in industrially relevant conditions.

The precise mechanism by which the mutations in HOG1, ISU1, and IRA2 synergize to enable xylose fermentation has been unclear, but recent studies suggest that these mutations alter how S. ceervisiae sense xylose. Osiro and colleagues determined that the responses of three major sugar-signaling pathways, including cAMP/PKA, Snf3p/Rgt2p, and Snf1p/Mig1p, by wild-type strains cultured in high xylose concentrations were similar to the signals induced by low glucose concentrations (Osiro et al., 2018), which typically promote respiration under aerobic conditions. In contrast, the authors later demonstrated that isu1Δ ira2Δ double mutants cultured in high xylose concentrations displayed activation of some high-glucose signaling pathways, suggesting that these mutations may promote the recognition of xylose as a fermentable sugar (Osiro et al., 2019). In support of this view, it was shown herein that deletions of HOG1, ISU1, and IRA2 caused the up-regulation of both the PKA and Snf1 pathways on xylose (Myers et al., 2019). PKA is normally activated in response to high glucose concentrations to promote growth and glucose fermentation, while Snf1 is normally activated when non-preferred carbon sources are consumed; this unusual regulatory combination seems to promote the fermentation of xylose with rapid uptake and high metabolic flux (Myers et al., 2019). Sugar uptake and growth rates also correlate with the hypothesized regulation of overflow metabolism by sensing glycolytic flux (Huberts et al., 2012; Litsios et al., 2018). When glycolytic flux surpasses a specific point of respiratory capacity, metabolism switches from respiration to fermentation due to the overflow of pyruvate flux to ethanol and other fermentation products (Dashko et al., 2014; Hagman and Piskur, 2015; Niebel et al., 2019). Thus, deletions of HOG1, ISU1, and IRA2 together may cause S. cerevisiae to initiate similar, but not identical, metabolic activities with xylose.

As shown herein, increasing xylose conversion in this primed regulatory background resulted in overflow metabolism of xylose into ethanol. Specifically, loss-of-function mutations in HOG1, ISU1, and IRA2 significantly increased xylose consumption and ethanol production rates aerobically in strains containing either one or two copies of the XYL cassette and TKL1 (FIG. 6), whereas the strain containing two copies of the XYL cassette and TKL1 with wild-type HOG1, ISU1, and IRA2 mostly respired xylose aerobically (FIG. 6) and did not grow on xylose anaerobically (FIG. 5D-F). These results indicate that overexpression of xylose isomerase and the pentose phosphate pathway enzymes increase total metabolic conversion, while the altered regulatory pathways prime yeast to ferment xylose. Collectively, these genetic changes increase the flux of xylose into ethanol by enabling a form of xylose overflow metabolism that is analogous to how the Crabtree-Warburg Effect enables glucose fermentation under aerobic conditions (FIG. 16). Importantly, this increased metabolism also translates into faster rates of xylose fermentation in more industrially relevant anaerobic conditions.

Figure 7:
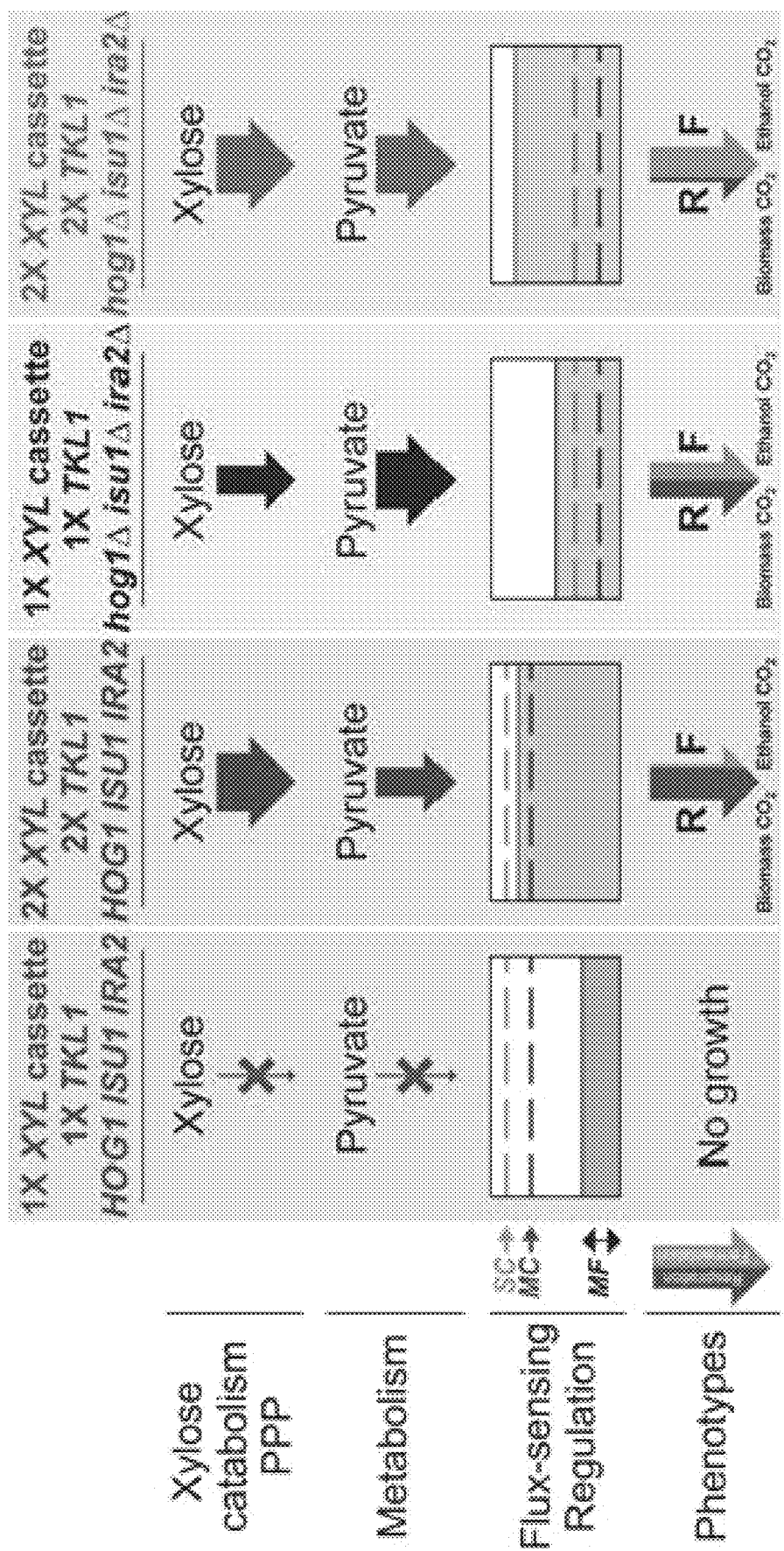
FIG. 7. Proposed model for aerobic xylose metabolic fluxes, including Crabtree-Warburg-like overflow into fermentation. The wild-type strain contains one copy of the XYL cassette and TKL1 with wild-type copies of HOG1, ISU1, and IRA2. SC, the minimal switching capacity for changing metabolic flux from respiration to fermentation; MC, a minimal capacity for enabling respiratory metabolism; MF, total metabolic flux of the strains. R, respiratory flux; F, fermentative flux.

To synthesize the present observations with published work, a model of aerobic, Crabtree-Warburg-like metabolic flux for xylose is proposed (FIG. 7). It is assumed that xylose-fermenting strains have a minimal capacity (MC) for enabling aerobic growth through respiration and a minimal switching capacity (SC) for changing from respiratory to fermentative flux. Once total metabolic flux exceeds the MC value, a strain can utilize xylose through respiration. (FIG. 7, second column). Regulatory pathways altered in hog1Δ isu1Δ ira2Δ triple mutants lower both MC and SC, causing the total metabolic flux (MF) of the strain to exceed both capacities. As xylose consumption rates and MF level increase beyond this lowered SC level, yeast begin to switch metabolic flux from respiration into fermentation. For yeast containing both the deletion mutations and the duplicated copies of the XYL cassette and TKL1 (FIG. 7, right-most green column), the increased metabolic flux far exceeds the switching capacity, resulting in much greater conversion of xylose into ethanol aerobically.

CONCLUSION

Disclosed herein are defined genetic modifications that enable multiple xylose isomerase-expressing *S. cerevisiae* strains to successfully convert xylose from lab media and switchgrass hydrolysate into ethanol both aerobically and anaerobically. The theoretical yield of ethanol from xylose was still lower than that from glucose. However, altering tolerance to lignocellulose-derived inhibitors, to improve xylose uptake, and to derepress genes involved in xylose metabolism may improve the yield. Furthermore, the evolved strains have slightly different aneuploidies, and the Evo2 strain is more efficient for aerobic and anaerobic xylose fermentation than the Evo1 strain, suggesting that there are additional unknown mutations that may improve xylose conversion. Nonetheless, the yeast strains described here are able to ferment xylose anaerobically, and also preferentially fermenting xylose in the presence of oxygen, a hallmark of the Crabtree-Warburg Effect previously only seen in yeast during the aerobic fermentation of glucose.

REFERENCES

Bamba et al., *AMB Express.* 6:4 (2016).
Barros et al., *FEBS Lett.*, 492:133 (2001).
Bracher et al., *FEMS Yeast Res.*, 19: (2019).
Brat et al., *Appl. Environ. Microbiol.*, 75:2304 (2009).
Conant & Wolfe, *PLoS Biol.*, 4:e109 (2006).
Crabtree, *Biochem J.*, 23:536 (1929).
Cunha et al., *Biotechnol. Biofuels*, 2:20 (2019).
Dashko et al., *Fems. Yeast Res.*, 4:826 (2014).
Demeke et al., *Biotechnol. Biofuels*, 6:89 (2013).
Demeke et al., *Plos Genetics*, 11:_(2015).
Dos Santos et al., *Sci. Rep.*, 6:38676 (2016).
Feng et al., *PLoS One*, 3:e0195633 (2018).
Gietz et al., *Nat. Protoc.*, 2:31 (2007).
Glerum et al., *J. Biol. Chem.*, 272:19088 (1997).
Guldener et al., *Nucleic Acids Res.*, 24:2519 (1996).
Hagman & Piskur, *PLoS One*, 10e0116942 (2015).
Hahn-Hagerdal et al., *Appl. Microbiol. Biotechnol.*, 74:937 (2007).
Higgins et al., *Genetics*, 210:219 (2018).
Hittinger & Carroll, *Nature*, 449:677 (2007).
Huberts et al., *Ferns. Yeast Res.*, 12:118 (2012).
Jeong et al., *PLoS One*, 15:e0236294 (2020).
Jin et al., *Appl. Environ. Microbiol.*, 70:6816 (2004).
Jin et al., *J. Microbiol. Biotechn.*, 10:564 (2000).
Johansson et al., *Appl. Environ. Microb.*, 67:4249 (2001).
Johnston & Kim, *Biochem. Soc. T.*, 33:247 (2005).
Kayikci & Nielsen, *FEMS Yeast Res.*, 15: (2015).
Kim et al., *Biotechnol. Adv.*, 31:851 (2013).
Kotter & Ciriacy, *Appl. Microbiol. Biot.*, 38:776 (1993).
Kuyper et al., *FEMS Yeast Res.*, 5:399 (2005).
Kwak & Jin, *Microb. Cell Fact*, 16:82 (2017).
Landi et al., *Biochem. Biophys. Res. Commun.*, 414:604 (2011).
Langdon et al., *Mol. Biol. Evol.*, 35:2835 (2018).
Lee et al., *Curr. Opin. Biotechnol.*, 67:15 (2021).
Lee et al., *Biotechnol. Biofuels*, 13:5 (2020).
Lee et al., *Appl. Environ. Microbiol.*, 78:5708 (2012).
Lee et al., *Biotechnol. Biofuels*, 7:122 (2014).
Li, Aligning sequence reads, clone sequences and assembly contigs with BWA-MEM. arXiv preprint arXiv: 1303.3997 (2013).
Lin & Li, *Mol. Biol. Evol.*, 28:131 (2011).
Litsios et al., *Curr. Opin. Microbiol.*, 42:71 (2018).
Magtanong et al., *Nat. Biotechnol.*, 29:505 (2011).
McIlwain et al., *G3-Genes Genom. Genet.*, 6:1757 (2016).
McKenna et al., *Genome Res.*, 20:1297 (2010).
Myers et al., *PLoS Genet.*, 15:e1008037 (2019).
Narayanaswamy et al., *Bioresour. Technol.*, 102:6995 (2011).
Niebel et al., *Nat. Metab.*, 1:125 (2019).
Osiro et al., *Microb. Cell. Fact.*, 18:88 (2019).
Osiro et al., *FEMS Yeast Res.*, 18:_(2018).
Parreiras et al., *PLoS One*, 9:e107499 (2014).
Pauly & Keegstra, *Plant J.*, 54:559 (2008).
Pfeiffer & Morley, *Front. Mol. Biosci.*, 1:17 (2014).
Pronk et al., *Yeast*, 12:1607 (1996).
Reider Apel et al., *Sci. Rep.*, 6:19512 (2016).
Runquist et al., *Microb. Cell. Fact.*, 8:49 (2009).
Salusjarvi et al., *Microb. Cell. Fact.*, 7:18 (2008).
Sato et al., *PLoS Genet.*, 12:e1006372 (2016).
Scalcinati et al., *FEMS Yeast Res.*, 12:582 (2012).
Schwalbach et al., *Appl. Environ. Microbiol.*, 78:3442 (2012).
Sherman, *Methods Enzymol.*, 350:3 (2002).
Stoneman et al., *G3 (Bethesda)*, 10:4287 (2020).
Sun & Jin, *Biotechnol. J.*, 16:e2000142 (2021).
Thompson et al., *Elife*, 2:e00603 (2013).
Traff et al., *Appl. Environ. Microbiol.*, 67:5668 (2001).
Verhoeven et al., *Sci. Rep.*, 7:46155 (2017).
Wagner et al., *PLoS One*, 14:e0212389 (2019).
Warburg et al., *J. Gen. Physiol.*, 8:519 (1927).
Williams et al., *Front Energy Res.*, 6: (2019).
Yamanaka, *Arch. Biochem. Biophys.*, 131:502 (1969).
Zeng et al., *Appl. Microbiol. Biotechnol.*, 101:1753 (2017).
Zhang et al., *Bioresource Tech. Rep.*, 11:100517 (2020).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A recombinant yeast that has been genetically engineered to:
   (a) include one or more copies of one or more non-native genes that facilitate xylose fermentation, wherein the non-native genes encode a xylulokinase or a xylose isomerase;
   (b) include one or more additional copies of one or more genes that encode a transaldolase or a transketolase, or both; and
   (c) include a disabling mutation in a gene encoding Cox15 polypeptide so as to exhibit reduced amounts of functional Cox15 polypeptide;
   and optionally include one or more of a disabling mutation in a gene encoding Isu1 polypeptide so as to exhibit reduced amounts of functional Isu1 polypeptide, a disabling mutation in a gene encoding Hog1 polypeptide so as to exhibit reduced amounts of functional Hog1 polypeptide, a disabling mutation in a gene encoding Ira2 polypeptide so as to exhibit reduced amounts of functional Ira2 polypeptide, or a disabling mutation in a gene encoding Gre3 polypeptide so as to exhibit reduced amounts of functional Gre3 polypeptide, or any combination thereof; or
   a recombinant yeast that has been genetically engineered to:
   (a) include two or more copies of two or more non-native genes that include genes that encode a xylulokinase and a xylose isomerase, and one or more additional copies of a native gene that encodes a transaldolase; or
   (b) include one or more additional copies of one or more native genes that include a gene that encodes a transketolase;
   and optionally include one or more of a disabling mutation in a gene encoding Cox15 so as to exhibit reduced amounts of functional Cox15 polypeptide, a disabling mutation in a gene encoding Isu1 polypeptide so as to exhibit reduced amounts of functional Isu1 polypeptide, a disabling mutation in a gene encoding Hog1 polypeptide so as to exhibit reduced amounts of functional Hog1 polypeptide, a disabling mutation in a gene encoding Ira2 polypeptide so as to exhibit reduced amounts of functional Ira2 polypeptide, or a disabling mutation in a gene encoding Gre3 polypeptide so as to exhibit reduced amounts of functional Gre3 polypeptide, or any combination thereof.

2. The recombinant yeast of claim 1 wherein the genes for the xylulokinase and the xylose isomerase are from different microbes.

3. The recombinant yeast of claim 1 wherein the gene for the xylulokinase is from a different genus or species of yeast than the recombinant yeast cell.

4. The recombinant yeast of claim 1 wherein the gene encoding the xylose isomerase is from a bacterium.

5. The recombinant yeast of claim 4 wherein the bacterium is *Streptomyces, Clostridium, Streptomyces, Bacillus* or *Bacteroides*.

6. The recombinant yeast of claim 1 which has at least two copies of the xylulokinase gene.

7. The recombinant yeast of claim 1 which has one copy of the xylulokinase gene.

8. The recombinant yeast of claim 1 which has one copy of the xylose isomerase gene.

9. The recombinant yeast of claim 1 which has at least two copies of the xylose isomerase gene.

10. The recombinant yeast of claim 1 which has one additional copy of the transketolase gene.

11. The recombinant yeast of claim 1 which has one additional copy of the transaldolase gene.

12. The recombinant yeast of claim 1 wherein the disabling mutation in the gene encoding Isu1 comprises a substitution of a tyrosine for the histidine at amino acid residue position 138 of SEQ ID NO:3, the disabling mutation in the gene encoding Hog1 comprises a deletion of the adenine at nucleotide position 844 of a nucleotide sequence having SEQ ID NO:7, or a combination thereof.

13. The recombinant yeast of claim 1 wherein the transketolase has at least 80% amino acid sequence identity to SEQ ID NO:17 or SEQ ID NO:18, the transaldolase has at least 80% amino acid sequence identity to SEQ ID NO:19 or SEQ ID NO:20, the xylose isomerase has at least 80% amino acid sequence identity to any one of SEQ ID NOs: 10-12, or the xylulokinase has at least 80% amino acid sequence identity to any one of SEQ ID NOs: 13-16.

14. A yeast inoculum, comprising:
(a) the recombinant yeast of claim 1; and
(b) a culture medium.

15. A method of fermenting a hydrolysate having xylose into ethanol, comprising:
contacting under ethanol-producing conditions the recombinant yeast of claim 1 and the hydrolysate for a period of time sufficient to allow fermentation of at least a portion of the hydrolysate into ethanol.

16. The method of claim 15 further comprising hydrolyzing a cellulosic material to produce the hydrolysate comprising xylose; and contacting the recombinant yeast to the hydrolysate under conditions that permit fermentation.

17. The method of claim 16 wherein the cellulosic material comprises a lignocellulosic biomass.

18. The method of claim 15 wherein the conditions include aerobic conditions.

19. The method of claim 15 wherein the conditions include anaerobic conditions.

20. The method of claim 15 wherein the hydrosylate is a plant hydrosylate comprising corn stover, poplar, sugarcane bagasse, or switchgrass.

* * * * *

```
                               SEQUENCE LISTING

Sequence total quantity: 20
SEQ ID NO: 1            moltype = DNA   length = 20
FEATURE                 Location/Qualifiers
source                  1..20
                        mol_type = other DNA
                        organism = synthetic construct
SEQUENCE: 1
atgaaggaga aaactcaccg                                                    20

SEQ ID NO: 2            moltype = AA   length = 3079
FEATURE                 Location/Qualifiers
source                  1..3079
                        mol_type = protein
                        organism = synthetic construct
SEQUENCE: 2
MSQPTKNKKK EHGTDSKSSR MTRTLVNHIL FERILPILPV ESNLSTYSEV EEYSSFISCR    60
SVLINVTVSR DANAMVEGTL ELIESLLQGH EIISDKGSSD VIESILIILR LLSDALEYNW   120
QNQESLHYND ISTHVEHDQE QKYRPKLNSI LPDYSSTHSN GNKHFFHQSK PQALIPELAS   180
KLLESCAKLK FNTRTLQILQ NMISHVHGNI LTTLSSSILP RHKSYLTRHN HPSHCKMIDS   240
TLGHILRFVA ASNPSEYFEF IRKSVQVPVT QTHTHSHSHS HSLPSSVYNS IVPHFDLFSF   300
IYLSKHNFKK YLELIKNLSV TLRKTIYHCL LLHYSAKAIM FWIMARPAEY YELFNLLKDN   360
NNEHSKSLNT LNHTLFEEIH STFNVNSMIT TNQNAHQGSS SPSSSSPSSP PSSSSSDNNN   420
QNIIAKSLSR QLSHHQSYIQ QQSERKLHSS WTTNSQSSTS LSSSTSNSTT TDFSTHTQPG   480
EYDPSLPDTP TMSNITISAS SLLSQTPTPT TQLQQRLNSA AAAAAAASP  SNSTPTGYTA   540
EQQSRASYDA HKTGHTGKDY DEHFLSVTRL DNVLELYTHF DDTEVLPHTS VLKFLTTLTM   600
FDIDLFNELN ATSFKYIPDC TMHRPKERTS SFNNTAHETG SEKTSGIKHI TQGLKKLTSL   660
PSSTKKTVKF VKMLLRNLNG NQAVSDVALL DTMRALLSFF TMTSAVFLVD RNLPSVLFAK   720
RLIPIMGTNL SVGQDWNSKI NNSLMVCLKK NSTTFVQLQL IFFSSAIQFD HELLLARLSI   780
DTMANNLNMQ KLCLYTEGFR IFFDIPSKKE LRKAIAVKIS KFFKTLFSII ADILLQEFPY   840
FDEQITDIVA SILDGTIINE YGTKKHFKGS SPSLCSTTRS RSGSTSQSSM TPVSPLGLDT   900
DICPMNTLSL VGSSTSRNSD NVNSLNSSPK NLSSDPYLSH LVAPRARHAL GGPSSIIRNK   960
IPTTLTSPPG TEKSSPVQRP QTESISATPM AITNSTPLSS AAFGIRSPLQ KIRTRRYSDE  1020
SLGKFMKSTN NYIQEHLIPK DLNEATLQDA RRIMINIFSI FKRPNSYFII PHNINSNLQW  1080
VSQDFRNIMK PIFVAIVSPD VDLQNTAQSF MDTLLSNVIT YGESDENISI EGYHLLCSYT  1140
VTLFAMGLFD LKINNEKRQI LLDITVKFMK VRSHLAGIAE ASHHMEYISD SEKLTFPLIM  1200
GTVGRALFVS LYSSQQKIEK TLKIAYTEYL SAINFHERNI DDADKTWVHN IEFVEAMCHD  1260
NYTTSGSIAF QRRTRNNILR FATIPNAILL DSMRMIYKKW HTYTHSKSLE KQERNDFRNF  1320
AGILASLSGI LFINKKILQE MYPYLLDTVS ELKKNIDSFI SKQCQWLNYP DLLTRENSRD  1380
ILSVELHPLS FNLLFNNLRL KLKELACSDL SIPENESSYV LLEQIIKMLR TILGRDDDNY  1440
VMMLFSTEIV DLIDLLTDEI KKIPAYCPKY LKAIIQMTKM FSALQHSEVN LGVKNHFHVK  1500
NKWLRQITDW FQVSIAREYD FENLSKPLKE MDLVKRDMDI LYIDTAIEAS TAIAYLTRHT  1560
FLEIPPAASD PELSRSRSVI FGFYFNILMK GLEKSSDRDN YPVFLRHKMS VLNDNVILSL  1620
TNLSNTNVDA SLQFTLPMGY SGNRNIRNAF LEVFINIVTN YRTYTAKTDL GKLEAADKFL  1680
RYTIEHPQLS SFGAAVCPAS DIDAYAAGLI NAFETRNATH IVVAQLIKNE IEKSSRPTDI  1740
LRRNSCATRS LSMLARSKGN EYLIRTLQPL LKKIIQNRDF FEIEKLKPED SDAERQIELF  1800
VKYMNELLES ISNSVSYFPP PLFYICQNIY KVACEKFPDH AIIAAGSFVF LRFFCPALVS  1860
PDSENIIDIS HLSEKRTFIS LAKVIQNIAN GSENFSRWPA LCSQKDFLKE CSDRIFRFLA  1920
ELCRTDRTID IQVRTDPTPI AFDYQFLHSF VYLYGLEVRR NVLNEAKHDD GDIDGDDFYK  1980
TTFLLIDDVL GQLGQPKMEF SNEIPIYIRE HMDDYPELYE FMNRHAFRNI ETSTAYSPSV  2040
HESTSSEGIP IITLTMSNFS DRHVDIDTVA YKFLQIYARI WTTKHCLIID CTEFDEGGLD  2100
MRKFISLVMG LLPEVAPKNC IGCYYFNVNE TFMDNYGKCL DKDNVYVSSK IPHYFINSNS  2160
DEGLMKSVGI TGQGLKVLQD IRVSLHDITL YDEKRNRFTP VSLKIGDIYF QVLHETPRQY  2220
KIRDMGTLFD VKFNDVYEIS RIFEVHVSSI TGVAAEFTVT FQDERRLIFS SPKYLEIVKM  2280
FYYAQIRLES EYEMDNNSST SSPNSNNKDK QQKERTKLLC HLLLVSLIGL FDESKKMKNS  2340
SYNLIAATEA SFGLNFGSHF HRSPEVYVPE DTTTFLGVIG KSLAESNPEL TAYMFIYVLE  2400
ALKNNVIPHV YIPHTICGLS YWIPNLYQHV YLADDEEGPE NISHIFRILI RLSVRETDFK  2460
AVYMQYVWLL LLDDGRLTDI IVDEVINHAL ERDSENRDWK KTISLLTVLP TTEVANNIIQ  2520
KILAKIRSFL PSLKLEAMTQ SWSELTILVK ISIHVFFETS LLVQMYLPEI LFIVSLLIDV  2580
GPRELRSSLH QLLMNVCHSL AINSALPQDH RNNLDEISDI FAHQKVKFMF GFSEDKGRIL  2640
QIFSASSFAS KFNILDFFIN NILLLMEYSS TYEANVWKTR YKKYVLESVF TSNSFLSARS  2700
IMIVGIMGKS YITEGLCKAM LIETMKVIAE PKITDEHLFL AISHIFTYSK IVEGLDPNLD  2760
LMKHLFWFST LFLESRHPII FEGALLFVSN CIRRLYMAQF ENESETSLIS TLLKGRKFAH  2820
TFLSKIENLS GIVWNEDNFT HILIFIINKG LSNPFIKSTA FDFLKMMFRN SYFEHQINQK  2880
SDHYLCYMFL LYFVLNCNQF EELLGDVDFE GEMVNIENKN TIPKILLEWL SSDNENANIT  2940
LYQGAILFKC SVTDEPSRFR FALIIRHLLT KKPICALRFY SVIRNEIRKI SAFEQNSDCV  3000
PLAFDILNLL VTHSESNSLE KLHEESIERL TKRGLSIVTS SGIFAKNSDM MIPLDVKPED  3060
IYERKRIMTM ILSRMSCSA                                               3079

SEQ ID NO: 3            moltype = AA   length = 165
FEATURE                 Location/Qualifiers
source                  1..165
                        mol_type = protein
                        organism = synthetic construct
```

```
SEQUENCE: 3
MLPVITRFAR PALMAIRPVN AMGVLRASSI TKRLYHPKVI EHYTHPRNVG SLDKKLPNVG    60
TGLVGAPACG DVMRLQIKVN DSTGVIEDVK FKTFGCGSAI ASSSYMTELV QGMTLDDAAK   120
IKNTEIAKEL SLPPVKLHCS MLAEDAIKAA IKDYKSKRNT PTMLS                   165

SEQ ID NO: 4              moltype = AA   length = 327
FEATURE                   Location/Qualifiers
source                    1..327
                          mol_type = protein
                          organism = synthetic construct
SEQUENCE: 4
MSSLVTLNNG LKMPLVGLGC WKIDKKVCAN QIYEAIKLGY RLFDGACDYG NEKEVGEGIR    60
KAISEGLVSR KDIFVVSKLW NNFHHPDHVK LALKKTLSDM GLDYLDLYYI HFPIAFKYVP   120
FEEKYPPGFY TGADDEKKGH ITEAHVPIID TYRALEECVD EGLIKSIGVS NFQGSLIQDL   180
LRGCRIKPVA LQIEHHPYLT QEHLVEFCKL HDIQVVAYSS FGPQSFIEMD LQLAKTTPTL   240
FENDVIKKVS QNHPGSTTSQ VLLRWATQRG IAVIPKSSKK ERLLGNLEIE KKFTLTEQEL   300
KDISALNANI RFNDPWTWLD GKFPTFA                                       327

SEQ ID NO: 5              moltype = AA   length = 435
FEATURE                   Location/Qualifiers
source                    1..435
                          mol_type = protein
                          organism = synthetic construct
SEQUENCE: 5
MTTNEEFIRT QIFGTVFEIT NRYNDLNPVG MGAFGLVCSA TDTLTSQPVA IKKIMKPFST    60
AVLAKRTYRE LKLLKHLRHE NLICLQDIFL SPLEDIYFVT ELQGTDLHRL LQTRPLEKQF   120
VQYFLYQILR GLKYVHSAGV IHRDLKPSNI LINENCDLKI CDFGLARIQD PQMTGYVSTR   180
YYRAPEIMLT WQKYDVEVDI WSAGCIFAEM IEGKPLFPGK DHVHQFSIIT DLLGSPPKDV   240
INTICSENTL KFVTSLPHRD PIPFSERFKT VEPDAVDLLE KMLVFDPKKR ITAADALAHP   300
YSAPYHDPTD EPVADAKFDW HFNDADLPVD TWRVMMYSEI LDPHKIGGSD GQIDISATFD   360
DQVAAATAAA AQAQAQAQAQ VQLNMAAHSH NGAGTTGNDH SDIAGGNKVS DHVAANDTIT   420
DYGNQAIQYA NEFQQ                                                   435

SEQ ID NO: 6              moltype = AA   length = 486
FEATURE                   Location/Qualifiers
source                    1..486
                          mol_type = protein
                          organism = synthetic construct
SEQUENCE: 6
MLFRNIEVGR QAAKLLTRTS SRLAWQSIGA SRNISTIRQQ IRKTQLYNFK KTVSIRPFSL    60
SSPVFKPHVA SESNPIESRL KTSKNVAYWL IGTSGLVFGI VVLGGLTRLT ESGLSITEWK   120
PVTGTLPPMN QKEWEEEFIK YKESPEFKLL NSHIDLDEFK FIFFMEWIHR LWGRAIGAVF   180
ILPAVYFAVS KKTSGHVNKR LFGLAGLLGL QGFVGWWMVK SGLDQEQLDA RKSKPTVSQY   240
RLTTHLGTAF FLYMGMLWTG LEILRECKWI KNPVQAISLF KKLDNPAIGP MRKISLALLA   300
VSFLTAMSGG MVAGLDAGWV YNTWPKMGER WFPSSRELMD ENFCRREDKK DLWWRNLLEN   360
PVTVQLVHRT CAYVAFTSVL AAHMYAIKKK AVIPRNAMTS LHVMMGVVTL QATLGILTIL   420
YLVPISLASI HQAGALALLT SSLVFASQLR KPRAPMRNVI ITLPHSSKVT SGKILSEASK   480
LASKPL                                                             486

SEQ ID NO: 7              moltype = DNA   length = 1308
FEATURE                   Location/Qualifiers
source                    1..1308
                          mol_type = other DNA
                          organism = synthetic construct
SEQUENCE: 7
atgaccacta acgaggaatt cattaggaca cagatattcg gtacagtttt cgagatcaca    60
aatagataca atgatttaaa ccccgttggg atgggggcat tgggttggt ttgctcagcc   120
acggacactt tgacatctca gccagttgcc attaagaaaa tcatgaaacc ttttccact   180
gcagtgctgg ccaaaaggac atatcgtgaa ctaaaactac taaacatct aagacacgag   240
aacttgattt gccttcagga catatttctt tctccattgg aagatatata ttttgtcacg   300
gaattacaag gaacagattt acatagactc ttgcaaacaa gacccttgga aaagcaattt   360
gttcagtatt tcctatacca aattctaagg ggtttaaaat acgttcactc cgcgggcgtc   420
attcatagag atttgaaacc gagcaacatt ctgattaatg aaaactgtga tttgaagatt   480
tgcgatttcg gtctagcaag aattcaagac cctcaaatga caggctatgt ttccactaga   540
tactacaggg caccctgaaat catgctaacg tggcaaaaat atgacgtcga ggtcgacatt   600
tggtccgctg gttgtatttt tgccgaaatg attgaaggta agccttttgtt ccctgggaaa   660
gatcatgttc accaatttc gatcatcact gacttgttgg gatctccgcc aaaggatgtt   720
ataaatacta tttgttccga aaatactcta aaatttgtta cttcgttacc acacagagat   780
ccaattccat tttctgaaag atttaaaaca gtcgaacctg atgccgtaga ccttttggaa   840
aaaatgctgg ttttgatcc taagaagaga atcactgcgg cggatgcctt ggctcatcct   900
tattcggctc cttaccacga tccaacggat gaaccagtag ccgatgccaa gttcgattgg   960
cactttaatg acgctgatct gcctgtcgat acctggcgtg ttatgatga ctcacaaatc  1020
ctagacttcc ataagattgg tggcagtgat ggacagattg atatatctgc cacgtttgat  1080
gaccaagttg ctgcagccac cgctgccgcg cgcaggcac aggctcaggc tcaggctcaa  1140
gttcagttaa acatggctgc gcattcgcat aatggcgctg gcactactgg aaatgatcac  1200
tcagatatag ctggtggaaa caaagtcagc gatcatgtag ctgcaaatga caccattacg  1260
gactacggta ccaggccat acagtacgct aatgagttcc aacagtaa            1308
```

| SEQ ID NO: 8 | moltype = DNA  length = 9632 |
|---|---|
| FEATURE | Location/Qualifiers |
| source | 1..9632 |
| | mol_type = other DNA |
| | organism = synthetic construct |

SEQUENCE: 8

```
cacccgtcct gtggatcatc tttttgccctg caaatagagc ttcaaactta acattcttct    60
tcagcatata acatacaaca agattaaggc tcttttctaaa atgaatcaaa gcgatccgca   120
agacaaaaaa aatttcccaa tggaatactc tttgaccaag catctttttt tttgataggc   180
ttctacttgt tcttcccata gaatctaatt tgaaaacata tgctgatgtg gaggcagatt   240
cagttttcaa ttcgtgtcgg tccatcattt tgaatatagc catcactaag gacttgaacc   300
cgattatcga aaacacatta ggtttaattg acttgattgt gcaagatgaa gaaattacgt   360
ctgacaatat tacagatgat attgcccatt ctatattggt tcttttgaga ttactgactg   420
atgttttga gtattactgg gatcaaaaca atgacttcaa gaaaattaga aacgataatt   480
acaaaccggg attttcaagt cacaggccaa acttccatac atctaggcca aagcacacga   540
gaatcaatcc agctttggcg acgatgttac tatgtaaaat ttctaagctg aagttcaata   600
caagaacttt aaaggtttta cagaacatgt ctcaccatct ttctggcagc gctactatct   660
caaaatcgag tattttaccc gattcacagg aattttaca aaagagaaac tatccagcat   720
ataccgagaa aatagattta acaatagatt atatccagag attcatatct gcttccaatc   780
atgttgaatt cacaaagtgt gtcaaaacaa agttgttgc accttattg atatcacaca   840
cctcaaccga attgggcgta gtaaaccact tggatttatt tggttgtgag tatttgactg   900
ataagaatct gctagcatat ctggacatac tacaaccct gtcaagttac atgaagagga   960
ccatttttca ttcgcttttg ttatattatg cttccaaagc tttttatt tggataatgg  1020
caaggccaaa agaatacgtc aaaatttata acaatctaat atcatcagat tataatagtc  1080
cgtcttcttc atctgataat ggtggttcga ataattctga taaaacgtct atatccaac  1140
tagtctcact gttattcgat gacgtttatt ccacttttag tggatcatca ttattaacaa  1200
atgtcaataa tgaccaccac taccatcttc atcattcatc ttcttcatca aagacgacca  1260
acactaatag tccaaactct atatcaaaaa cgtcgataaa gcagtcgagt gtgaatgctt  1320
ctggcaatgt ttctccgtct cagttttcta ctgggaatga tgcatcgcct acttcccta  1380
tggcatcatt gagttcaccc ttaaacacga acattctagg gtatccgtta tctccaatca  1440
cttcaacact aggacaggcg aatacttcca catcgactac ggctgcaact accaaaacag  1500
atgcagatac gccctctact atgaatacta acaacaataa taacaataac aacagcgcta  1560
atcttaataa tattccacaa cgcatatttt ccttagatga catttcatcc tttaactcga  1620
gtagaaaatc actcaatcta tgatgatagta actccttgtt tctttgggat acttctcagc  1680
attctaatgc atcgatgaca aatacaaata tgcatgcagg agttaataat tctcagtctc  1740
agaacgatca gtcttcttta aactatatgg aaaatattat ggagctgtat tccaactata  1800
ccggatcaga actatcctcc catactgcca tattaaggtt tttggtggtt ctgacctat   1860
tagacagtga agtatatgat gagatgaact caaatccgta tagaaaaatt tcggaaccga  1920
taatgaatat taatccgaag gactctaata cttcaagttg gggctcagca tccaaaaacc  1980
caagtatcag gcacctcacc catggcttaa aaaaacttac tttacagcaa ggcaggaaac  2040
gtaacgttaa attttgaca tatttgatta gaaatttgaa tgggggacag ttcgtttcag  2100
atgtttcctt gattgactct atcaggtcca ttctattctt aatgacaatg agtcttcta   2160
tatcccaaat cgattcaaat attgcttctg ttattttttc gaagagattc tacaacttgt  2220
tgggtcaaaa tttagaggtc ggcaccaatt ggaattctgc cactgcaaat acttttattt  2280
ctcattgtgt tgaaaggaat cccccttacac ataggcgttt acaattagag tttttttgcaa  2340
gcggtttaca gctggattct gatttatttt taagacatt acaactggaa aaagaactca  2400
atcacataga ccttcccaaa atatcgttat acactgaagg atttagggta ttttttcacc  2460
tagtaagcac caaaaaactt catgaggata ttgcagaaaa aacctcctct gtgttaaaga  2520
gacttttctg cataattgct gatattttgt tgaaagcaac gccttatttt gacgataatg  2580
taaccaagat tattgcttct atattggatg ggcatatttt agatcaattt gacgctgcg   2640
gaacactttc taatgatgat catgtcagtt ttgatgctgc cacaagcgtt tacactgagc  2700
caaccgaaat tattcataac tcatcggatg cctcgttagt ctcttcactt tcccaatcac  2760
ccttatcaat taactcagga agcaaatatca ccaatacgcg cacctgggat attcaatcaa  2820
tcttaccaac cttatcgaac agatcaagtg cttctgattt gagcttgtct aacattttga  2880
ctaatccgtt ggaggcacaa caaaataata atgcaaactt gttagcccat agattatctg  2940
gggttcctac tactaagaga tacgcttcac cgaacgactc tgaaagatca cgacaaagtc  3000
catattcttc tccgccgcaa ttgcaacaaa gtgacttgcc ttctccgctc tcagtcctct  3060
cgtcaagtgc aggattttct tctaatcatt cgattacgcc aaccccaact attttgaaaa  3120
acatcaaatc tccaaaacca aacaaaacaa aaaaaattgc tgatgataaa caattgaaac  3180
agccttctta ttcaagagta atactgagtg acaatgatga agcaagaaag attatgatga  3240
acatttcag cattttcaaa agaatgacca actggtttat acgccagat gctaatacag   3300
aattcccgaa gactttacg gatattataa aaccacttt tgtctctata ttggattcta  3360
atcaaagact acaagttaca gcgcgggctt ttattgaaat cccattaagt tatataagcta  3420
cttttgaaga cattgataat gatcttgacc caagagtact gaatgaccat tatttgttat   3480
gtacatatgc cgttactttg tttgcttcat cattgtttga tttgaagtta gaaaatgcga  3540
agagagat gctactagac attattgtta aatttcaacg agtccgttct tatttatcaa  3600
atttagcaga aaaacacaac ctagtccagg caataattac gacggagagg ttgacgctgc  3660
cattattagt tggtgctgta ggaagtggaa ttttcattc attactgc agtcgtggaa   3720
atacgccacg cttaataaaa atttcatgtt gtgaatttct acgatccttg agattttatc  3780
aaaaatacgt aggcgctttg gatcaatatt ccatttacaa tattgatttc atagatgcta  3840
tggcccagga caatttcact gcctcaggat cagtggcttt gcaacggcgt ctaagaaata  3900
atattttaac ttatatcaaa ggatccgact caatccttt ggattcaatg gacgtgattt  3960
acaagaagtg gttttactc agctgttcga aatcagttac gcaagaggaa ctagtagatt  4020
ttagaagctt ggcaggcatt ctagcttcta tgtcaggtat tctgtctgat atgcaagagt  4080
tggaaaaaag caagagcgct ccagataatg aaggagacag cttatcattt gagtcacgaa  4140
atcccgctta tgaggtgcac aaaagtctta aactcgagtt aacgaaaaaa atgaatttct  4200
tatttcaaa acaatgtcaa tggttgaata atccaaatct attaacaaga gaaaattcga  4260
gagatatatt aagtattgag ttgcatctcc tatcttttaa cttattgtt aacaacctag  4320
```

```
gactgaaaat agatgaactg atgtcaattg atctttcaaa gtcacatgag gattcatcgt   4380
ttgttttact agagcagata ataattataa taagaactat actaaagagg gatgatgatg   4440
aaaagataat gctactcttt tcgacggact tgcttgatgc ggtcgataag ttgatcgaaa   4500
tagtggagaa aatttccatc aagtcctcca aatattataa gggaattatc caatgtcga    4560
aaatgtttag agcatttgag cactctgaaa agaacctggg catttcaaat catttccatt   4620
taaagaataa atggttgaag ttagttattg gttggttcaa actatctatt aataaggatt   4680
atgattttga aaacctgtca agaccattaa gggaaatgga tttgcagaaa agggacgaag   4740
atttttttgta tatcgacact tctattgaat ctgcaaaagc attggcttac ctaacacata  4800
atgttccttt agaaataccg ccttcaagct caaaagaaga ttggaacaga tcttctacag   4860
tatcatttgg caatcacttt actattttgt taaaaggtct ggagaaaagc gcggacctga   4920
atcagtttcc agtttcatta aggcataaga tcagtatact taatgaaaat gtaataatag   4980
cgctaacgaa cttatctaat gccaatgtca acgtttcttt aaaattcact ttaccaatgg   5040
gttattctcc aaataaagat atcagaatcg cctttttaag agttttcatc gacatagtaa   5100
ccaactatcc agttaaccct gagaaacatg aaatggataa aatgctagct atagacgact   5160
tcctgaaata tataatcaag aacccaatat tagcatttt cggaagtta gcgtgttctc     5220
ctgctgatgt tgatttatat gctggtggat tcttaaacgc ctttgacact agaaatgcgt   5280
ctcatatcct tgttactgag ctccttaaac aagaaatcaa acgggccgca agatcagacg   5340
atattctcag aagaaatagt tgtgcaacaa gggctttgtc actttacact agatctagag   5400
gtaacaaata tttgataaaa actttgagac ccgttttgca agggatagtg gataacaagg   5460
agtcttttga aattgataag atgaaaccag gatccgaaaa ctccgaaaag atgttagact   5520
tatttgagaa gtacatgaca agattaattg acgcaattac aagttctatt gatgatttcc   5580
caatagaatt agttgatatc tgtaaaacaa tttacaatgc tgctagtgta aattttccag   5640
aatacgcata tattgccgtt gggtcattcg ttttcttgag gtttatcggg cctgcttag    5700
ttagtcctga ttcggaaaat atcattattg ttacgcacgc ccatgacaga aagcccttta   5760
ttacactagc taaagttatt caagtttag ctaatggcag ggaaatata ttcaagaaag     5820
atatcttagt ttcaaaagaa gagttttttga aaacctgtag tgataaaata ttcaattttt  5880
tgtctgaatt gtgcaagata ccgactaaca atttcaccgt caatgtaaga gaagatccga   5940
caccaataag ctttgactac tcattttgc ataaattctt ttacctcaat gagttttacca  6000
taagaaaaga aattattaat gaatccaaat taccaggga gttcagcttt ttgaaaaata   6060
ctgttatgct caacgacaaa attcttggtg tattgggaca acctagcatg gaaataaaaa   6120
atgaaattcc tccttttgta gtcgagaatc gggaaaaata tccttcattg tatgaattca   6180
tgagtcgcta tgccttcaaa aaagtggaca tgaaagaaga agaagaggat aatgcgccat   6240
ttgtacatga agcaatgaca ttggatggca tacaaatcat tgtcgtaact tttaccaatt   6300
gcgagtacaa taattttgta atggactcac tggtctataa agttctgcag atatatgcaa   6360
gaatgtggtg ctctaaacat tatgtagtta tcgattgtac cacctttat gggggtaagg   6420
ctaatttcca aaaattgact actctatttt tcagtttgat accagagcaa gcatcaagta   6480
attgtatggg atgttattac ttcaacgtca acaaatcatt tatggaccaa tgggcctcat   6540
catatactgt agaaaatccg tacttggtca ctacaattcc ccgttgtttc atcaacagca   6600
atactgacca aagtttgata aagtccttag gattgagtgg taggagtttg gaagttttga   6660
aagatgtaag agttactttg catgatatta ccctttatga caaggaaaaa agaagttttt   6720
gtcccgtgtc cttgaagata ggaaacaaat acttccaagt tttacatgag attccgcagt   6780
tgtacaaggt taccgtatca aacaggacat tcagcatcaa attcaacaat gtttacaaga   6840
tatcaaattt aatttcagtc gatgtctcta acaccacagg cgtttcctcg gaatttacgt   6900
taagtcttga taatgaagaa aagttggtat tttgcagtcc gaagtaccta gaaattgtga   6960
aaatgtttta ttatgcccag ttaaagatgg aagaagactt tggtacggat ttttcgaacg   7020
atatttcatt ttcaacatcc tcttcagcag ttaatgcttc ttactgcaat gttaaagaag   7080
ttggtgaaat tatatcacat ttgtcattgg tgatccttgt aggttttattc aatgaggatg  7140
atctcgtcaa aaacatatca tacaaccttc tcgtggcaac gcaagaagca tttaatttag   7200
attttgggac aaggcttcac aaatcccag agacatatgt acccgatgat accaccacgt    7260
tcttggcct aattttcaag gctttttcag aatcttcaac ggaactaact ccatatatat    7320
ggaaatatat gctggatggc cttgaaaacg acgtgattcc tcaagaacat attcctacgg   7380
ttgtctgttc attgtcatac tgggtaccaa acttatgta acatgtatat ttggcaaatg    7440
acgaagaggg accagaggcg atttcacgta taatctatag cttaatcagg ttgacggtca   7500
aagagccaaa tttcacgaca gcttaccttc aacagatttg gtttttactg gcattggatg   7560
gtcgtctcac gaacgtgata gttgaagaaa tagtaagtca tgcgctggat agagattcag   7620
aaaacagaga ctggatgaaa gctgtgtcaa tactaaccag ttttccaacg acagagattg   7680
cttgtcaggt aatagagaag ctaataaata tgatcaaatc ttttctacct tctctagcag   7740
ttgaggcttc cgcacacagt tggtctgagc ttactatttt atcaaaaatt agtgtgtcaa   7800
ttttcttga atcaccctta ctttcccaga tgtatttacc ggagattctt ttcgctgtgt    7860
ctctgttaat tgatgtcggt ccttcggaaa taagagtctc attgtacgag ttgttgatga   7920
atgtttgtca ttctttaacc aacaatgagt ccttacctga aaggaatagg aaaaatttgg   7980
atatcgtctg tgcaacattc gcacgtcaaa agttgaactt tatctccggt tttagccaag   8040
aaaaaggtag agttttacca aattttgccg cttcctcctt ctccagtaaa ttcggaacat   8100
tagatctctt cactaaaaac attatgctat tgatgaggta tggttctatt tcagaggtg    8160
cacaatggga ggcaaatat aagaaatatt tgatggatgc gattttggc catcggtcgt     8220
tcttctctgc gagagctatg atgattctag gtataatgag taagtcgcac acgtcccttt   8280
tcctttgtaa agaacttta gttgaaacca tgaaggtctt cgcagagcca gttgtggatg    8340
atgaacaaat gttcatcatt atagctcatg tctttactta cagcaaaatt gtcgaagggt   8400
tagatccttc ttcagaatta atgaaagagc tattttgct tgctacaata tgtgttgaat    8460
cccctcatcc tttactcttt gaaggtggtc tcctgttcat ggtaaattgt ttgaagcgac   8520
tgtacacggt ccatcttcaa cttggattcg atggcaaatc gctagccaaa aaattaatgg   8580
aatctagaaa ttttgctgct acgctttgg ctaagttaga gtcatacaat ggatgcatat    8640
ggaacgaaga taatttttcct catattttt taggtttcat tgcaaacggt ttatccattc   8700
ctgtcgtaaa aggagccgca ttagattgtc tacaggcct tttcaagaat acatattacg   8760
aaagaaagtc caacccaaaa tcctccgatt atctttgtta ccttttctta ctccattttgg  8820
tcttaagtcc tgaacaactt tctaccttgt tacttgaagt cggcttcgaa gatgaactgg   8880
tacctttaaa taatacacta aaagtgccac ttactttgat caactggcta agttcagact   8940
cagataaatc taatatagtc ttataccaag gagcactttt gtttagctgt gttatgtcag   9000
acgaaccatg taaattccgt tttgctctat tgatgaggta tttgctcaaa gtcaacccta   9060
```

```
tttgtgtatt caggttctat acgctgacta gaaaggaatt caggaggtta tcaaccctag   9120
aacaatcatc tgaagcggtt gctgtctctt tgaattgat tgggatgctt gttacacaca    9180
gtgagtttaa ttacctagag gaatttaatg atgaaatggt cgaacttta aaaaagagag    9240
gcttgtcagt tgtgaagcct ctggatattt ttgatcagga acatatgaa aagttaaaag    9300
gagagggtga acatcaagtg gcaatttatg agagaaaaag attagcaaca atgatactgg   9360
caagaatgtc gtgctcctaa ttttaaatta gagtattgca gtgattatat acgtttttcc   9420
ttataattat attttgtttt atatttgttg gattgtagat tttaaattaa atgaaacgta   9480
gagatttgtg taaagtataa tgattgcaag gttaagagtg aaacatttt agagcactac    9540
taactagcat tttccaaggt ggaaagatcc gaaaaagcac gattaccgga aatccaactg   9600
ttgaccattt ccaaacttgc ctccggttga tc                                 9632

SEQ ID NO: 9          moltype =    length =
SEQUENCE: 9
000

SEQ ID NO: 10         moltype = AA   length = 438
FEATURE               Location/Qualifiers
source                1..438
                      mol_type = protein
                      organism = synthetic construct
SEQUENCE: 10
MKNYFPNVPE VKYEGPNSTN PFAFKYYDAE RIVAGKTMKE HCRFALSWWH TLCAGGADPF    60
GVTTMDRSYG NITDPMEFAK AKVDAGFELM TKLGIEYFCF HDADIAPEGE NFEESKKNLF   120
VIVDYIKEKM DQTGIKLLWG TANNFGHPRF MHGASTSCNA DVFAYAAAKI KNALDATIKL   180
GGKGYVFWGG REGYETLLNT DLGLELDNMA RLMKMAVEYG RANGFDGDFY IEPKPKEPTK   240
HQYDFDTATV LGFLRKYGLE KDFKMNIEAN HATLAGHTFE HELALARVNG VFGSVDANQG   300
DPNLGWDTDQ FPTDVHSATL AMLEVLKAGG FTNGGLNFDA KVRRGSFEFD DIAYGYIAGM   360
DTFALGLIKA AEIIEDGRIA KFVEDRYASY KTGIGKAIVD GTTSLEELEQ YVLTHNEPVM   420
QSGRQEVLES IVNNILFR                                                 438

SEQ ID NO: 11         moltype = AA   length = 438
FEATURE               Location/Qualifiers
source                1..438
                      mol_type = protein
                      organism = synthetic construct
SEQUENCE: 11
MKNYFPNVPE VKYEGPNSTN PFAFKYYDAN KVVAGKTMKE HCRFALSWWH TLCAGGADPF    60
GVTTMDRTYG NITDPMELAK AKVDAGFELM TKLGIEFFCF HDADIAPEGD TFEESKKNLF   120
EIVDYIKEKM DQTGIKLLWG TANNFSHPRF MHGASTSCNA DVFAYAAAKI KNALDATIKL   180
GGKGYVFWGG REGYETLLNT DLGLELDNMA RLMKMAVEYG RANGFDGDFY IEPKPKEPTK   240
HQYDFDTATV LAFLRKYGLE KDFKMNIEAN HATLAGHTFE HELAMARVNG AFGSVDANQG   300
DPNLGWDTDQ FPTDVHSATL AMLEVLKAGG FTNGGLNFDA KVRRGSFEFD DIAYGYIAGM   360
DTFALGLIKA AEIIDDGRIA KFVDDRYASY KTGIGKAIVD GTTSLEELEQ YVLTHSEPVM   420
QSGRQEVLET IVNNILFR                                                 438

SEQ ID NO: 12         moltype = AA   length = 438
FEATURE               Location/Qualifiers
source                1..438
                      mol_type = protein
                      organism = synthetic construct
SEQUENCE: 12
MKNYFPNVPE VKYEGPNSTN PFAFKYYDAN KVVAGKTMKE HCRFALSWWH TLCAGGADPF    60
GVTTMDRTYG NITDPMELAK AKVDAGFELM TKLGIEFFCF HDADIAPEGD TFEESKKNLF   120
EIVDYIKEKM DQTGIKLLWG TANNFSHPRF MHGASTSCNA DVFAYAAAKI KNALDATIKL   180
GGKGYVFWGG REGYETLLNT DLGLELDNMA RLMKMAVEYG RANGFDGDFY IEPKPKEPTK   240
HQYDFDTATV LAFLRKYGLE KDFKMNIEAN HATLAGHTFE HELAMARVNG AFGSVDANQG   300
DPNLGWDTDQ FPTDVHSATL AMLEVLKAGG FTNGGLNFDA KVRRGSFEFD DIAYGYIAGM   360
DTFALGLIKA AEIIDDGRIA KFVDDRYASY KTGIGKAIVD GTTSLEELEQ YVLTHSEPVM   420
QSGRQEVLET IVNNILFR                                                 438

SEQ ID NO: 13         moltype = AA   length = 623
FEATURE               Location/Qualifiers
source                1..623
                      mol_type = protein
                      organism = synthetic construct
SEQUENCE: 13
MTTTPFDAPD KLFLGFDLST QQLKIIVTDE NLAALKTYNV EFDSINSSVQ KGVIAINDEI    60
SKGAIISPVY MWLDALDHVF EDMKKDGFPF NKVVGISGSC QQHGSVYWSR TAEKVLSELD   120
AESSLSSQMR SAFTFKHAPN WQDHSTGKEL EEFERVIGAD ALADISGSRA HYRFTGLQIR   180
KLSTRFKPEK YNRTARISLV SSFVASVLLG RITSIEEADA CGMNLYDIEK REFNEELLAI   240
AAGVHPELDG VEQDGEIYRA GINELKRKLG PVKPITYESE GDIASYFVTR YGFNPDCKIY   300
SFTGDNLATI ISLPLAPNDA LISLGTSTTV LIITKNYAPS SQYHLFKHPT MPDHYMGMIC   360
YCNGSLAREK VRDEVNEKFN VEDKKSWDKF NEILDKSTDF NNKLGIYFPL GEIVPNAAAQ   420
IKRSVLNSKN EIVDVELGDK NWQPEDDVSS IVESQTLSCR LRTGPMLSKS GDSSASSSAS   480
PQPEGDGTDL HKVYQDLVKK FGDLYTDGKK QTFESLTARP NRCYYVGGAS NNGSIIRKMG   540
SILAPVNGNY KVDIPNACAL GGAYKASWSY ECEAKKEWIG YDQYINRLFE VSDEMNSFEV   600
KDKWLEYANG VGMLAKMESE LKH                                           623
```

```
SEQ ID NO: 14             moltype = AA  length = 623
FEATURE                   Location/Qualifiers
source                    1..623
                          mol_type = protein
                          organism = synthetic construct
SEQUENCE: 14
MTTTPFDAPD KLFLGFDLST QQLKIIVTDE NLAALKTYNV EFDSINSSVQ KGVIAINDEI    60
SKGAIISPVY MWLDALDHVF EDMKKDGFPF NKVVGISGSC QQHGSVYWSR TAEKVLSELD   120
AESSLSSQMR SAFTFKHAPN WQDHSTGKEL EEFERVIGAD ALADISGSRA HYRFTGLQIR   180
KLSTRFKPEK YNRTARISLV SSFVASVLLG RITSIEEADA CGMNLYDIEK REFNEELLAI   240
AAGVHPELDG VEQDGEIYRA GINELKRKLG PVKPITYESE GDIASYFVTR YGFNPDCKIY   300
SFTGDNLATI ISLPLAPNDA LISLGTSTTV LIITKNYAPS SQYHLFKHPT MPDHYMGMIC   360
YCNGSLAREK VRDEVNEKFN VEDKKSWDKF NEILDKSTDF NNKLGIYFPL GEIVPNAAAQ   420
IKRSVLNSKN EIVDVELGDK NWQPEDDVSS IVESQTLSCR LRTGPMLSKS GDSSASSSAS   480
PQPEGDGTDL HKVYQDLVKK FGDLYTDGKK QTFESLTARP NRCYYVGGAS NNGSIIRKMG   540
SILAPVNGNY KVDIPNACAL GGAYKASWSY ECEAKKEWIG YDQYINRLFE VSDEMNSFEV   600
KDKWLEYANG VGMLAKMESE LKH                                          623

SEQ ID NO: 15             moltype = AA  length = 623
FEATURE                   Location/Qualifiers
source                    1..623
                          mol_type = protein
                          organism = synthetic construct
SEQUENCE: 15
MTTTPFDAPD KLFLGFDLST QQLKIIVTDE NLAALKTYNV EFDSINSSVQ KGVIAINDEI    60
SKGAIISPVY MWLDALDHVF EDMKKDGFPF NKVVGISGSC QQHGSVYWSR TAEKVLSELD   120
AESSLSSQMR SAFTFKHAPN WQDHSTGKEL EEFERVIGAD ALADISGSRA HYRFTGLQIR   180
KLSTRFKPEK YNRTARISLV SSFVASVLLG RITSIEEADA CGMNLYDIEK REFNEELLAI   240
AAGVHPELDG VEQDGEIYRA GINELKRKLG PVKPITYESE GDIASYFVTR YGFNPDCKIY   300
SFTGDNLATI ISLPLAPNDA LISLGTSTTV LIITKNYAPS SQYHLFKHPT MPDHYMGMIC   360
YCNGSLAREK VRDEVNEKFN VEDKKSWDKF NEILDKSTDF NNKLGIYFPL GEIVPNAAAQ   420
IKRSVLNSKN EIVDVELGDK NWQPEDDVSS IVESQTLSCR LRTGPMLSKS GDSSASSSAS   480
PQPEGDGTDL HKVYQDLVKK FGDLFTDGKK QTFESLTARP NRCYYVGGAS NNGSIIXKMG   540
SILAPVNGNY KVDIPNACAL GGAYKASWSY ECEAKKEWIG YDQYINRLFE VSDEMNSFEV   600
KDKWLEYANG VGMLAKMESE LKH                                          623

SEQ ID NO: 16             moltype = AA  length = 623
FEATURE                   Location/Qualifiers
source                    1..623
                          mol_type = protein
                          organism = synthetic construct
SEQUENCE: 16
MTTTPFDAPD KLFLGFDLST QQLKIIVTDE NLAALKTYNV EFDSINSSVQ KGVIAINDEI    60
SKGAIISPVY MWLDALDHVF EDMKKDGFPF NKVVGISGSC QQHGSVYWSR TAEKVLSELD   120
AESSLSSQMR SAFTFKHAPN WQDHSTGKEL EEFERVIGAD ALADISGSRA HYRFTGLQIR   180
KLSTRFKPEK YNRTARISLV SSFVASVLLG RITSIEEADA CGMNLYDIEK REFNEELLAI   240
AAGVHPELDG VEQDGEIYRA GINELKRKLG PVKPITYESE GDIASYFVTR YGFNPDCKIY   300
SFTGDNLATI ISLPLAPNDA LISLGTSTTV LIITKNYAPS SQYHLFKHPT MPDHYMGMIC   360
YCNGSLAREK VRDEVNEKFN VEDKKSWDKF NEILDKSTDF NNKLGIYFPL GEIVPNAAAQ   420
IKRSVLNSKN EIVDVELGDK NWQPEDDVSS IVESQTLSCR LRTGPMLSKS GDSSASSSAS   480
PQPEGDGTDL HKVYQDLVKK FGDLYTDGKK QTFESLTARP NRCYYVGGAS NNGSIIRKMG   540
SILAPVNGNY KVDIPNACAL GGAYKASWSY ECEAKKEWIG YDQYINRLFE VSDEMNSFEV   600
KDKWLEYANG VGMLAKMESE LKH                                          623

SEQ ID NO: 17             moltype = AA  length = 680
FEATURE                   Location/Qualifiers
source                    1..680
                          mol_type = protein
                          organism = synthetic construct
SEQUENCE: 17
MTQFTDIDKL AVSTIRILAV DTVSKANSGH PGAPLGMAPA AHVLWSQMRM NPTNPDWINR    60
DRFVLSNGHA VALLYSMLHL TGYDLSIEDL KQFRQLGSRT PGHPEFELPG VEVTTGPLGQ   120
GISNAVGMAM AQANLAATYN KPGFTLSDNY TYVFLGDGCL QEGISSEASS LAGHLKLGNL   180
IAIYDDNKIT IDGATSISFD EDVAKRYEAY GWEVLYVENG NEDLAGIAKA IAQAKLSKDK   240
PTLIKMTTTI GYGSLHAGSH SVHGAPLKAD DVQLKSKFG FNPDKSFVVP QEVYDHYQKT    300
ILKPGVEANN KWNKLFSEYQ KKFPELGAEL ARRLSGQLPA NWESKLPTYT AKDSAVATRK   360
LSETVLEDVY NQLPELIGGS ADLTPSNLTR WKEALDFQPP SSGSGNYSGR YIRYGIREHA   420
MGAIMNGISA FGANYKPYGG TFLNFVSYAA GAVRLSALSG HPVIWVATHD SIGVGEDGPT   480
HQPIETLAHF RSLPNIQVWR PADGNEVSAA YKNSLESKHT PSIIALSRQN LPQLEGSSIE   540
SASKGGYVLQ DVANPDIILV ATGSEVSLSV EAAKTLAAKN IKARVVSLPD FFTFDKQPLE   600
YRLSVLPDNV PIMSVEVLAT TCWGKYAHQS FGIDRFGASG KAPEVFKFFG FTPEGVAERA   660
QKTIAFYKGD KLISPLKKAF                                              680

SEQ ID NO: 18             moltype = AA  length = 680
FEATURE                   Location/Qualifiers
source                    1..680
                          mol_type = protein
                          organism = synthetic construct
```

```
SEQUENCE: 18
MTQFTDIDKL AVSTIRILAV DTVSKANSGH PGAPLGMAPA AHVLWSQMRM NPTNPDWINR   60
DRFVLSNGHA VALLYSMLHL TGYDLSIEDL KQFRQLGSRT PGHPEFELPG VEVTTGPLGQ  120
GISNAVGMAM AQANLAATYN KPGFTLSDNY TYVFLGDGCL QEGISSEASS LAGHLKLGNL  180
IAIYDDNKIT IDGATSISFD EDVAKRYEAY GWEVLYVENG NEDLAGIAKA IAQAKLSKDK  240
PTLIKMTTTI GYGSLHAGSH SVHGAPLKAD DVKQLKSKFG FNPDKSFVVP QEVYDHYQKT  300
ILKPGVEANN KWNKLFSEYQ KKFPELGAEL ARRLSGQLPA NWESKLPTYT AKDSAVATRK  360
LSETVLEDVY NQLPELIGGS ADLTPSNLTR WKEALDFQPP SSGSGNYSGR YIRYGIREHA  420
MGAIMNGISA FGANYKPYGG TFLNFVSYAA GAVRLSALSG HPVIWVATHD SIGVGEDGPT  480
HQPIETLAHF RSLPNIQVWR PADGNEVSAA YKNSLESKHT PSIIALSRQN LPQLEGSSIE  540
SASKGGYVLQ DVANPDIILV ATGSEVSLSV EAAKTLAAKN IKARVVSLPD FFTFDKQPLE  600
YRLSVLPDNV PIMSVEVLAT TCWGKYAHQS FGIDRFGASG KAPEVFKFFG FTPEGVAERA  660
QKTIAFYKGD KLISPLKKAF                                             680

SEQ ID NO: 19          moltype = AA  length = 335
FEATURE                Location/Qualifiers
source                 1..335
                       mol_type = protein
                       organism = synthetic construct
SEQUENCE: 19
MSEPAQKKQK VANNSLEQLK ASGTVVVADT GDFGSIAKFQ PQDSTTNPSL ILAAAKQPTY   60
AKLIDVAVEY GKKHGKTTEE QVENAVDRLL VEFGKEILKI VPGRVSTEVD ARLSFDTQAT  120
IEKARHIIKL FEQEGVSKER VLIKIASTWE GIQAAKELEE KDGIHCNLTL LFSFVQAVAC  180
AEAQVTLISP FVGRILDWYK SSTGKDYKGE ADPGVISVKK IYNYYKKYGY KTIVMGASFR  240
STDEIKNLAG VDYLTISPAL LDKLMNSTEP FPRVLDPVSA KKEAGDKISY ISDESKFRFD  300
LNEDAMATEK LSEGIRKFSA DIVTLFDLIE KKVTA                            335

SEQ ID NO: 20          moltype = AA  length = 335
FEATURE                Location/Qualifiers
source                 1..335
                       mol_type = protein
                       organism = synthetic construct
SEQUENCE: 20
MSEPAQKKQK VANNSLEQLK ASGTVVVADT GDFGSIAKFQ PQDSTTNPSL ILAAAKQPTY   60
AKLIDVAVEY GKKHGKTTEE QVENAVDRLL VEFGKEILKI VPGRVSTEVD ARLSFDTQAT  120
IEKARHIIKL FEQEGVSKER VLIKIASTWE GIQAAKELEE KDGIHCNLTL LFSFVQAVAC  180
AEAQVTLISP FVGRILDWYK SSTGKDYKGE ADPGVISVKK IYNYYKKYGY KTIVMGASFR  240
STDEIKNLAG VDYLTISPAL LDKLMNSTEP FPRVLDPVSA KKEAGDKISY ISDESKFRFD  300
LNEDAMATEK LSEGIRKFSA DIVTLFDLIE KKVTA                            335
```